(12) United States Patent
Schulze et al.

(10) Patent No.: US 9,586,958 B2
(45) Date of Patent: Mar. 7, 2017

(54) PRODRUG DERIVATIVES OF SUBSTITUTED TRIAZOLOPYRIDINES

(71) Applicant: BAYER PHARMA AKTIENGESELLSCHAFT, Berlin (DE)

(72) Inventors: Volker Schulze, OT Bergf (DE); Hans-Georg Lerchen, Leverkusen (DE); Donald Bierer, Haan (DE); Antje Margret Wengner, Berlin (DE); Gerhard Siemeister, Berlin (DE); Philip Lienau, Berlin (DE); Ursula Krenz, Leichlingen (DE); Dirk Kosemund, Berlin (DE); Detlef Stöckigt, Berlin (DE); Michael Brüning, Schildow (DE); Ulrich Lücking, Berlin (DE); Ildikó Terebesi, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/897,951

(22) PCT Filed: Jun. 6, 2014

(86) PCT No.: PCT/EP2014/061779
§ 371 (c)(1),
(2) Date: Dec. 11, 2015

(87) PCT Pub. No.: WO2014/198647
PCT Pub. Date: Dec. 18, 2014

(65) Prior Publication Data
US 2016/0207915 A1    Jul. 21, 2016

(30) Foreign Application Priority Data
Jun. 11, 2013   (EP) .................................... 13171508

(51) Int. Cl.
| | | |
|---|---|---|
| *C07D 471/02* | (2006.01) | |
| *C07D 471/04* | (2006.01) | |
| *C07F 9/6561* | (2006.01) | |
| *C07K 5/062* | (2006.01) | |
| *C07K 5/068* | (2006.01) | |
| *A61K 38/00* | (2006.01) | |

(52) U.S. Cl.
CPC .......... *C07D 471/04* (2013.01); *C07F 9/6561* (2013.01); *C07K 5/06052* (2013.01); *C07K 5/06086* (2013.01); *A61K 38/00* (2013.01)

(58) Field of Classification Search
CPC .................................................. C07D 471/04
USPC ....................................................... 546/119
See application file for complete search history.

(56) References Cited

U.S. PATENT DOCUMENTS

| 6,514,989 B1 | 2/2003 | Nettekoven et al. |
|---|---|---|
| 2008/0021059 A1 | 1/2008 | Butler et al. |
| 2008/0045536 A1 | 2/2008 | Vaccaro et al. |
| 2008/0090818 A1 | 4/2008 | Andrews et al. |
| 2012/0238565 A1 | 9/2012 | Swinnen et al. |

FOREIGN PATENT DOCUMENTS

| JP | 2004346016 A | 12/2004 |
|---|---|---|
| WO | 98/08847 A1 | 3/1998 |
| WO | 98/54158 A1 | 12/1998 |
| WO | 2004346016 A | 12/2004 |
| WO | 2005/030121 A2 | 4/2005 |
| WO | 2007/025090 A2 | 3/2007 |
| WO | 2007/038314 A2 | 4/2007 |
| WO | 2007/065010 A2 | 6/2007 |
| WO | 2008/021389 A2 | 2/2008 |
| WO | 2008/025821 A1 | 3/2008 |
| WO | 2008/141065 A1 | 11/2008 |
| WO | 2009/010530 A1 | 1/2009 |
| WO | 2009/021083 A1 | 2/2009 |
| WO | 2009/024824 A1 | 2/2009 |
| WO | 2009/027283 A1 | 3/2009 |
| WO | 2009/047514 A1 | 4/2009 |
| WO | 2009/068482 A1 | 6/2009 |
| WO | 2009/155121 A2 | 12/2009 |
| WO | 2010/042699 A1 | 4/2010 |
| WO | 2010/092015 A1 | 8/2010 |
| WO | 2010/092041 A1 | 8/2010 |
| WO | 2010/124826 A1 | 11/2010 |
| WO | 2011/013729 A1 | 2/2011 |
| WO | 2011/026579 A1 | 3/2011 |
| WO | 2011/063907 A1 | 6/2011 |
| WO | 2011/063908 A1 | 6/2011 |
| WO | 2011/064328 A1 | 6/2011 |
| WO | 2011/086098 A1 | 7/2011 |
| WO | 2011/086099 A1 | 7/2011 |
| WO | 2011/092272 A1 | 8/2011 |
| WO | 2012/032031 A1 | 3/2012 |
| WO | 2012/143329 A1 | 10/2012 |

(Continued)

OTHER PUBLICATIONS

Abrieu et al., "Mps1 Is a Kinetochore-Associated Kinase Essential for the Vertebrate Mitotic Checkpoint," Cell, Jul. 13, 2001, 106:83-93.

Berge et al., "Pharmaceutical Salts," Journal of Pharmaceutical Sciences, Jan. 1977, 66(1):1-19.

Dorer et al., "A Small-Molecule Inhibitor of Mps1 Blocks the Spindle-Checkpoint Responseto a Lack of Tension on Mitotic Chromosomes," Current Biology, Jun. 7, 2005, 15:1070-1076.

East et al., "DNA gyrase (GyrB)/topoisomerase IV (ParE) inhibitors: Synthesis and antibacterial activity," Bioorganic & Med. Chem. Letters, 2009, 19:894-899.

Fowler et al., "Selective Reduction of Radiotracer Trapping by Deuterium Substitution: Comparison of Carbon-II-L-Deprenyl and Carbon-11-Deprenyl-D2 for MAO B Mapping," The Journal of Nuclear Medicine, 36(7):1255-1262.

(Continued)

*Primary Examiner* — Nizal Chandrakumar
(74) *Attorney, Agent, or Firm* — Morrison & Foerster LLP

(57) ABSTRACT

The present invention relates to prodrug derivatives of Mps-1 kinase inhibitors, processes for their preparation, and their use for the treatment and/or prophylaxis of diseases.

14 Claims, No Drawings

(56) References Cited

FOREIGN PATENT DOCUMENTS

WO   2013/135612 A1   9/2013

OTHER PUBLICATIONS

Jelluma et al., "Chromosomal Instability by Inefficient Mps1 Auto-Activation Due to a Weakened Mitotic Checkpoint and Lagging Chromosomes," PloS ONE, Jun. 2008, 3(e2415):1-8.
Jones et al., "Chemical Genetics Reveals a Role for Mps1 Kinase in Kinetochore Attachment during Mitosis," Current Biology, Jan. 26, 2005, 15:160-165.
King, R., "When 2+2=5: The origins and fates of aneuploid and tetraploid cells," Biochimica et Biophysica Acta, 2008, 1786:4-14.
Kops et al., "On the Road to Cancer: Aneuploidy and the Mitotic Checkpoint," Nature Reviews/Cancer, Oct. 2005, 5:773-785.
Musacchio et al., "The spindle-assembly checkpoint in space and time," Nature Reviews/Molecular Cell Biology, May 2007, 8:379-393.
Schmidt et al., "Mitotic drug targets and the development of novel anti-mitotic anticancer drugs," Drug Resistance Updates, 2007, 10:162-181.
Schmidt et al., "Ablation of the spindle assembly checkpoint by a compound targeting Mps1," EMBO Reports, 2005, 6(9):866-872.
Schmidt et al., ""Exploiting the Compromised Spindle Assembly Checkpoint Functionof Tumor Cells,"" Cell Cycle, Jan. 2006, 5(2):159-163.
Suijkerbuijk et al., "Preventing aneuploidy: The contribution of mitotic checkpoint proteins," Biochimica et Biophysica Acta, 2008, 1786:24-31.
Weaver et al., "Aneuploidy: Instigator and Inhibitor of Tumorigenesis," Cancer Research, 2007, 67(21):10103-10105.
Yuan et al., "Increased Expression of Mitotic Checkpoint Genes in Breast Cancer Cells with Chromosomal Instability," Clinical Cancer Research, Jan. 15, 2006, 12(2):405-410.
Chemical Abstract XP-002574925.
Chemical Abstract XP-002574926.
Chemical Abstract XP-002574927.
Chemical Abstract XP-002574929.
Chemical Abstract XP-002574930.
Chemical Abstract XP-002574931.
Chemical Abstract XP-002574932.
Chemical Abstract XP-002574933.
Chemical Abstract XP-002574934.
Chemical Abstract XP-002574935.
Richardson et al., "Triazolo[1,5-a]pyrimidines as novel CDK2 inhibitors: Protein structure-guided design and SAR," Bioorganic & Medicinal Chemistry Letters, 2006, 16:1353-1357.
Zhao et al., "Synthesis and Anti-tumor Activities of Novel [1,2,4]triazolo[1,5-a]pyrimidines," Molecules, 2007, 12:1136-1146.
Related copending U.S. Appl. No. 13/512,721, filed Aug. 13, 2012,.
Related copending U.S. Appl. No. 13/704,859, filed Feb. 25, 2013.
Related copending U.S. Appl. No. 14/113,017, filed Jan. 6, 2014.
Related copending U.S. Appl. No. 14/362,836, filed Jun. 4, 2014.
National Cancer Institute, "Non-Small Cell Lung Cancer Treatment (PDQ®)—Patient Version," Updated May 12, 2015.
Stucke et al., "Human Mps1 kinase is required for the spindle assembly checkpoint but not for centrosome duplication," The EMBO Journal, 2002, 21(7):1723-1732.
Strickley, R.G., "Parenteral Formulations of Small Molecules Therapeutics Marketed in the United States (1999)—Part I," PDA Journal of Pharmaceutical Science & Technology, Aug. 14, 2014, 53(6):324-349.
Cross et al., "IUPAC Commission on Nomenclature of Organic Chemistry—Rules for the Nomenclature of Organic Chemistry," International Union of Pure and Applied Chemistry, 1976, 45(1-B):12-30.
Nema et al., "Excipients and Their Use in Injectable Products," PDA Journal of Pharmaceutical Science & Technology, Jul.-Aug. 1997, 51(4):166-171.
Powell et al., "Compendium of Excipients for Parenteral Formulations," PDA Journal of Pharmaceutical Science & Technology, Sep.-Oct. 1998, 52(5):238-311.
Rautio et al., "Prodrugs: design and clinical applications," Nature Reviews | Drug Discovery, Mar. 2008, 7:255-270.
SoftFocus Library SFK 39, BioFocus DPI, publicly available Sep. 20, 2005.

PRODRUG DERIVATIVES OF SUBSTITUTED TRIAZOLOPYRIDINES

The present invention relates to prodrug derivatives of Mps-1 kinase inhibitors, processes for their preparation, and their use for the treatment and/or prophylaxis of diseases.

BACKGROUND OF THE INVENTION

Mps-1 (Monopolar Spindle 1) kinase (also known as Tyrosine Threonine Kinase, TTK) is a dual specificity Ser/Thr kinase which plays a key role in the activation of the mitotic checkpoint (also known as spindle checkpoint, spindle assembly checkpoint) thereby ensuring proper chromosome segregation during mitosis [Abrieu A et al., Cell, 2001, 106, 83-93]. Every dividing cell has to ensure equal separation of the replicated chromosomes into the two daughter cells. Upon entry into mitosis, chromosomes are attached at their kinetochores to the microtubules of the spindle apparatus. The mitotic checkpoint is a surveillance mechanism that is active as long as unattached kinetochores are present and prevents mitotic cells from entering anaphase and thereby completing cell division with unattached chromosomes [Suijkerbuijk S J and Kops G J, Biochemica et Biophysica Acta, 2008, 1786, 24-31; Musacchio A and Salmon E D, Nat Rev Mol Cell Biol., 2007, 8, 379-93]. Once all kinetochores are attached in a correct amphitelic, i.e. bipolar, fashion with the mitotic spindle, the checkpoint is satisfied and the cell enters anaphase and proceeds through mitosis. The mitotic checkpoint consists of a complex network of a number of essential proteins, including members of the MAD (mitotic arrest deficient, MAD 1-3) and Bub (Budding uninhibited by benzimidazole, Bub 1-3) families, the motor protein CENP-E, Mps-1 kinase as well as other components, many of these being over-expressed in proliferating cells (e.g. cancer cells) and tissues [Yuan B et al., Clinical Cancer Research, 2006, 12, 405-10]. The essential role of Mps-1 kinase activity in mitotic checkpoint signalling has been shown by shRNA-silencing, chemical genetics as well as chemical inhibitors of Mps-1 kinase [Jelluma N et al., PLos ONE, 2008, 3, e2415; Jones M H et al., Current Biology, 2005, 15, 160-65; Dorer R K et al., Current Biology, 2005, 15, 1070-76; Schmidt M et al., EMBO Reports, 2005, 6, 866-72].

There is ample evidence linking reduced but incomplete mitotic checkpoint function with aneuploidy and tumorigenesis [Weaver B A and Cleveland D W, Cancer Research, 2007, 67, 10103-5; King R W, Biochimica et Biophysica Acta, 2008, 1786, 4-14]. In contrast, complete inhibition of the mitotic checkpoint has been recognised to result in severe chromosome missegregation and induction of apoptosis in tumour cells [Kops G J et al., Nature Reviews Cancer, 2005, 5, 773-85; Schmidt M and Medema R H, Cell Cycle, 2006, 5, 159-63; Schmidt M and Bastians H, Drug Resistance Updates, 2007, 10, 162-81].

Therefore, mitotic checkpoint abrogation through pharmacological inhibition of Mps-1 kinase or other components of the mitotic checkpoint represents a new approach for the treatment of proliferative disorders including solid tumours such as carcinomas and sarcomas and leukaemias and lymphoid malignancies or other disorders associated with uncontrolled cellular proliferation.

Different compounds have been disclosed in prior art which show an inhibitory effect on Mps-1 kinase: WO 2009/024824 A1 discloses 2-Anilinopurin-8-ones as inhibitors of Mps-1 for the treatment of proliferate disorders. WO 2010/124826 A1 discloses substituted imidazoquinoxaline compounds as inhibitors of Mps-1 kinase. WO 2011/026579 A1 discloses substituted aminoquinoxalines as Mps-1 inhibitors. WO 2011/064328 A1, WO 2011/063907 A1, WO 2011/063908 A1, and WO 2012/143329 A1 relate to [1,2,4]-triazolo-[1,5-α]-pyridines and their use for inhibition of Mps-1 kinase.

The above mentioned patent applications which are related to [1,2,4]-triazolo-[1,5-α]-pyridines mainly focus on the effectiveness of the compounds in inhibiting Mps-1 kinase, expressed by the half maximal inhibitory concentration ($IC_{50}$) of the compounds. For example, in WO 2011/063908 A1 the effectiveness in inhibiting Mps-1 kinase was measured in an Mps-1 kinase assay with a concentration of 10 µM adenosine triphosphate (ATP). The cellular concentration of ATP in mammals is in the millimolar range. Therefore it is important that a drug substance is also effective in inhibiting Mps-1 kinase in a kinase assay with a concentration of ATP in the millimolar range, e.g. 2 mM ATP, in order to potentially achieve an antiproliferative effect in a cellular assay.

In addition, as one of ordinary skill in the art knows, there a many more factors determining the druglikeness of a compound. The objective of a pre-clinical development is to assess e.g. safety, toxicity, pharmacokinetics and metabolism parameters prior to human clinical trials. One important factor for assessing the druglikeness of a compound is the metabolic stability. The metabolic stability of a compound can be determined e.g. by incubating the compound with a suspension of liver microsomes from e.g. a rat, a dog and/or a human (for details see experimental section).

Another important factor for assessing the druglikeness of a compound for the treatment of cancer is the inhibition of cell proliferation which can be determined e.g. in a HeLa cell proliferation assay (for details see experimental section).

The successful delivery of a pharmaceutical to a patient is of critical importance in the treatment of disorders as well. The use of many clinical drugs with known bioactive properties is limited by the drugs' very low water solubility, making for example intravenous administration of the active ingredient difficult.

Intravenous (i.v.) medication administration refers to the process of giving medication directly into a patient's vein. Methods of administering i.v. medication may include giving the medication by rapid injection (push) into the vein using a syringe, giving the medication intermittently over a specific amount of time using an i.v. secondary line, or giving the medication continuously mixed in the main i.v. solution.

The primary purpose of giving i.v. medications is to initiate a rapid systemic response to medication. It is one of the fastest ways to deliver medication. The drug is immediately available to the body. It is easier to control the actual amount of drug delivered to the body by using the i.v. method and it is also easier to maintain drug levels in the blood for therapeutic response.

As a result of low water solubility, many drugs often are formulated in co-solvent pharmaceutical vehicles or as prodrugs.

A prodrug is an active drug chemically transformed into a derivative which by virtue of chemical or enzymatic attack is converted to the parent drug within the body before or after reaching the site of action. The process of converting an active drug into inactive form is called drug latentiation. Prodrugs can be carrier-linked-prodrugs and bioprecursors. The carrier-linked prodrug results from a temporary linkage of the active molecule with a transport moiety. Such prodrugs are less active or inactive compared to the parent active drug. The transport moiety will be chosen for its non-toxicity and its ability to ensure the release of the active principle with efficient kinetics. Whereas the bioprecursors result from a molecular modification of the active principle itself by generation of a new molecule that is capable of being a substrate to the metabolizing enzymes releasing the active principle as a metabolite.

Prodrugs are prepared to alter the drug pharmacokinetics, improve stability and solubility, decrease toxicity, increase specificity, and/or increase duration of the pharmacological effect of the drug. By altering pharmacokinetics the drug bioavailability is increased by increasing absorption, distribution, biotransformation, and/or excretion of the drug.

In designing the prodrugs, it is important to consider the following factors: a) the linkage between the carrier and the drug is usually a covalent bond, b) the prodrug is inactive or less active than the active principle, c) the prodrug synthesis should not be expensive, d) the prodrug has to be reversible or bioreversible derivative of the drug, and e) the carrier moiety must be non-toxic and inactive when released.

Prodrugs are usually prepared by: a) formation of ester, hemiesters, carbonate esters, nitrate esters, amides, hydroxamic acids, carbamates, imines, mannich bases, and enamines of the active drug, b) functionalizing the drug with azo, glycoside, peptide, and ether functional groups, c) use of polymers, salts, complexes, phosphoramides, acetals, hemiacetals, and ketal forms of the drug (for example, see Andrejus Korolkovas's, "Essentials of Medicinal Chemistry", pp. 97-118).

It was therefore an object of the present invention to identify an Mps-1 kinase inhibiting compound or a prodrug derivative thereof which is characterized by a high drug-likeness and which can be administered intravenously.

SUMMARY OF THE INVENTION

The present invention relates to compounds of general formula (I):

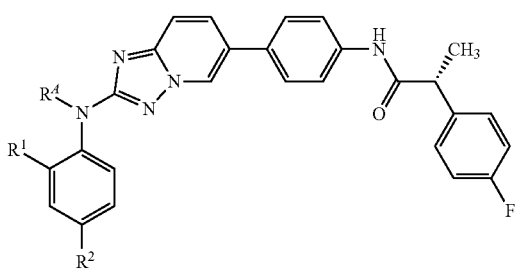

(I)

in which:
$R^A$ represents a group selected from:
  —C(=O)—(CH$_2$)$_3$—N(H)R$^3$,
  —C(=O)—(CR$^4$R$^5$)—N(R$^6$)R$^7$,
  —C(=O)—O—(CH$_2$)$_2$—N(H)R$^3$,
  —C(=O)—O—(CR$^4$R$^5$)—O—P(=O)(OH)$_2$,
  —C(=O)—O—(CR$^4$R$^5$)—O—C(=O)—R$^8$,
  —C(=O)—O—(CR$^4$R$^5$)—O—C(=O)—CH(R$^6$)—NH—C(=O)—R$^9$;
$R^1$ represents a group selected from methoxy- and 2,2,2-trifluoroethoxy-;

$R^2$ represents a group selected from:

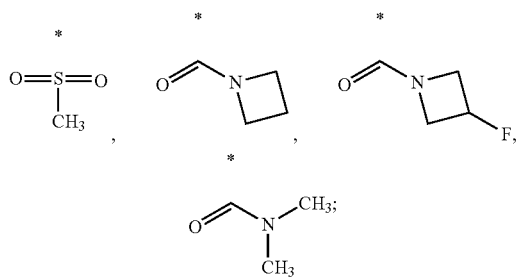

wherein "*" indicates the point of attachment to the phenyl ring $R^2$ is attached to;
$R^3$ represents a group selected from:
  C$_1$-C$_6$-alkyl, C$_3$-C$_6$-cycloalkyl-,
  4- to 7-membered heterocycloalkyl-;
  said group being optionally substituted, one or more times, identically or differently, with a group selected from:
  —OH, —NH$_2$, —N(H)R$^{10}$, —N(R$^{10}$)R$^{11}$, —O—P(=O)(OH)$_2$;
$R^4$ and $R^5$, independently from each other, represent a group selected from a hydrogen atom and a C$_1$-C$_3$-alkyl- group, or
$R^4$ and $R^5$, together with the carbon atom to which they are attached, form a C$_3$-C$_6$-cycloalkyl ring;
$R^6$ represents a hydrogen atom or a C$_1$-C$_3$-alkyl- group;
$R^7$ represents a hydrogen atom or a group —C(=O)R$^9$;
$R^8$ represents a group selected from:
  C$_1$-C$_6$-alkyl, C$_3$-C$_6$-cycloalkyl-,
  4- to 7-membered heterocycloalkyl-;
  said group being optionally substituted, one or more times, identically or differently, with a group selected from:
  —OH, —NH$_2$, —N(H)R$^{10}$, —N(R$^{10}$)R$^{11}$, —O—P(=O)(OH)$_2$;
$R^9$ represents a group

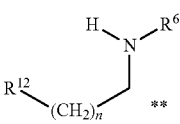

or $R^9$ represents a group selected from:

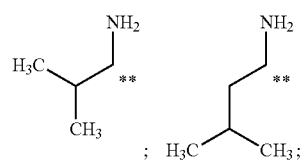

wherein "**" indicates the point of attachment to the carbonyl group $R^9$ is attached to;
$R^{10}$ and $R^{11}$, independently from each other, represent a group selected from a hydrogen atom and a C$_1$-C$_3$-alkyl- group, or
$R^{10}$ and $R^{11}$, together with the nitrogen atom to which they are attached form a 4- to 7-membered heterocycloalkyl ring;
$R^{12}$ represents a group selected from a hydrogen atom, —OH, —NR$^{10}$R$^{11}$, —NH—C(=NH)—NH$_2$;

n is an integer of 0, 1, 2, 3 or 4;
or a tautomer, an N-oxide, a hydrate, a solvate, or a salt thereof, or a mixture of same.

DETAILED DESCRIPTION OF THE INVENTION

The terms as mentioned in the present text have preferably the following meanings:

The term "halogen atom" or "halo-" is to be understood as meaning a fluorine, chlorine, bromine or iodine atom.

The term "$C_1$-$C_6$-alkyl" is to be understood as preferably meaning a linear or branched, saturated, monovalent hydrocarbon group having 1, 2, 3, 4, 5 or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.

The term "$C_1$-$C_6$-alkylene" is to be understood as preferably meaning a linear or branched, saturated, bivalent hydrocarbon group having 1, 2, 3, 4, 5 or 6 carbon atoms, e.g. a methylene, ethylene, propylene, butylene, pentylene, hexylene, iso-propylene, iso-butylene, sec-butylene, tert-butylene, iso-pentylene, 2-methylbutylene, 1-methylbutylene, 1-ethylpropylene, 1,2-dimethylpropylene, neo-pentylene, 1,1-dimethylpropylene, 4-methylpentylene, 3-methylpentylene, 2-methylpentylene, 1-methylpentylene, 2-ethylbutylene, 1-ethylbutylene, 3,3-dimethylbutylene, 2,2-dimethylbutylene, 1,1-dimethylbutylene, 2,3-dimethylbutylene, 1,3-dimethylbutylene, or 1,2-dimethylbutylene group, or an isomer thereof. Particularly, said group has 2, 3, 4, 5 or 6 carbon atoms ("$C_2$-$C_6$-alkylene"), e.g. a methylene, ethylene, propylene, butylene, iso-propylene, iso-butylene, sec-butylene, tert-butylene group, more particularly 2, 3 or 4 carbon atoms ("$C_2$-$C_4$-alkylene"), e.g. an ethylene, propylene-, iso-propylene, butylene, or iso-butylene group.

The term "halo-$C_1$-$C_6$-alkyl" is to be understood as preferably meaning a linear or branched, saturated, monovalent hydrocarbon group in which the term "$C_1$-$C_6$-alkyl" is defined supra, and in which one or more of the hydrogen atoms is replaced, in identically or differently, by a halogen atom. Particularly, said halogen atom is F. Said halo-$C_1$-$C_6$-alkyl group is, for example, —$CF_3$, —$CHF_2$, —$CH_2F$, —$CF_2CF_3$, or —$CH_2CF_3$.

The term "$C_1$-$C_6$-alkoxy" is to be understood as preferably meaning a linear or branched, saturated, monovalent group of formula —O—($C_1$-$C_6$-alkyl), in which the term "$C_1$-$C_6$-alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "halo-$C_1$-$C_6$-alkoxy" is to be understood as preferably meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said halo-$C_1$-$C_6$-alkoxy group is, for example, —$OCF_3$, —$OCHF_2$, —$OCH_2F$, —$OCF_2CF_3$, or —$OCH_2CF_3$.

The term "$C_1$-$C_6$-alkoxy-$C_1$-$C_6$-alkyl" is to be understood as preferably meaning a linear or branched, saturated, monovalent $C_1$-$C_6$-alkyl group, as defined supra, in which one or more of the hydrogen atoms is replaced, in identically or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, or an isomer thereof.

The term "halo-$C_1$-$C_6$-alkoxy-$C_1$-$C_6$-alkyl" is to be understood as preferably meaning a linear or branched, saturated, monovalent $C_1$-$C_6$-alkoxy-$C_1$-$C_6$-alkyl group, as defined supra, in which one or more of the hydrogen atoms is replaced, in identically or differently, by a halogen atom. Particularly, said halogen atom is F. Said halo-$C_1$-$C_6$-alkoxy-$C_1$-$C_6$-alkyl group is, for example, $CH_2CH_2OCF_3$, —$CH_2CH_2OCHF_2$, —$CH_2CH_2OCH_2F$, —$CH_2CH_2OCF_2CF_3$, or $CH_2CH_2OCH_2CF_3$.

The term "$C_2$-$C_6$-alkenyl" is to be understood as preferably meaning a linear or branched, monovalent hydrocarbon group, which contains one or more double bonds, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, iso-propenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1- enyl, (Z)-1-isopropylprop-1-enyl, (E)-3,3-dimethylprop-1-enyl, (Z)-3,3-dimethylprop-1-enyl, 1-(1,1-dimethylethyl) ethenyl, buta-1,3-dienyl, penta-1,4-dienyl, hexa-1,5-dienyl, or methylhexadienyl group. Particularly, said group is vinyl or allyl.

The term "$C_2$-$C_6$-alkynyl" is to be understood as preferably meaning a linear or branched, monovalent hydrocarbon group which contains one or more triple bonds, and which contains 2, 3, 4, 5 or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl, or 3,3-dimethylbut-1-ynyl group. Particularly, said alkynyl group is ethynyl, prop-1-ynyl, or prop-2-ynyl.

The term "$C_3$-$C_7$-cycloalkyl" is to be understood as meaning a saturated, monovalent, monocyclic hydrocarbon ring which contains 3, 4, 5, 6 or 7 carbon atoms. Said $C_3$-$C_7$-cycloalkyl group is for example a cyclopropyl, cyclobutyl, cyclopentyl, cyclohexyl or cycloheptyl ring. Particularly, said ring contains 3, 4, 5 or 6 carbon atoms ("$C_3$-$C_6$-cycloalkyl").

The term "$C_4$-$C_8$-cycloalkenyl" is to be understood as preferably meaning a monovalent, monocyclic hydrocarbon ring which contains 4, 5, 6, 7 or 8 carbon atoms and one or two double bonds, in conjugation or not, as the size of said cycloalkenyl ring allows. Particularly, said ring contains 4, 5 or 6 carbon atoms ("$C_4$-$C_6$-cycloalkenyl"). Said $C_4$-$C_8$-cycloalkenyl group is for example a cyclobutenyl, cyclopentenyl, or cyclohexenyl group.

The term "3- to 10-membered heterocycloalkyl", is to be understood as meaning a saturated, monovalent, mono- or bicyclic hydrocarbon ring which contains 2, 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom, or a $C_1$-$C_6$-alkyl- group; it being possible for said heterocycloalkyl group to be attached to the rest of the molecule via any one of the carbon atoms or, if present, the nitrogen atom.

Particularly, said 3- to 10-membered heterocycloalkyl can contain 2, 3, 4, 5 or 6 carbon atoms, and one or more of the above-mentioned heteroatom-containing groups (a "3- to 7-membered heterocycloalkyl"), more particularly said heterocycloalkyl can contain 4, 5 or 6 carbon atoms, and one or more of the above-mentioned heteroatom-containing groups (a "4- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example.

The term "4- to 10-membered heterocycloalkenyl", is to be understood as meaning an unsaturated, monovalent, mono- or bicyclic hydrocarbon ring which contains 3, 4, 5, 6, 7, 8 or 9 carbon atoms, and one or more heteroatom-containing groups selected from C(=O), 0, S, S(=O), S(=O)$_2$, NR$^a$, in which R$^a$ represents a hydrogen atom or a $C_1$-$C_6$-alkyl- group; it being possible for said heterocycloalkenyl group to be attached to the rest of the molecule via any one of the carbon atoms or, if present, the nitrogen atom. Examples of said heterocycloalkenyl may contain one or more double bonds, e.g. 4H-pyranyl, 2H-pyranyl, 3H-diazirinyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl, or 4H-[1,4]thiazinyl group.

The term "aryl" is to be understood as preferably meaning a monovalent, aromatic, mono-, or bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group; or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a biphenyl group (a "$C_{12}$-aryl" group), or a ring having 13 carbon atoms, (a "$C_{13}$-aryl" group), e.g. a fluorenyl group, or a ring having 14 carbon atoms, (a "$C_{14}$-aryl" group), e.g. an anthracenyl group. Preferably, the aryl group is a phenyl group.

The term "heteroaryl" is understood as preferably meaning a monovalent, monocyclic-, bicyclic- or tricyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridinyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridyl includes pyridin-2-yl, pyridin-3-yl, and pyridin-4-yl; or the term thienyl includes thien-2-yl and thien-3-yl. Preferably, the heteroaryl group is a pyridinyl group.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_7$", as used throughout this text, e.g. in the context of the definition of "$C_3$-$C_7$-cycloalkyl", is to be understood as meaning a cycloalkyl group having a finite number of carbon atoms of 3 to 7, i.e. 3, 4, 5, 6 or 7 carbon atoms. It is to be understood further that said term "$C_3$-$C_7$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_7$; particularly $C_3$-$C_6$.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitrobenzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

As used herein, the term "$PG^1$" refers to a protecting group for hydroxy groups e.g. a TMS group or TBDPS group as decribed for example in T. W. Greene and P. G. M. Wuts in *Protective Groups in Organic Synthesis*, $3^{rd}$ edition, Wiley 1999 (TMS=trimethylsilyl, TBDPS=tert-butyldiphenylsilyl).

As used herein, the term "$PG^2$" refers to a protecting group for amino groups e.g. a Boc group as descibed for example in T. W. Greene and P. G. M. Wuts in *Protective Groups in Organic Synthesis*, $3^{rd}$ edition, Wiley 1999 (Boc=tert-butyloxycarbonyl).

As used herein, the term "one or more times", e.g. in the definition of the substituents of the compounds of the general formulae of the present invention, is understood as meaning "one, two, three, four or five times, particularly one, two, three or four times, more particularly one, two or three times, even more particularly one or two times".

Compounds A1, A2, A3, A4, and A5, as defined in the Experimental Section, are very effective Mps-1 inhibitors. Surprisingly it was found, that these compounds are characterized by:
  an $IC_{50}$ lower than or equal to 1 nM (more potent than 1 nM) in an Mps-1 kinase assay with a concentration of 10 µM ATP, and
  an $IC_{50}$ lower than 2 nM (more potent than 2 nM) in an Mps-1 kinase assay with a concentration of 2 mM ATP, and
  a maximum oral bioavailability ($F_{max}$) in rat that is higher than 70% determined by means of rat liver microsomes as described below, and
  a maximum oral bioavailability ($F_{max}$) in dog that is higher than 50% determined by means of dog liver microsomes as described below, and
  a maximum oral bioavailability ($F_{max}$) in human that is higher than 60%, determined by means of human liver microsomes as described below, and
  an $IC_{50}$ lower than 400 nM in a HeLa cell proliferation assay as described below.

However, these compounds have only limited solubility in water and physiological media, making intravenous administration difficult.

In accordance with a first aspect, the present invention relates to prodrug derivates which show a higher solubility in water and physiological media than the compounds A1, A2, A3, A4, and A5, making them suitable for therapeutic use, especially on intravenous administration.

The prodrug derivatives are defined by general formula (I)

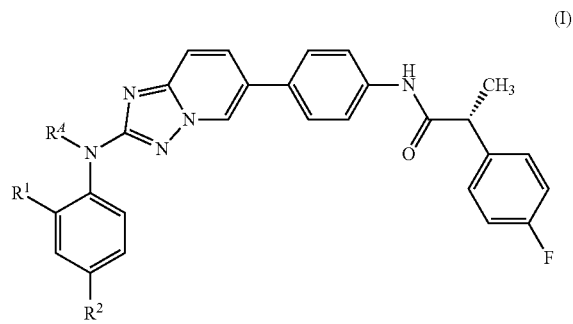

(I)

in which:
$R^4$ represents a group selected from:
  —C(=O)—(CH$_2$)$_3$—N(H)R$^3$,
  —C(=O)—(CR$^4$R$^5$)—N(R$^6$)R$^7$,
  —C(=O)—O—(CH$_2$)$_2$—N(H)R$^3$,
  —C(=O)—O—(CR$^4$R$^5$)—O—P(=O)(OH)$_2$,
  —C(=O)—O—(CR$^4$R$^5$)—O—C(=O)—R$^8$,
  —C(=O)—O—(CR$^4$R$^5$)—O—C(=O)—CH(R$^6$)—NH—C(=O)—R$^9$;
$R^1$ represents a group selected from methoxy- and 2,2,2-trifluoroethoxy-;
$R^2$ represents a group selected from:

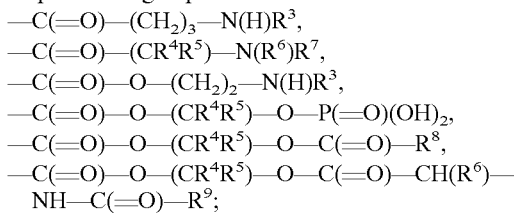

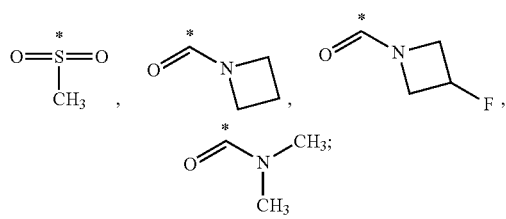

wherein "*" indicates the point of attachment to the phenyl ring $R^2$ is attached to;
$R^3$ represents a group selected from:
  $C_1$-$C_6$-alkyl, $C_3$-$C_6$-cycloalkyl-,
  4- to 7-membered heterocycloalkyl-;
  said group being optionally substituted, one or more times, identically or differently, with a group selected from:
  —OH, —NH$_2$, —N(H)R$^{10}$, —N(R$^{10}$)R$^{11}$, —O—P(=O)(OH)$_2$;
$R^4$ and $R^5$, independently from each other, represent a group selected from a hydrogen atom and a $C_1$-$C_3$-alkyl- group, or
$R^4$ and $R^5$, together with the carbon atom to which they are attached, form a $C_3$-$C_6$-cycloalkyl ring;
$R^6$ represents a hydrogen atom or a $C_1$-$C_3$-alkyl- group;

$R^7$ represents a hydrogen atom or a group —C(=O)$R^9$;
$R^8$ represents a group selected from:
C$_1$-C$_6$-alkyl, C$_3$-C$_6$-cycloalkyl-,
4- to 7-membered heterocycloalkyl-;
said group being optionally substituted, one or more times, identically or differently, with a group selected from:
—OH, —NH$_2$, —N(H)$R^{10}$, —N($R^{10}$)$R^{11}$, —O—P(=O)(OH)$_2$;
$R^9$ represents a group

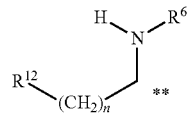

or $R^9$ represents a group selected from:

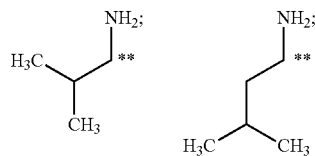

wherein "**" indicates the point of attachment to the carbonyl group $R^9$ is attached to;
$R^{10}$ and $R^{11}$, independently from each other, represent a group selected from a hydrogen atom and a C$_1$-C$_3$-alkyl-group, or
$R^{10}$ and $R^{11}$, together with the nitrogen atom to which they are attached form a 4- to 7-membered heterocycloalkyl ring;
$R^{12}$ represents a group selected from a hydrogen atom, —OH, —N$R^{10}R^{11}$, —NH—C(=NH)—NH$_2$;
n is an integer of 0, 1, 2, 3 or 4;
or a tautomer, an N-oxide, a hydrate, a solvate, or a salt thereof, or a mixture of same.

In a preferred embodiment,
$R^A$ represents a group selected from:
—C(=O)—(CH$_2$)$_3$—N(H)$R^3$,
—C(=O)—O—(CH$_2$)$_2$—N(H)$R^3$,
—C(=O)—(CR$^4R^5$)—O—P(=O)(OH)$_2$,
—C(=O)—O—(CR$^4R^5$)—O—C(=O)—$R^8$,
—C(=O)—O—(CR$^4R^5$)—O—C(=O)—CH($R^6$)—NH—C(=O)—$R^9$.

In another preferred embodiment, $R^A$ represents a group selected from
—C(=O)—(CH$_2$)$_3$—N(H)$R^3$,
—C(=O)—O—(CR$^4R^5$)—O—P(=O)(OH)$_2$,
—C(=O)—O—(CR$^4R^5$)—O—C(=O)—$R^8$,
—C(=O)—O—(CR$^4R^5$)—O—C(=O)—CH($R^6$)—NH—C(=O)—$R^9$.

In another preferred embodiment, $R^A$ represents a group selected from
—C(=O)—O—(CR$^4R^5$)—O—P(=O)(OH)$_2$,
—C(=O)—O—(CR$^4R^5$)—O—C(=O)—$R^8$,
—C(=O)—O—(CR$^4R^5$)—O—C(=O)—CH($R^6$)—NH—C(=O)—$R^9$.

In another preferred embodiment, $R^A$ represents a group selected from
—C(=O)—O—(CR$^4R^5$)—O—C(=O)—$R^8$,
—C(=O)—O—(CR$^4R^5$)—O—C(=O)—CH($R^6$)—NH—C(=O)—$R^9$.

In another preferred embodiment, $R^A$ represents a group selected from
—C(=O)—(CH$_2$)$_3$—N(H)$R^3$,
—C(=O)—(CR$^4R^5$)—N($R^6$)$R^7$.

In another preferred embodiment, $R^A$ represents a group selected from
—C(=O)—(CH$_2$)$_3$—N(H)$R^3$,
—C(=O)—O—(CH$_2$)$_2$—N(H)$R^3$.

In another preferred embodiment, $R^A$ represents a group selected from
—C(=O)—(CR$^4R^5$)—N($R^6$)$R^7$,
—C(=O)—O—(CR$^4R^5$)—O—C(=O)—CH($R^6$)—NH—C(=O)—$R^9$.

In another preferred embodiment, $R^A$ represents a —C(=O)—(CH$_2$)$_3$—N(H)$R^3$ group.

In another preferred embodiment, $R^A$ represents a —C(=O)—(CR$^4R^5$)—N($R^6$)$R^7$ group.

In another preferred embodiment, $R^A$ represents a —C(=O)—O—(CH$_2$)$_2$—N(H)$R^3$ group.

In another preferred embodiment, $R^A$ represents a —C(=O)—O—(CR$^4R^5$)—O—P(=O)(OH)$_2$ group.

In another preferred embodiment, $R^A$ represents a —C(=O)—O—(CR$^4R^5$)—O—C(=O)—$R^8$ group.

In another preferred embodiment, $R^A$ represents a —C(=O)—O—(CR$^4R^5$)—O—C(=O)—CH($R^6$)—NH—C(=O)—$R^9$ group.

In another preferred embodiment, $R^1$ represents a group selected from methoxy- and 2,2,2-trifluoroethoxy-.

In another preferred embodiment, $R^1$ represents a 2,2,2-trifluoroethoxy- group.

In a more preferred embodiment, $R^1$ represents a methoxy- group.

In another preferred embodiment, $R^2$ represents a group selected from:

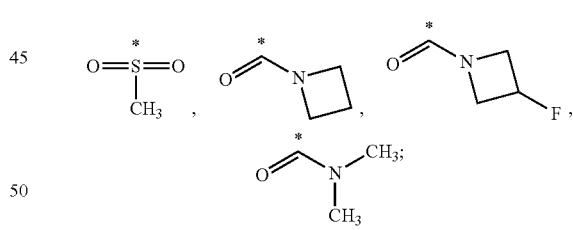

wherein "*" indicates the point of attachment to the phenyl ring $R^2$ is attached to.

In another preferred embodiment, $R^2$ represents a group selected from

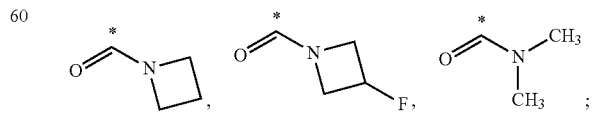

wherein "*" indicates the point of attachment to the phenyl ring $R^2$ is attached to.

In another preferred embodiment, $R^2$ represents a group selected from

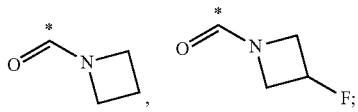

wherein "*" indicates the point of attachment to the phenyl ring $R^2$ is attached to.

In another preferred embodiment, $R^2$ represents

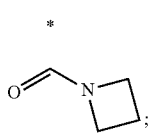

wherein "*" indicates the point of attachment to the phenyl ring $R^2$ is attached to.

In another preferred embodiment, $R^2$ represents

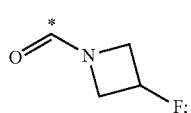

wherein "*" indicates the point of attachment to the phenyl ring $R^2$ is attached to.

In another preferred embodiment, $R^2$ represents

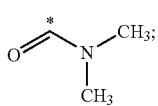

wherein "*" indicates the point of attachment to the phenyl ring $R^2$ is attached to.

In a particularly preferred embodiment, $R^2$ represents a $-S(=O)_2CH_3$ group.

In another embodiment, $R^3$ represents a group selected from:
$C_1$-$C_6$-alkyl, $C_3$-$C_6$-cycloalkyl-, 4- to 7-membered heterocycloalkyl-;
said group being optionally substituted, one or more times, identically or differently, with a group selected from:
—OH, —$NH_2$, —N(H)$R^{10}$, —N($R^{10}$)$R^{11}$, —O—P(=O)(OH)$_2$.

In a preferred embodiment, $R^3$ represents a $C_1$-$C_6$-alkyl group, said group being optionally substituted, one or more times, identically or differently, with a group selected from:
—OH, —$NH_2$, —N(H)$R^{10}$, —N($R^{10}$)$R^{11}$, —O—P(=O)(OH)$_2$.

In another preferred embodiment, $R^3$ represents a $C_3$-$C_6$-cycloalkyl- group, said group being optionally substituted, one or more times, identically or differently, with a group selected from:
—OH, —$NH_2$, —N(H)$R^{10}$, —N($R^{10}$)$R^{11}$, —O—P(=O)(OH)$_2$.

In another preferred embodiment, $R^3$ represents a 4- to 7-membered heterocycloalkyl- group, said group being optionally substituted, one or more times, identically or differently, with a group selected from:
—OH, —$NH_2$, —N(H)$R^{10}$, —N($R^{10}$)$R^{11}$, —O—P(=O)(OH)$_2$.

In another preferred embodiment, $R^3$ represents a $C_1$-$C_3$-alkyl- group.

In another preferred embodiment, $R^3$ represents a $C_1$-$C_2$-alkyl- group.

In another preferred embodiment, $R^3$ represents an ethyl- group.

In a particularly preferred embodiment, $R^3$ represents a methyl- group.

In another embodiment, $R^4$ and $R^5$, independently from each other, represent a group selected from a hydrogen atom and a $C_1$-$C_3$-alkyl- group, or $R^4$ and $R^5$, together with the carbon atom to which they are attached, form a $C_3$-$C_6$-cycloalkyl ring.

In another embodiment, $R^4$ and $R^5$, independently from each other, represent a group selected from a hydrogen atom and a $C_1$-$C_3$-alkyl- group.

In another embodiment, $R^4$ and $R^5$, together with the carbon atom to which they are attached, form a $C_3$-$C_6$-cycloalkyl ring.

In a preferred embodiment, $R^4$ represents a hydrogen atom or a $C_1$-$C_3$-alkyl- group, and $R^5$ represents a hydrogen atom.

In another preferred embodiment, $R^4$ represents a hydrogen atom or a methyl- or iso-propyl- group, and $R^5$ represents a hydrogen atom.

In another preferred embodiment, $R^4$ and $R^5$ each represent a hydrogen atom.

In a particularly preferred embodiment, $R^4$ represents a methyl- group, and $R^5$ represents a hydrogen atom.

In another particularly preferred embodiment, $R^4$ represents an iso-propyl- group, and $R^5$ represents a hydrogen atom.

In a preferred embodiment, $R^4$ represents a hydrogen atom or a $C_1$-$C_3$-alkyl- group.

In a particularly preferred embodiment, $R^4$ represents a hydrogen atom or a methyl- group.

In another particularly preferred embodiment, $R^4$ represents a hydrogen atom.

In another particularly preferred embodiment, $R^4$ represents a methyl- group.

In another preferred embodiment, $R^5$ represents a hydrogen atom.

In another embodiment, $R^6$ represents a hydrogen atom or a $C_1$-$C_3$-alkyl- group.

In a preferred embodiment, $R^6$ represents a hydrogen atom or a methyl- group.

In another preferred embodiment, $R^6$ represents a hydrogen atom.

In a particularly preferred embodiment, $R^6$ represents a methyl- group.

In another embodiment, $R^7$ represents a hydrogen atom or a group —C(=O)$R^9$.

In a preferred embodiment, $R^7$ represents a group —C(=O)$R^9$.

In another preferred embodiment, $R^7$ represents a hydrogen atom.

In another embodiment, $R^8$ represents a group selected from:
$C_1$-$C_6$-alkyl, $C_3$-$C_6$-cycloalkyl-,
4- to 7-membered heterocycloalkyl-;
said group being optionally substituted, one or more times, identically or differently, with a group selected from:

—OH, —NH$_2$, —N(H)R$^{10}$, —N(R$^{10}$)R$^{11}$, —O—P(=O)(OH)$_2$.

In a preferred embodiment, R$^8$ represents a C$_1$-C$_6$-alkyl group, said group being optionally substituted, one or more times, identically or differently, with a group selected from:
—OH, —NH$_2$, —N(H)R$^{10}$, —N(R$^{10}$)R$^{11}$, —O—P(=O)(OH)$_2$.

In another preferred embodiment, R$^8$ represents a C$_3$-C$_6$-cycloalkyl- group, said group being optionally substituted, one or more times, identically or differently, with a group selected from:
—OH, —NH$_2$, —N(H)R$^{10}$, —N(R$^{10}$)R$^{11}$, —O—P(=O)(OH)$_2$.

In another preferred embodiment, R$^8$ represents a 4- to 7-membered heterocycloalkyl- group, said group being optionally substituted, one or more times, identically or differently, with a group selected from:
—OH, —NH$_2$, —N(H)R$^{10}$, —N(R$^{10}$)R$^{11}$, —O—P(=O)(OH)$_2$.

In another preferred embodiment, R$^8$ represents a group selected from:
- C$_1$-C$_6$-alkyl, substituted one or more times, identically or differently, with a group selected from: —NH$_2$, —N(H)R$^{10}$, —N(R$^{10}$)R$^{11}$,
- 4- to 7-membered heterocycloalkyl-, optionally substituted, one or more times, identically or differently, with a group selected from:
—NH$_2$, —N(H)R$^{10}$, —N(R$^{10}$)R$^{11}$.

In another preferred embodiment, R$^8$ represents a C$_1$-C$_6$-alkyl group, substituted one or more times, identically or differently, with a group selected from: —NH$_2$, —N(H)R$^{10}$, —N(R$^{10}$)R$^{11}$.

In another preferred embodiment, R$^8$ represents a 4- to 7-membered heterocycloalkyl- group, optionally substituted, one or more times, identically or differently, with a group selected from: —NH$_2$, —N(H)R$^{10}$, —N(R$^{10}$)R$^{11}$.

In another preferred embodiment, R$^8$ represents a group selected from:
- C$_1$-C$_6$-alkyl, substituted one or more times, identically or differently, with a group selected from —NH$_2$, —N(H)R$^{10}$, —N(R$^{10}$)R$^{11}$,
- a heterocycloalkyl group selected from pyrrolidinyl-, piperidinyl-, morpholinyl-, and piperazinyl-.

In another preferred embodiment, R$^8$ represents a heterocycloalkyl group selected from pyrrolidinyl-, piperidinyl-, morpholinyl-, and piperazinyl-.

In a particularly preferred embodiment, R$^8$ represents a heterocycloalkyl group selected from:

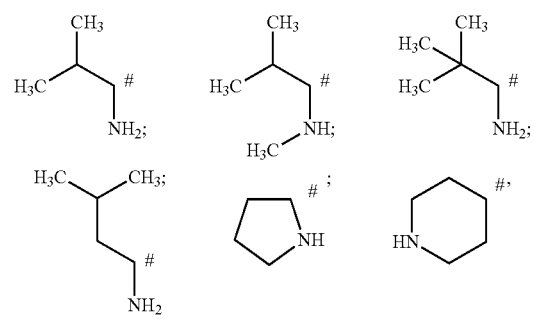

wherein "#" represents the point of attachment to the carbonyl group R$^8$ is attached to.

In another particularly preferred embodiment, R$^8$ represents a heterocycloalkyl group selected from:

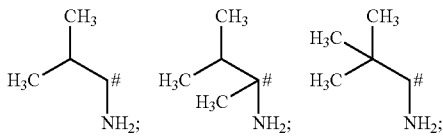

wherein "#" represents the point of attachment to the carbonyl group R$^8$ is attached to.

In a preferred embodiment, R$^9$ represents

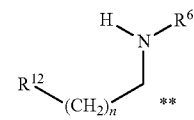

wherein "**" indicates the point of attachment to the carbonyl group R$^9$ is attached to.

In another preferred embodiment, R$^9$ represents a group selected from:

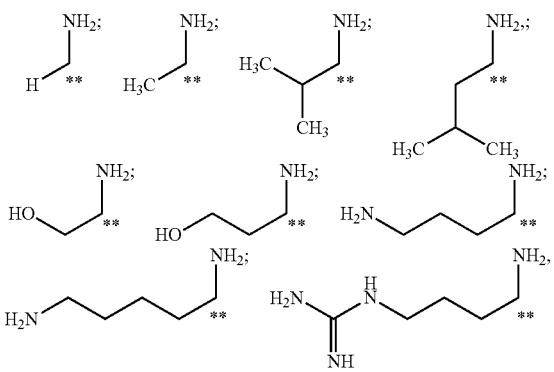

wherein "**" indicates the point of attachment to the carbonyl group R$^9$ is attached to.

In another preferred embodiment, R$^9$ represents a group selected from:

wherein "**" indicates the point of attachment to the carbonyl group R$^9$ is attached to.

In another preferred embodiment, R$^9$ represents a group:

wherein "**" indicates the point of attachment to the carbonyl group R$^9$ is attached to.

In another preferred embodiment, R$^9$ represents a group selected from:

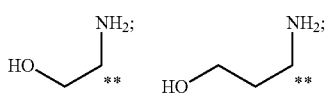

wherein "**" indicates the point of attachment to the carbonyl group $R^9$ is attached to.

In another preferred embodiment, $R^9$ represents a group selected from:

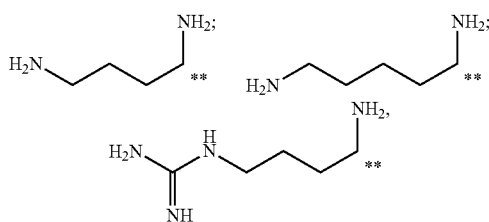

wherein "**" indicates the point of attachment to the carbonyl group $R^9$ is attached to.

In another preferred embodiment, $R^9$ represents

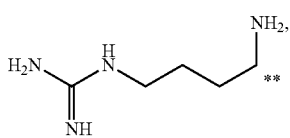

wherein "**" indicates the point of attachment to the carbonyl group $R^9$ is attached to.

In another preferred embodiment, $R^9$ represents a group selected from:

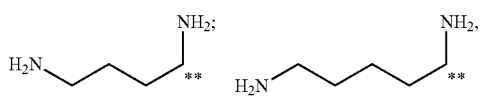

wherein "**" indicates the point of attachment to the carbonyl group $R^9$ is attached to.

In a particularly preferred embodiment, $R^9$ represents

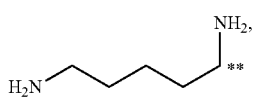

wherein "**" indicates the point of attachment to the carbonyl group $R^9$ is attached to.

In another particularly preferred embodiment, $R^9$ represents a group selected from:

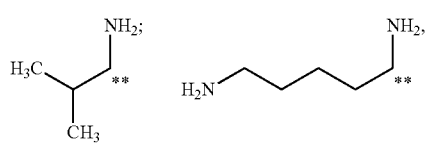

wherein "**" indicates the point of attachment to the carbonyl group $R^9$ is attached to.

In another embodiment, $R^{10}$ and $R^{11}$, independently from each other, represent a group selected from a hydrogen atom and a $C_1$-$C_3$-alkyl- group, or $R^{10}$ and $R^{11}$, together with the nitrogen atom to which they are attached form a 4- to 7-membered heterocycloalkyl ring.

In a preferred embodiment, $R^{10}$ and $R^{11}$, independently from each other, represent a group selected from a hydrogen atom and a $C_1$-$C_3$-alkyl- group.

In another preferred embodiment, $R^{10}$ and $R^{11}$, together with the nitrogen atom to which they are attached form a 4- to 7-membered heterocycloalkyl ring.

In a preferred embodiment, $R^{10}$ and $R^{11}$, independently from each other, represent a group selected from a hydrogen atom and a $C_1$-$C_2$-alkyl- group.

In another preferred embodiment, $R^{10}$ and $R^{11}$, independently from each other, represent a group selected from a hydrogen atom and a methyl- group.

In another embodiment, $R^{12}$ represents a group selected from a hydrogen atom, —OH, —$NR^{10}R^{11}$, —NH—C(=NH)—$NH_2$.

In another embodiment, $R^{12}$ represents a group selected from a hydrogen atom, —OH.

In another embodiment, $R^{12}$ represents a —OH group.

In another embodiment, $R^{12}$ represents a hydrogen atom.

In a preferred embodiment, $R^{12}$ represents a group selected from —$NR^{10}R^{11}$, —NH—C(=NH)—$NH_2$.

In another preferred embodiment, $R^{12}$ represents a group selected from —N(H)$R^{10}$, —NH—C(=NH)—$NH_2$.

In another preferred embodiment, $R^{12}$ represents a group selected from —$NH_2$, —NH—C(=NH)—$NH_2$.

In another preferred embodiment, $R^{12}$ represents —NH—C(=NH)—$NH_2$.

In another preferred embodiment, $R^{12}$ represents —$NR^{10}R^{11}$.

In another preferred embodiment, $R^{12}$ represents —N(H)$R^{10}$.

In a particularly preferred embodiment, $R^{12}$ represents —$NH_2$.

In a further embodiment of the above-mentioned aspect, the invention relates to compounds of formula (I), according to any of the above-mentioned embodiments, in the form of or a tautomer, an N-oxide, a hydrate, a solvate, or a salt thereof, or a mixture of same.

It is to be understood that the present invention relates also to any combination of the preferred embodiments described above.

Some examples of combinations are given hereinafter. However, the invention is not limited to these combinations.

In a preferred embodiment, the invention relates to compounds of the formula (I), supra,
wherein
$R^A$ represents a group selected from:
 —C(=O)—(CH$_2$)$_3$—N(H)$R^3$,
 —C(=O)—(CR$^4$R$^5$)—N(R$^6$)R$^7$,
 —C(=O)—O—(CH$_2$)$_2$—N(H)R$^3$,
 —C(=O)—O—(CR$^4$R$^5$)—O—P(=O)(OH)$_2$,
 —C(=O)—O—(CR$^4$R$^5$)—O—C(=O)—R$^8$,
 —C(=O)—O—(CR$^4$R$^5$)—O—C(=O)—CH(R$^6$)— NH—C(=O)—R$^9$;
$R^1$ represents a group selected from methoxy- and 2,2,2-trifluoroethoxy-;
$R^2$ represents a group selected from:

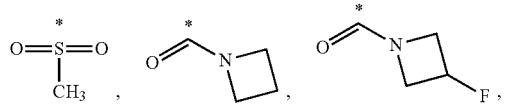

-continued

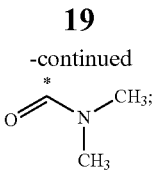

wherein "*" indicates the point of attachment to the phenyl ring $R^2$ is attached to;
$R^3$ represents a $C_1$-$C_3$-alkyl- group;
$R^4$ and $R^5$, independently from each other, represent a group selected from a hydrogen atom and a $C_1$-$C_3$-alkyl- group, or
$R^4$ and $R^5$, together with the carbon atom to which they are attached, form a $C_3$-$C_6$-cycloalkyl ring;
$R^6$ represents a hydrogen atom or a $C_1$-$C_3$-alkyl- group;
$R^7$ represents a hydrogen atom or a group —C(=O)$R^9$;
$R^8$ represents a group selected from:
  $C_1$-$C_6$-alkyl, $C_3$-$C_6$-cycloalkyl-,
  4- to 7-membered heterocycloalkyl-;
  said group being optionally substituted, one or more times, identically or differently, with a group selected from:
  —OH, —NH$_2$, —N(H)$R^{10}$, —N($R^{10}$)$R^{11}$, —O—P(=O)(OH)$_2$;
$R^9$ represents a group

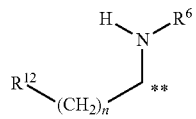

wherein "**" indicates the point of attachment to the carbonyl group $R^9$ is attached to;
$R^{10}$ and $R^{11}$, independently from each other, represent a group selected from a hydrogen atom and a $C_1$-$C_3$-alkyl- group, or
$R^{10}$ and $R^{11}$, together with the nitrogen atom to which they are attached form a 4- to 7-membered heterocycloalkyl ring;
$R^{12}$ represents a group selected from a hydrogen atom, —OH, —N$R^{10}R^{11}$, —NH—C(=NH)—NH$_2$;
n is an integer of 0, 1, 2, 3 or 4;
or a tautomer, an N-oxide, a hydrate, a solvate, or a salt thereof, or a mixture of same.

In another preferred embodiment,
$R^A$ represents a group selected from:
  —C(=O)—(CH$_2$)$_3$—N(H)$R^3$,
  —C(=O)—(C$R^4R^5$)—N($R^6$)$R^7$,
  —C(=O)—O—(CH$_2$)$_2$—N(H)$R^3$,
  —C(=O)—O—(C$R^4R^5$)—O—P(=O)(OH)$_2$,
  —C(=O)—O—(C$R^4R^5$)—O—C(=O)—$R^8$,
  —C(=O)—O—(C$R^4R^5$)—O—C(=O)—CH($R^6$)—NH—C(=O)—$R^9$;
$R^1$ represents a group selected from methoxy- and 2,2,2-trifluoroethoxy-;
$R^2$ represents a group selected from:

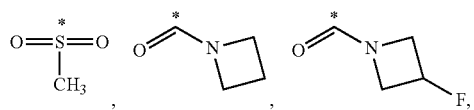

-continued

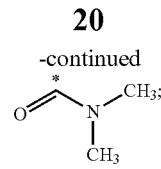

wherein "*" indicates the point of attachment to the phenyl ring $R^2$ is attached to;
$R^3$ represents a methyl- group;
$R^4$ represents a hydrogen atom or a $C_1$-$C_3$-alkyl- group;
$R^5$ represents a hydrogen atom;
$R^6$ represents a hydrogen atom or a methyl- group;
$R^7$ represents a hydrogen atom or a group —C(=O)$R^9$;
$R^8$ represents a group selected from:
  $C_1$-$C_6$-alkyl, substituted one or more times, identically or differently, with a group selected from: —NH$_2$, —N(H)$R^{10}$, —N($R^{10}$)$R^{11}$;
  4- to 7-membered heterocycloalkyl-, optionally substituted, one or more times, identically or differently, with a group selected from:
  —NH$_2$, —N(H)$R^{10}$, —N($R^{10}$)$R^{11}$;
$R^9$ represents a group

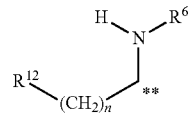

wherein "**" indicates the point of attachment to the carbonyl group $R^9$ is attached to;
$R^{10}$ and $R^{11}$, independently from each other, represent a group selected from a hydrogen atom and a methyl- group;
$R^{12}$ represents a group selected from a hydrogen atom, —OH, —N$R^{10}R^{11}$, —NH—C(=NH)—NH$_2$;
n is an integer of 0, 1, 2, 3 or 4;
or a tautomer, an N-oxide, a hydrate, a solvate, or a salt thereof, or a mixture of same.

In yet another preferred embodiment,
$R^A$ represents a group selected from:
  —C(=O)—(CH$_2$)$_3$—N(H)$R^3$,
  —C(=O)—(C$R^4R^5$)—N($R^6$)$R^7$,
  —C(=O)—O—(CH$_2$)$_2$—N(H)$R^3$,
  —C(=O)—O—(C$R^4R^5$)—O—P(=O)(OH)$_2$,
  —C(=O)—O—(C$R^4R^5$)—O—C(=O)—$R^8$,
  —C(=O)—O—(C$R^4R^5$)—O—C(=O)—CH($R^6$)—NH—C(=O)—$R^9$;
$R^1$ represents methoxy-;
$R^2$ represents a —S(=O)$_2$CH$_3$ group;
$R^3$ represents a methyl- group;
$R^4$ represents a hydrogen atom or a methyl- group;
$R^5$ represents a hydrogen atom;
$R^6$ represents a hydrogen atom or a methyl- group;
$R^7$ represents a hydrogen atom or a group —C(=O)$R^9$;
$R^8$ represents a group selected from:
  $C_1$-$C_6$-alkyl, substituted one or more times, identically or differently, with a group selected from —NH$_2$, —N(H)$R^{10}$, —N($R^{10}$)$R^{11}$,
  a heterocycloalkyl group selected from pyrrolidinyl-, piperidinyl-, morpholinyl-, and piperazinyl-;

$R^9$ represents a group selected from

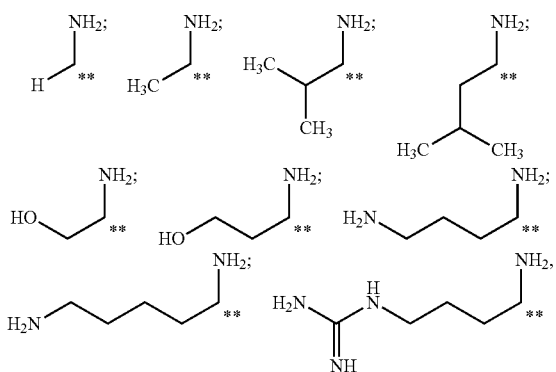

wherein "**" indicates the point of attachment to the carbonyl group $R^9$ is attached to;
$R^{10}$ and $R^{11}$, independently from each other, represent a group selected from a hydrogen atom and a methyl- group;
or a tautomer, an N-oxide, a hydrate, a solvate, or a salt thereof, or a mixture of same.

In a particularly preferred embodiment,
$R^A$ represents a group selected from:
- —C(=O)—(CH$_2$)$_3$—N(H)R$^3$,
- —C(=O)—(CR$^4$R$^5$)—N(R$^6$)R$^7$,
- —C(=O)—O—(CH$_2$)$_2$—N(H)R$^3$,
- —C(=O)—O—(CR$^4$R$^5$)—O—P(=O)(OH)$_2$,
- —C(=O)—O—(CR$^4$R$^5$)—O—C(=O)—R$^8$,
- —C(=O)—O—(CR$^4$R$^5$)—O—C(=O)—CH(R$^6$)—NH—C(=O)—R$^9$;

$R^1$ represents methoxy-;
$R^2$ represents a —S(=O)$_2$CH$_3$ group;
$R^3$ represents a methyl- group;
$R^4$ represents a hydrogen atom or a methyl- group;
$R^5$ represents a hydrogen atom;
$R^6$ represents a methyl- group;
$R^7$ represents a hydrogen atom or a group —C(=O)R$^9$;
$R^8$ represents a group selected from:

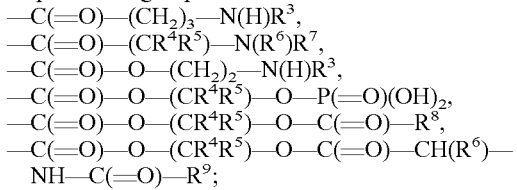

wherein "#" represents the point of attachment to the carbonyl group $R^8$ is attached to;
$R^9$ represents a group

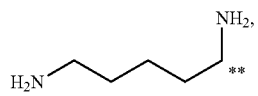

wherein "**" indicates the point of attachment to the carbonyl group $R^9$ is attached to;
or a tautomer, an N-oxide, a hydrate, a solvate, or a salt thereof, or a mixture of same.

In another particularly preferred embodiment,
$R^A$ represents a group:
- —C(=O)—O—(CR$^4$R$^5$)—O—C(=O)—R$^8$, $R^1$ represents methoxy-;
$R^2$ represents a —S(=O)$_2$CH$_3$ group;
$R^4$ represents a hydrogen atom or a C$_1$-C$_3$-alkyl- group;
$R^5$ represents a hydrogen atom;
$R^8$ represents a group selected from:

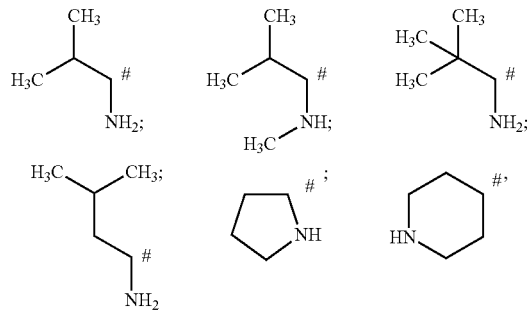

wherein "#" represents the point of attachment to the carbonyl group $R^8$ is attached to;
or a tautomer, an N-oxide, a hydrate, a solvate, or a salt thereof, or a mixture of same.

It is to be understood that the present invention relates to any sub-combination within any embodiment or aspect of the present invention of compounds of general formula (I), supra.

More particularly still, the present invention covers compounds of general formula (I) which are disclosed in the Examples section of this text, infra.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

The compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, viz.:

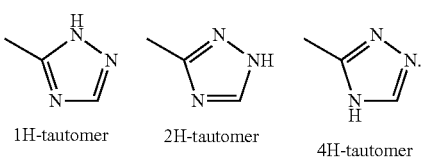

1H-tautomer   2H-tautomer   4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as hydrates, solvates, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, the compounds according to the invention may form salts with a quarternary ammonium ion obtainable e.g. by quarternisation of a basic nitrogen containing group with agents like lower alkylhalides such as methyl-, ethyl-, propyl-, and butylchlorides, -bromides and -iodides; dialkylsulfates like dimethyl-, diethyl-, dibutyl- and diamylsulfates, long chain halides such as decyl-, lauryl-, myristyl- and stearylchlorides, -bromides and -iodides, aralkylhalides like benzyl- and phenethylbromides and others. Examples of suitable quarternary ammonium ions are tetramethylammonium, tetraethylammonium, tetra(n-propyl)ammonium, tetra (n-butyl)ammonium, or N-benzyl-N,N,N-trimethylammonium.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

Furthermore, the present invention includes all possible crystalline forms, or polymorphs, of the compounds of the present invention, either as single polymorphs, or as a mixture of more than one polymorphs, in any ratio.

More particularly still, the present invention covers compounds of general formula (I) which are disclosed in the Example section of this text, infra.

In accordance with another aspect, the present invention covers methods of preparing compounds of the present invention, said methods comprising the steps as described in the Experimental Section herein.

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions.

Pharmaceutical compositions according to the present invention can be illustrated as follows:

Sterile i.v. Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an i.v. infusion over about 60 minutes.

As mentioned supra, compound A has been found to effectively inhibit Mps-1 and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of general formula (I), or a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula (I), described supra, or a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula (I) described supra for manufacturing a pharmaceutical composition for the treatment or prophylaxis of a disease.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant serine-threonine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

General Synthesis of Prodrug Compounds of Formula (I)

The following paragraphs outline a variety of synthetic approaches suitable to prepare compounds of formulae (Ia), (Ib), (Ic), (Id) and (Ie) as shown in the following schemes, all constituting subsets of formula (I) in that they feature different embodiments of the group $R^4$.

In addition to the routes described below, also other routes may be used to synthesise the target compounds, in accordance with common general knowledge of a person skilled in the art of organic synthesis. The order of transformations exemplified in the following Schemes is therefore not intended to be limiting, and suitable synthesis steps from various schemes can be combined to form additional synthesis sequences. In addition, interconversion of any of the substituents shown can be achieved before and/or after the exemplified transformations. These modifications can be such as reduction or oxidation of functional groups, halogenation, metallation, metal catalysed coupling reactions, substitution or other reactions known to a person skilled in the art. These transformations include those which introduce a functionality allowing for further interconversion of substituents. In particular, the synthetic routes below encompass the introduction and cleavage of protective groups. Appropriate protective groups and their introduction and cleavage are well-known to a person skilled in the art (see for example T. W. Greene and P. G. M. Wuts in *Protective Groups in Organic Synthesis*, $3^{rd}$ edition, Wiley 1999); more specifically, protective groups include groups such as $PG^1$ (protecting group for hydroxy as defined supra), and $PG^2$ (protecting group for amino as defined supra). Where appropriate, this is indicated by the inclusion of "'" in the respective denomination of the respective residue, e.g. $R^{8'}$ for a protected equivalent of $R^8$, and vice versa in $R^{9'}$ and $R^9$, respectively, in the schemes shown below.

Specific examples are described in the subsequent paragraphs. Further, it is possible that two or more successive steps may be performed without work-up being performed between said steps, e.g. a "one-pot" reaction, as it is well-known to a person skilled in the art.

As outlined in scheme 1, compounds of the general formula (Ia), in which $R^1$, $R^2$ and $R^3$ are as defined for the general formula (I) can be prepared by reacting of starting materials of the formula (II), in which $R^1$ and $R^2$ are as defined for the general formula (I), with anhydrides of the formula (III), in which $R^3$ is as defined for the general formula (I), and in which $PG^2$ represents a protecting group for amino groups, as defined supra, such as tert-butoxycarbonyl (Boc), benzyloxycarbonyl (Z) or p-methoxybenzyl (PMB), in the presence of a suitable base, to give intermediates of the formula (IV). Said intermediates can be converted into compounds of the formula (Ia) by removal of $PG^2$ using deprotection methods known to the person skilled in the art (see e.g T. W. Greene and P. G. M. Wuts in *Protective Groups in Organic Synthesis*, $3^{rd}$ edition, Wiley 1999). Protective groups $PG^2$, if occurring more than once in one molecule, can be identical or different. Prodrug compounds of formula (Ia) are typically isolated as salts, preferably as HCl salts or as TFA-salts.

The preparation of starting materials (II) is described in the Experimental Section in several instances, and can be alternatively performed e.g. according to WO2012/143329 (A1). Anhydrides such as (III) can be approached by methods known to the person skilled in the art and are also described in the literature (see e.g. Y. Armaki et al., *Chem. Pharm. Bull.* 52, 258 (2004)).

(VII) are reacted with a carboxylate salt of the formula (VIII), in which $M^+$ stands for a monovalent cation such as an alkali cation or an ammonium salt, preferably cesium, and in which $R^{8'}$ represents an equivalent of $R^8$ featuring an additional protective group if needed, as described supra, in a suitable solvent, such as N,N-dimethylformamide, to give intermediates of the formula (IX). This substitution can also be performed in the presence of a catalytic amount of an iodide salt like sodium iodide or potassium iodide whereby the leaving group LG is in situ transformed to iodide. Alternatively, the leaving group LG can be transformed to Scheme 1: Synthesis of prodrug compounds of formula (Ia) from intermediates (II)

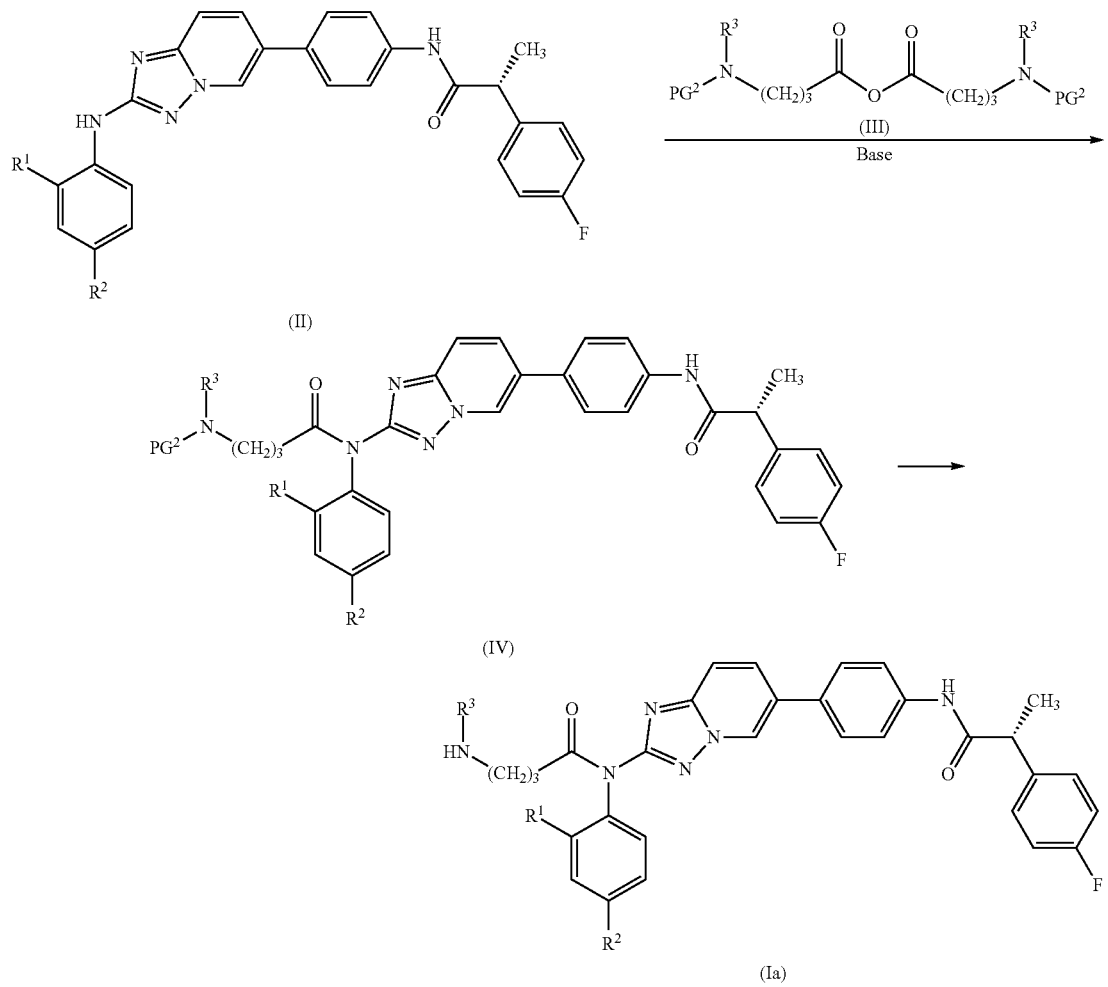

Scheme 2 outlines the synthesis of prodrug derivatives (Ic), in which $R^1$, $R^2$, $R^4$, $R^5$ and $R^8$ are as defined for compounds of general formula (I), from intermediates of the formula (V), in which $R^1$ and $R^2$ are as defined for compounds of general formula (I). The preparation of intermediates (V) can be performed as described in the Experimental Section. Intermediates (V) are deprotonated by a suitable base, such as sodium hydride, in a suitable solvent, such as an ether, e.g. tetrahydrofuran, and subsequently reacted with a chloroformiate of formula (VI), in which $R^4$ and $R^5$ are as defined for compounds of the general formula (I), and LG stands for a leaving group, as defined supra, preferably chloro, to give carbamates (VII). Chloroformiates of formula (VI) are well known to the person skilled in the art, and are commercially available in several cases. Said carbamates iodide prior to the substitution reaction. Intermediates (IX) are then subjected to a Suzuki coupling involving boronic acid derivatives (X), in which $R^E$ stand for hydrogen or independently from each other stand for $C_1$-$C_6$-alkyl-, or together form a $C_2$-$C_6$-alkylene- group. Suzuki couplings are well known to the person skilled in the art, the coupling as shown in Scheme 2 employs S-Phos as a ligand, $Pd(OAc)_2$ or $Pd_2(dba)_3$ as palladium source, potassium phosphate monohydrate or potassium phosphate as a base, and toluene or N-methylpyrrolidine or mixtures of toluene and N-methylpyrrolidine as a solvent. The coupling products (XI) are subsequently deprotected (if needed), e.g. by treatment with hydrochloric acid to remove a Boc group, to give prodrug compounds of formula (Ic). Prodrug compounds of formula (Ic) are typically isolated as salts, preferably as HCl salts or as TFA-salts.

Scheme 2: Synthesis of prodrug compounds of formula (Ic) from intermediates (V)
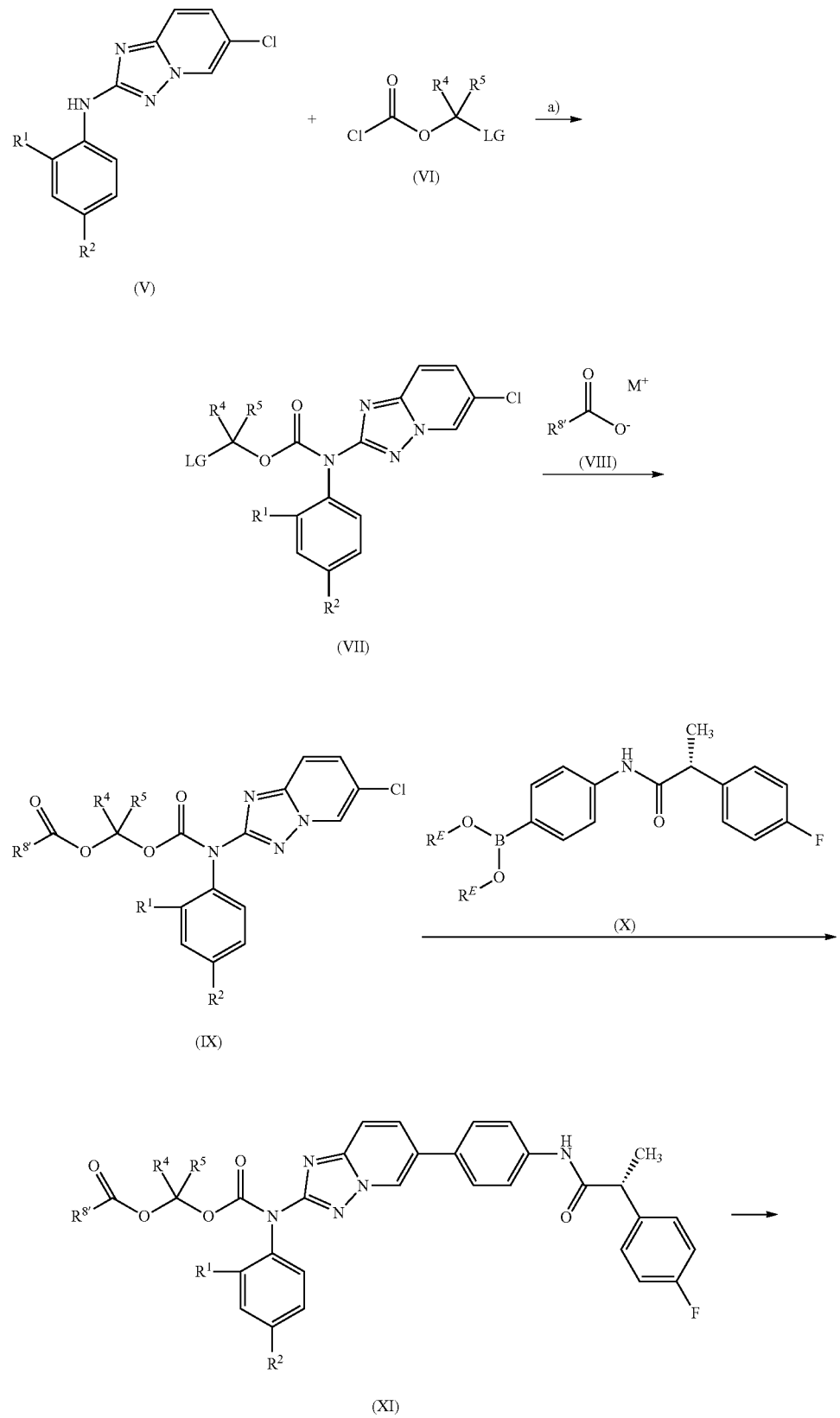

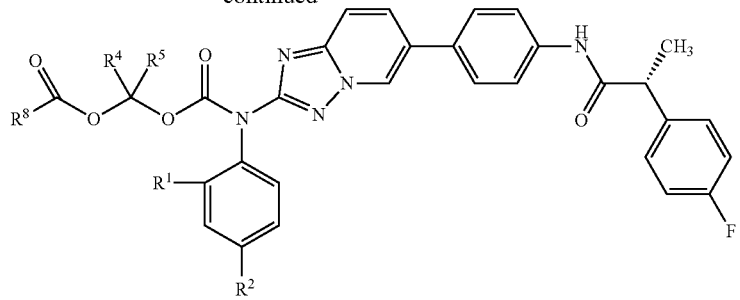

(Ic)

Prodrug compounds of the formula (Id), featuring a phosphate unit, can be synthesised from carbamates of formula (VII), in which $R^1$, $R^2$, $R^4$ and $R^5$ are as defined for compounds of the general formula (I), and LG stands for a leaving group, as defined supra, preferably chloro. Said carbamates can be prepared as described in Scheme 2. Carbamates (VII) are reacted with an alkali salt of di-tert-butyl phosphate, e.g. the commercially available potassium salt (XII), to give phosphate intermediates (XIII). This substitution can also be performed in the presence of a catalytic amount of an iodide salt like sodium iodide or potassium iodide whereby the leaving group LG is in situ transformed to iodide. Alternatively, the leaving group LG can be transformed to iodide prior to the substitution reaction. Phosphate intermediates (XIII) are in turn subjected to a Suzuki coupling with boronic acid derivatives (X) in which $R^E$ stand for hydrogen or independently from each other stand for $C_1$-$C_6$-alkyl-, or together form a $C_2$-$C_6$-alkylene- group. Suzuki couplings are well known to the person skilled in the art, the coupling as shown in Scheme 3 employs S-Phos as a ligand, Pd(OAc)$_2$ or Pd$_2$(dba)$_3$ as palladium source, potassium phosphate monohydrate or potassium phosphate as a base, and toluene or N-methyl-pyrrolidine as a solvent. The coupling products (XIV) are then subjected to an acidic cleavage, e.g. with a solution of hydrogen chloride in dioxane and dichloromethane, of the tert-butyl phosphate ester groups, to give phosphate prodrug compounds of the formula (Id).

Scheme 3: Synthesis of phosphate prodrug compounds of formula (Id) from carbamates (VII)

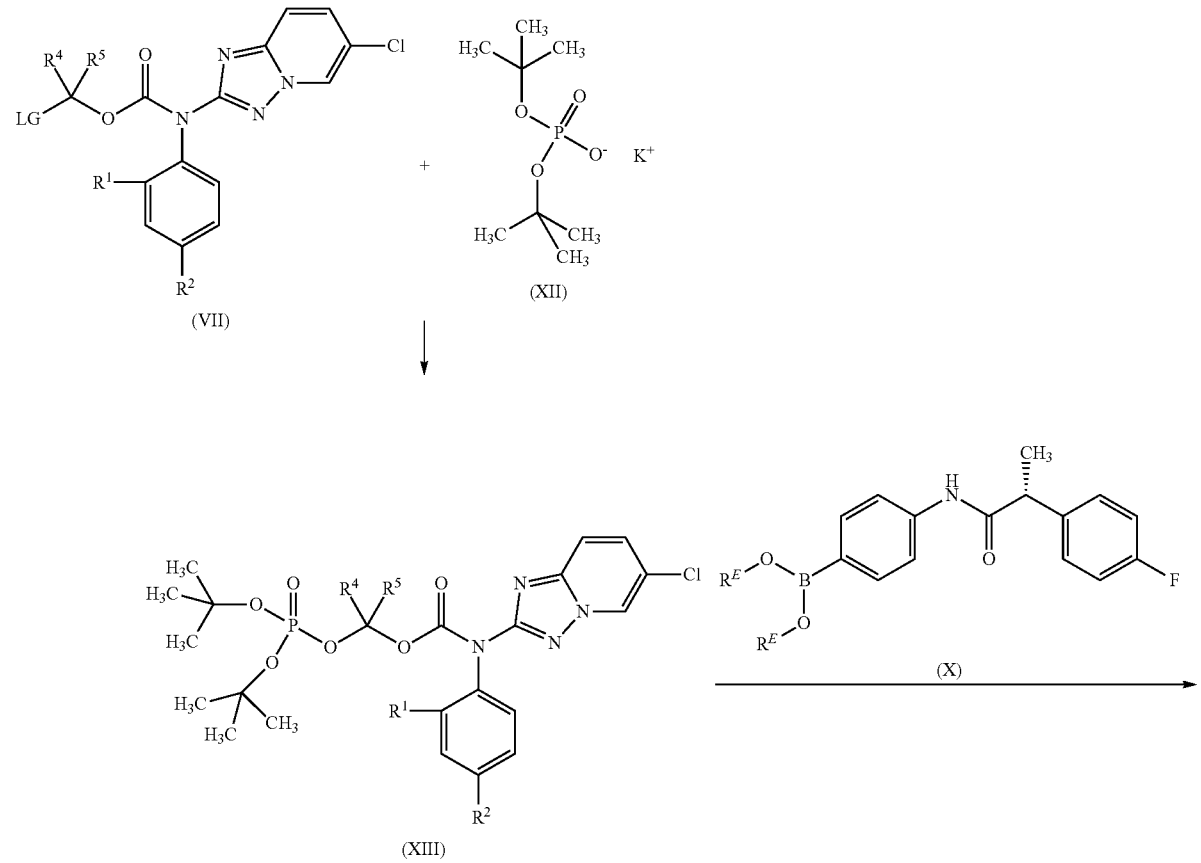

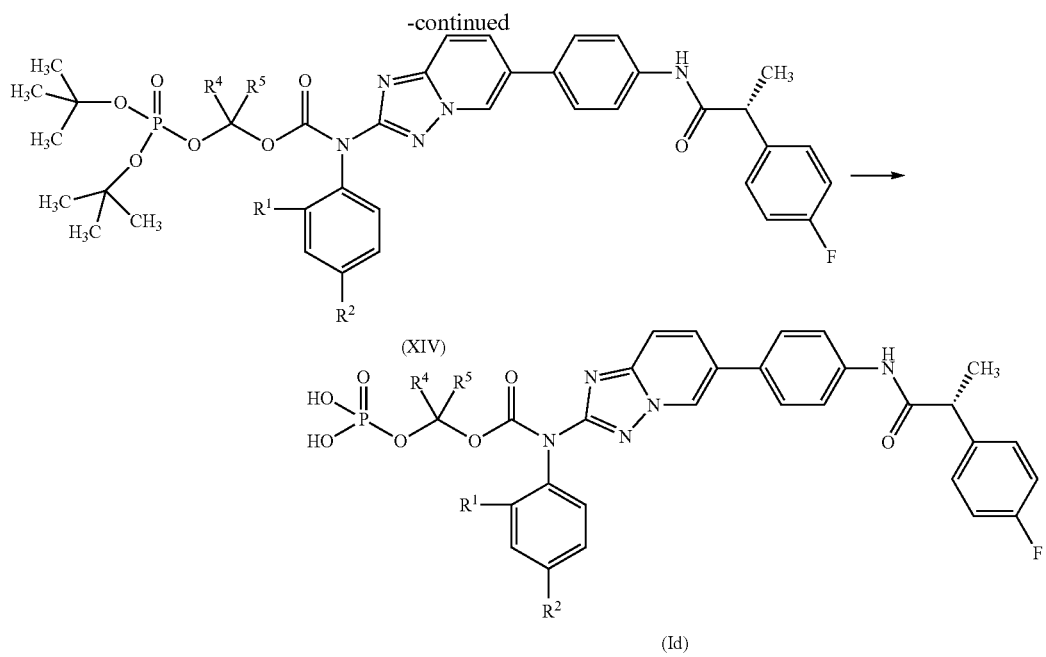

(XIV)

(Id)

Prodrug compounds of the general formula (Ie), featuring a dipeptide or dipeptide-like group, can be prepared from amines (XV), in which $R^1$, $R^2$, $R^4$, $R^5$, and $R^6$ are as defined for compounds of the general formula (I), by coupling with an optionally protected amino acid (XVI), in which $R^{9'}$ represents an equivalent of $R^9$ featuring an additional protective group if needed, as described supra. The coupling can be performed with a variety of standard peptide coupling reagents well known to the person skilled in the art, such as HATU; optionally protected amino acids of the formula (XVI) are commercially available in many instances.

Amines of the formula (XV) can be approached with the methods described in scheme 2 (compounds of formula (XV) can be understood as compounds of formula (Ic), in which $R^8$ stands for —CH($R^6$)—NH$_2$), and in the Experimental Section to give intermediates of formula (XVII), which are subsequently deprotected (if needed), e.g. by treatment with hydrochloric acid to remove a Boc group, to give prodrug compounds of formula (Ie). Prodrug compounds of formula (Ie) are typically isolated as salts, preferably as HCl salts or as TFA-salts.

Scheme 4: Synthesis of prodrug compounds of formula (Ie) from amines (XV)

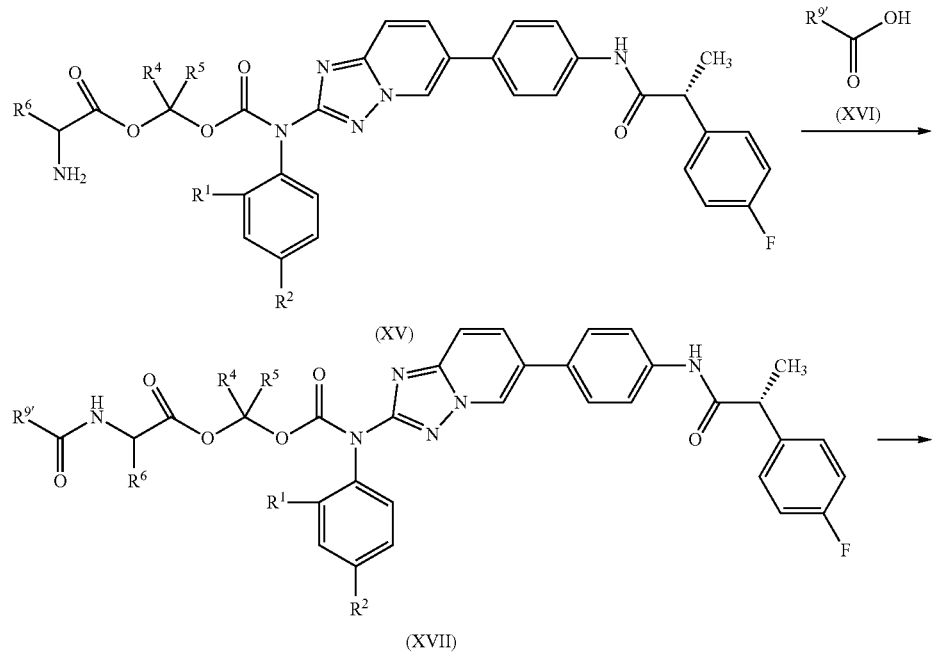

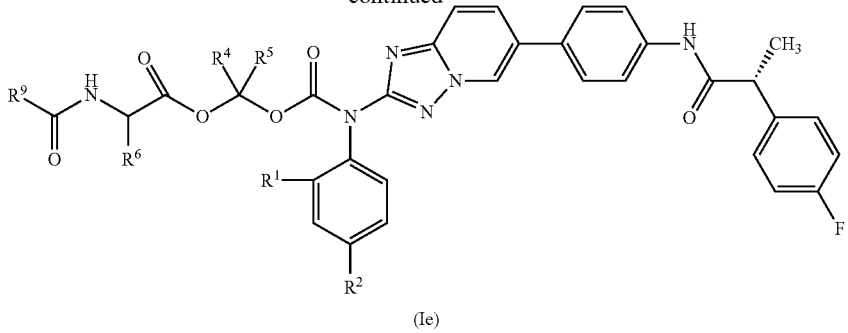

(Ie)

EXPERIMENTAL SECTION

The following Table lists the abbreviations used in this paragraph, and in the Examples section. NMR peak forms are stated as they appear in the spectra, possible higher order effects have not been considered.

| Abbreviation | Meaning |
| --- | --- |
| Ac | acetyl |
| BINAP | 2,2'-bis(diphenylphosphino)-1,1'-binaphthyl |
| Boc | tert-butyloxycarbonyl |
| br | broad |
| Brett-Phos | 2-(dicyclohexylphosphino)-3,6-dimethoxy-2'-4'-6'-tri-i-propyl-1,1'-biphenyl |
| c- | cyclo- |
| 1-Chloroethyl chloroformate | 1-chloroethyl carbonochloridate |
| Chloromethyl chloroformate | chloromethyl carbonochloridate |
| d | doublet |
| dd | doublet of doublets |
| DCM | dichloromethane |
| DME | 1,2-dimethoxyethane |
| DIPE | diisopropylether |
| DIPEA | N,N-diisopropylethylamine |
| DMF | N,N-dimethylformamide |
| DMSO | dimethyl sulfoxide |
| Dppf | 1,1'-bis(diphenylphosphino)ferrocene |
| Eq | equivalent |
| ESI | electrospray ionisation |
| HATU | N-[(dimethylamino)(3H-[1,2,3]triazolo[4,5-b]pyridin-3-yloxy)-methylene]-N-methylmethanaminium hexafluorophosphate |
| Hünig Base | N,N-diisopropylethylamine |
| m | multiplet |
| m.p. | melting point in ° C. |
| MS | mass spectrometry |
| MW | molecular weight |
| NaOtBu | sodium tert-butoxide; sodium 2-methylpropan-2-olate |
| NMP | N-methylpyrrolidinone |
| NMR | nuclear magnetic resonance spectroscopy: chemical shifts (δ) are given in ppm. |
| $PdCl_2(PPh_3)_2$ | dichlorobis(triphenylphosphine)palladium(II) |
| $Pd(dba)_2$ | bis-(dibenzylideneacetone)palladium(0) complex |
| $Pd_2(dba)_3$ | tris-(dibenzylideneacetone)dipalladium(0) chloroform complex |
| $Pd(dppf)Cl_2$ | dichloro[1,1'-bis(diphenylphosphino)ferrocene]palladium(II) |
| $Pd(dppf)Cl_2 \cdot CH_2Cl_2$ | dichloro[1,1'-bis(diphenylphosphino)ferrocene]palladium(II) dichloromethane adduct |
| Pd-Brett-Phos-pre-cat | chloro[2-(dicyclohexylphosphino)-3,6-dimethoxy-2'-4'-6'-tri-iso-propyl-1,1'-biphenyl][2-(2-aminoethyl)phenyl]palladium(II) |
| Pd-tBu-X-Phos-pre-cat | chloro(2-di-tert-butylphosphino-2',4',6'-tri-isopropyl-1,1'-biphenyl)[2-(2-aminoethyl)phenyl] palladium(II), |
| Pd-X-Phos-pre-cat | chloro(2-dicyclohexylphosphino-2',4',6'-tri-isopropyl-1,1'-biphenyl)[2-(2-aminoethyl)phenyl] palladium(II) methyl-tert-butylether adduct |
| $PPh_3$ | triphenylphosphine |
| $P(oTol)_3$ | tri-o-tolylphosphine |
| q | quartet |

-continued

| Abbreviation | Meaning |
|---|---|
| quin | quintett |
| Rac | racemic |
| Rt | room temperature |
| r.t. | room temperature |
| RT | retention time in minutes |
| s | singlet |
| S-Phos | dicyclohexyl(2',6'-dimethoxybiphenyl-2-yl)phosphine |
| t | triplet |
| TBAF | tetrabutylammoniumfluoride |
| tBu-X-Phos | 2-di-tert-butylphosphino-2',4',6'-tri-isopropyl-1,1'-biphenyl |
| TBDPS | tert-butyldiphenylsilyl |
| TBTU | N-[(1H-benzotriazol-1-yloxy)(dimethylamino)methylene]-N-methylmethanaminium tetrafluoroborate |
| TEA | triethylamine |
| TFA | trifluoroacetic acid |
| THF | tetrahydrofuran |
| TMS | trimethylsilyl |
| Ts | para toluenesulfonyl; (tosyl) |
| UPLC | ultra performance liquid chromatography |
| X-Phos | 2-dicyclohexylphosphino-2',4',6'-triisopropylbiphenyl |

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallisation. In some cases, impurities may be stirred out using a suitable solvent. In some cases, the compounds may be purified by chromatography, particularly flash chromatography, using for example pre-packed silica gel cartridges, e.g. from Separtis such as Isolute® Flash silica gel (silica gel chromatography) or Isolute® Flash NH2 silica gel (aminophase-silica-gel chromatography) in combination with a suitable chromatographic system such as a Flashmaster II (Separtis) or an Isolera system (Biotage) and eluents such as, for example, gradients of hexane/ethyl acetate or DCM/methanol. In some cases, the compounds may be purified by preparative HPLC using, for example, a Waters autopurifier equipped with a diode array detector and/or on-line electrospray ionisation mass spectrometer in combination with a suitable pre-packed reverse phase column and eluants such as, for example, gradients of water and acetonitrile which may contain additives such as trifluoroacetic acid, formic acid or aqueous ammonia.

Optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Diacel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HCl", "x CF$_3$COOH", "x Na$^+$", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

Analytical UPLC-MS was performed as follows:

Method A: System: UPLC Acquity (Waters) with PDA Detector and Waters ZQ mass spectrometer; Column: Acquity BEH C18 1.7 μm 2.1×50 mm; Temperature: 60° C.; Solvent A: Water+0.1% formic acid; Solvent B: acetonitrile; Gradient: 99% A→1% A (1.6 min)→1% A (0.4 min); Flow: 0.8 mL/min; Injection Volume: 1.0 μl (0.1 mg-1 mg/mL sample concentration); Detection: PDA scan range 210-400 nm—Fixed and ESI (+), scan range 170-800 m/z LC-MS Methods:

Method 1:

Instrument: Waters ACQUITY SQD UPLC System; Column: Waters Acquity UPLC HSS T3 1.8μ 50×1 mm; Eluent A: 1 l Wasser+0.25 ml 99% ige Formic acid, Eluent B: 1 l Acetonitril+0.25 ml 99% ige Formic acid; Gradient: 0.0 min 90% A →1.2 min 5% A→2.0 min 5% A Ofen: 50° C.; Flow: 0.40 ml/min; UV-Detection: 208-400 nm.

Preparation of Compound A1

Route I (2R)-2-(4-fluorophenyl)-N-[4-(2-{[2-methoxy-4-(methylsulfonyl)phenyl]-amino}[1,2,4]triazolo[1,5-α]pyridin-6-yl)phenyl]propanamide

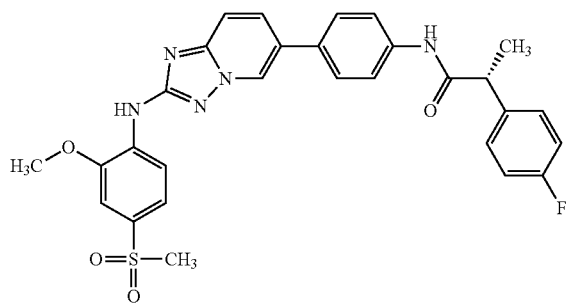 [SMILES: COc1cc(S(C)(=O)=O)ccc1Nc1nc2ccc(-c3ccc(NC(=O)[C@H](C)c4ccc(F)cc4)cc3)cn2n1]

To a stirred suspension of Int08.011 (6.0 g) in DMF (48 mL) and dichloromethane (96 mL) was added sodium bicarbonate (3.69 g), (2R)-2-(4-fluorophenyl)propanoic acid (2.71 g) and HATU (8.36 g). The mixture was stirred at room temperature for 4 h. Water was added, and the mixture was stirred for 30 minutes. A half-saturated solution of sodium bicarbonate was added and the mixture was extracted with ethyl acetate. The organic phase was washed with saturated sodium chloride solution, dried (sodium sulfate) and the solvent was removed in vacuum. Silicagel chromatography gave a solid that was triturated with ethyl acetate to give 7.44 g of the title compound.

$^1$H-NMR (400 MHz, DMSO-$d_6$): δ [ppm]=1.40 (d, 3H), 3.16 (s, 3H), 3.84 (q, 1H), 3.96 (s, 3H), 7.09-7.18 (m, 2H), 7.36-7.44 (m, 3H), 7.51 (dd, 1H), 7.63-7.76 (m, 5H), 7.92 (dd, 1H), 8.48 (d, 1H), 8.60 (s, 1H), 9.10 (d, 1H), 10.16 (s, 1H).

$[α]_D^{20}$: −77.0° (in DMSO).

Determination of Enantiomeric Purity by Analytical Chiral HPLC:

Column: Chiralcel OD-RH 150×4.6; Flow: 1.00 mL/min; Solvent: A: Water with 0.1% formic acid, B: Acetonitrile; Solvent mixture: 40% A+60% B. Run Time: 30 min. Retention Time: 12.83 min; UV 254 nm; Enantiomeric Ratio: <1%:>99%.

Intermediate Int08.011

6-(4-aminophenyl)-N-[2-methoxy-4-(methylsulfonyl)phenyl][1,2,4]-triazolo[1,5-α]pyridin-2-amine

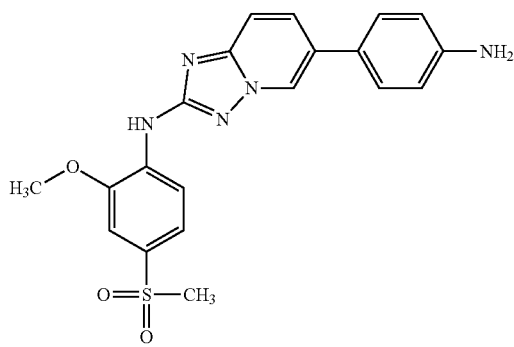 [SMILES: COc1cc(S(C)(=O)=O)ccc1Nc1nc2ccc(-c3ccc(N)cc3)cn2n1]

To a stirred suspension of Int08.010 (12.3 g) in dichloromethane (40 mL) was added TFA (46 mL). The mixture was stirred at room temperature for 16 h. Further TFA was added (1 mL) and the mixture was stirred at room temperature for 5 h. A saturated solution of potassium carbonate was added until pH 9 was reached. The mixture was extracted with dichloromethane and methanol (10:1 mixture). The solution was dried (sodium sulfate) and the solvent was removed in vacuum. The residue was triturated with ethanol to give 9.2 g of the title compound.

$^1$H-NMR (300 MHz, DMSO-$d_6$): δ [ppm]=3.16 (s, 3H), 3.95 (s, 3H), 5.30 (s, 2H), 6.63 (d, 2H), 7.38-7.46 (m, 3H), 7.51 (dd, 1H), 7.61 (d, 1H), 7.84 (dd, 1H), 8.48 (d, 1H), 8.55 (s, 1H), 8.93 (d, 1H).

Intermediate Int08.010 tert-butyl [4-(2-{[2-methoxy-4-(methylsulfonyl)phenyl]amino}[1,2,4]-triazolo[1,5-α]pyridin-6-yl)phenyl]carbamate

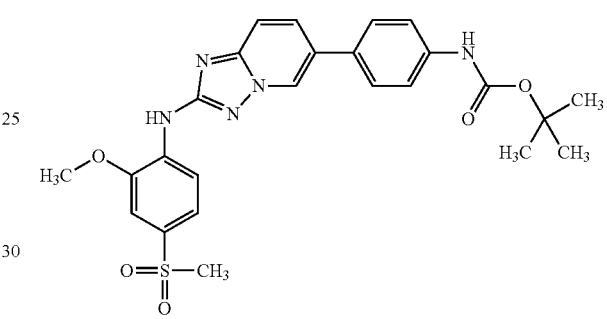

To a stirred suspension of Int01.03 (4.0 g) in toluene (250 mL) and NMP (25 mL) was added Int03.02 (8.31 g), chloro(2-dicyclohexylphosphino-2',4',6'-tri-isopropyl-1,1'-biphenyl)[2-(2-aminoethyl)phenyl]palladium(II) methyl-tert-butylether adduct (1.08 g), X-Phos (0.64 g) and powdered potassium phosphate (16.6 g). The flask was degassed twice and backfilled with argon. The mixture was heated to reflux for 16 h.

The reaction mixture was filtered through a microfilter and the solvent was removed in vacuum. The residue was triturated with dichloromethane to give 12.3 g of the title compound.

$^1$H-NMR (400 MHz, DMSO-$d_6$): δ [ppm]=1.46 (s, 9H), 3.16 (s, 3H), 3.96 (s, 3H), 7.43 (d, 1H), 7.48-7.59 (m, 3H), 7.63-7.72 (m, 3H), 7.92 (dd, 1H), 8.48 (d, 1H), 8.58 (s, 1H), 9.06-9.12 (m, 1H), 9.46 (s, 1H).

Intermediate Int01.03 tert-butyl [4-(2-amino[1,2,4]triazolo[1,5-α]pyridin-6-yl)phenyl]carbamate

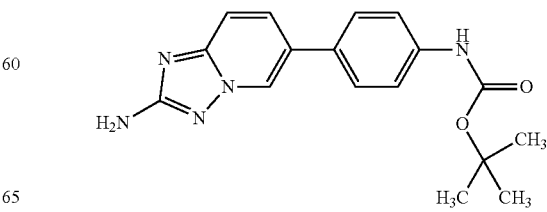

To a stirred solution of Int01.02 (5.82 g) in 1-propanol (400 mL) was added 2M potassium carbonate solution (41 mL), {4-[(tert-butoxycarbonyl)amino]phenyl}boronic acid (8.6 g), triphenylphosphine (150 mg) and PdCl$_2$(PPh$_3$)$_2$ (1.9 g). The mixture was heated to reflux for 4 h, the solvent was removed in vacuum, water (150 mL) was added and the mixture was extracted with ethyl acetate (500 mL). The organic phase was dried (sodium sulfate), filtered through Celite and the solvent was removed in vacuum. The residue was triturated with DCM to give the title compound as a white solid. Yield: 7.2 g.

$^1$H-NMR (400 MHz, DMSO-d$_6$): δ [ppm]=1.37-1.55 (m, 9H), 5.99 (s, 2H), 7.36 (dd, 1H), 7.48-7.55 (m, 2H), 7.55-7.62 (m, 2H), 7.69 (dd, 1H), 8.78 (dd, 1H), 9.44 (s, 1H).

Int01.02

6-Bromo[1,2,4]triazolo[1,5-α]pyridin-2-amine

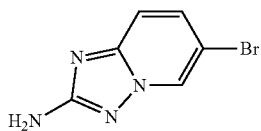

Hydroxylammonium chloride (39.8 g) was suspended in methanol (200 mL) and ethanol (190 mL) and Hünig Base (59 mL) was added at r.t. The mixture was heated to 60° C., Int01.01 (30 g) was added portionwise, and the mixture was stirred at 60° C. for 2 h. The solvent was removed in vacuum and water (150 mL) was added. A solid was collected by filtration and was washed with water and dried in vacuum.

Yield: 19.3 g of the title compound.

$^1$H-NMR (300 MHz, DMSO-d$_6$): δ [ppm]=6.10 (s, 2H), 7.28 (dd, 1H), 7.51 (dd, 1H), 8.88 (dd, 1H).

Intermediate Int01.01

Ethyl [(5-bromopyridin-2-yl)carbamothioyl]carbamate

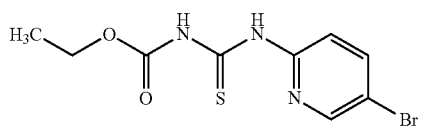 [SMILES: CCOC(=O)NC(=S)Nc1ccc(Br)cn1]

Ethoxycarbonylisothiocyanate (16.7 g) was added to a stirred solution of 2-amino-5-brompyridine (20 g) in dioxane (200 mL). The mixture was stirred for 2 h at r.t. A white solid precipitated. Hexane (20 mL) was added and the white solid was collected by filtration.

Yield: 30.4 g of the title compound.

$^1$H-NMR (300 MHz, DMSO-d$_6$): δ [ppm]=1.22 (t, 3H), 4.19 (q, 2H), 8.08 (dd, 1H), 8.49 (d, 1H), 8.57 (br. d, 1H), 11.37-12.35 (m, 2H).

Intermediate Int03.02

1-bromo-2-methoxy-4-(methylsulfonyl)benzene

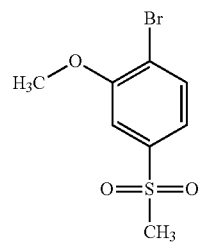

To a stirred solution of Int03.01 (265 mg) in chloroform (10 mL) was added 3-chlorobenzenecarboperoxoic acid (mCPBA) (890 mg). The mixture was stirred at room temperature for 1 h. A half-saturated solution of sodium bicarbonate was added and the mixture was extracted with dichloromethane. The organic phase was washed with saturated sodium chloride solution, dried (sodium sulfate) and the solvent was removed in vacuum. Silica gel chromatography gave 252 mg of the title compound.

$^1$H-NMR (300 MHz, DMSO-d$_6$): δ [ppm]=3.22 (s, 3H), 3.93 (s, 3H), 7.39 (dd, 1H), 7.50 (d, 1H), 7.84 (d, 1H).

Intermediate Int03.01

1-bromo-2-methoxy-4-(methylsulfanyl)benzene

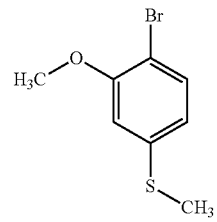

To a stirred solution of 1-bromo-4-fluoro-2-methoxybenzene (4.0 g) in DMF (40 mL) was added sodium methanethiolate (2.76 g). The mixture was stirred at room temperature for 30 minutes and at 85° C. for 2 h. Water was added and the mixture was extracted with ethyl acetate. The organic phase was washed with saturated sodium chloride solution, dried (sodium sulfate) and the solvent was removed in vacuum. Silica gel chromatography gave 280 mg of the title compound.

$^1$H-NMR (400 MHz, DMSO-d$_6$): δ [ppm]=2.46 (s, 3H), 3.82 (s, 3H), 6.74 (dd, 1H), 6.91 (d, 1H), 7.44 (d, 1H).

Intermediate Int03.00

1-bromo-2-methyoxy-4-(methylsulfanyl)benzene (Alternative Procedure)

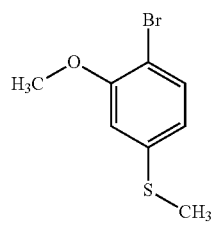

To a stirred solution of 1-bromo-4-fluoro-2-methoxybenzene (10.0 g) in DMF (100 mL) was added sodium methanethiolate (4.44 g). The mixture was stirred at 65° C. for 2 h. The mixture was cooled to 0° C. and methyl iodide (4.55 mL) was added. The mixture was stirred at room temperature for 1 h and further sodium methanethiolate (4.44 g) was added. The mixture was stirred at 65° C. for 1 h. The mixture was cooled to 0° C. and methyl iodide (4.55 mL) was added. The mixture was stirred at room temperature for 1 h. Water was added and the mixture was extracted with ethyl acetate. The organic phase was washed with saturated sodium chloride solution, dried (sodium sulfate) and the solvent was removed in vacuum. Silica gel chromatography gave 6.2 g of the title compound as a 2:1 mixture with the starting material. The mixture was used for the next step without purification.

Route II

(2R)-2-(4-fluorophenyl)-N-[4-(2-{[2-methoxy-4-(methylsulfonyl)phenyl]-amino}[1,2,4]triazolo[1,5-α]pyridin-6-yl)phenyl]propanamide

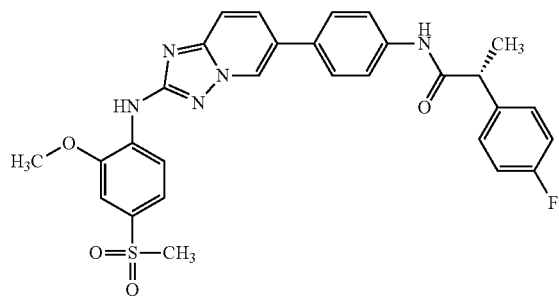 [SMILES: COc1cc(S(C)(=O)=O)ccc1Nc1nc2ccc(-c3ccc(NC(=O)[C@H](C)c4ccc(F)cc4)cc3)cn2n1]

To a stirred suspension of Int21.06 (550 mg) in toluene (18 mL) was added potassium fluoride (260 mg) and powdered potassium phosphate (842 mg) and the flask was degassed twice and backfilled with argon. The mixture was stirred for 15 minutes at r.t. Int21.03 (350 mg), dicyclohexyl (2',6'-dimethoxybiphenyl-2-yl)phosphine (81 mg) and palladium acetate (22 mg) were added and the flask was degassed twice and backfilled with argon. The mixture was heated to 85° C. for 3 h. Water was added and the reaction mixture was extracted with ethyl acetate. The organic phase was washed with saturated sodium chloride solution, dried (sodium sulfate) and the solvent was removed in vacuum. Aminophase-silica-gel chromatography gave a solid that was triturated with a mixture of dichloromethane and hexane to give 452 mg of the title compound.

$^1$H-NMR (300 MHz, DMSO-d$_6$), δ [ppm]=1.39 (3H), 3.16 (3H), 3.83 (1H), 3.95 (3H), 7.08-7.20 (2H), 7.34-7.45 (3H), 7.51 (1H), 7.63-7.77 (5H), 7.92 (1H), 8.48 (1H), 8.64 (1H), 9.11 (1H), 10.19 (1H).

$[α]_D^{20}$: −78.9° (in DMSO).

Determination of Enantiomeric Purity by Analytical Chiral HPLC:

Column: Chiralcel OD-RH 150×4.6; Flow: 1.00 mL/min; Solvent: A: Water with 0.1% formic acid, B: Acetonitrile; Solvent mixture: 40% A+60% B. Run Time: 30 min. Retention Time: 12.83 min; UV 254 nm; Enantiomeric Ratio: <1%:>99%.

Intermediate Int21.06

(2R)-2-(4-fluorophenyl)-N-[4-(4,4,5,5-tetramethyl-1,3,2-dioxaborolan-2-yl)phenyl]propanamide

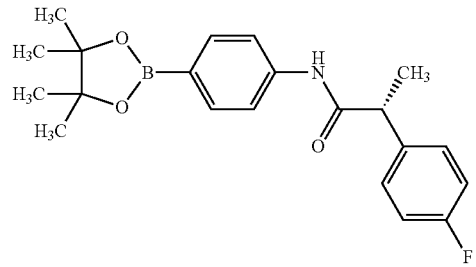 [SMILES: C[C@@H](C(=O)Nc1ccc(B2OC(C)(C)C(C)(C)O2)cc1)c1ccc(F)cc1]

To a stirred solution of 4-(4,4,5,5-tetramethyl-1,3,2-dioxaborolan-2-yl)aniline (1.0 g) in DMF (45 mL) and dichloromethane (90 mL) was added sodium bicarbonate (766 mg), Int09.03 (844 mg) and HATU (2.6 g). The mixture was stirred at room temperature for 4 h. Water was added, and the mixture was stirred for 30 minutes. A half-saturated solution of sodium bicarbonate was added and the mixture was extracted with ethyl acetate. The organic phase was washed with saturated sodium chloride solution, dried (sodium sulfate) and the solvent was removed in vacuum. Silica-gel chromatography gave 1.53 g of the title compound.

$^1$H-NMR (400 MHz, DMSO-d$_6$), δ [ppm]=1.23 (12H), 1.37 (3H), 3.74-3.87 (1H), 7.06-7.16 (2H), 7.31-7.42 (2H), 7.51-7.61 (4H), 10.12 (1H).

Intermediate Example Int21.05

(4-{[(2R)-2-(4-fluorophenyl)propanoyl]amino}phenyl)boronic acid

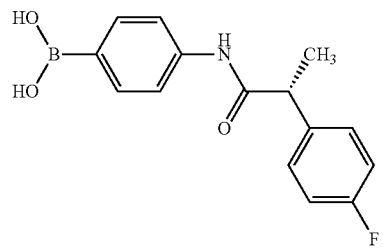 [SMILES: C[C@@H](C(=O)Nc1ccc(B(O)O)cc1)c1ccc(F)cc1]

To a stirred solution of (4-aminophenyl)boronic acid hydrochloride (2.00 g) in DMF (42 mL) was added sodium bicarbonate (2.9 g), (2R)-2-(4-fluorophenyl)propanoic acid (2.04 g) and HATU (6.58 g). The mixture was stirred at room temperature for 72 h. Water (140 mL) was added, and the mixture was stirred for 2 h. The white precipitate was collected by filtration and was washed with water and was dried in vacuum to give 2.86 g of the title compound.

$^1$H-NMR (300 MHz, DMSO-$d_6$), δ [ppm]=1.39 (3H), 3.84 (1H), 7.08-7.21 (2H), 7.35-7.44 (2H), 7.52 (2H), 7.69 (2H), 7.88 (2H), 10.07 (1H).

Intermediate Int09.03

(2R)-2-(4-fluorophenyl)propanoic acid

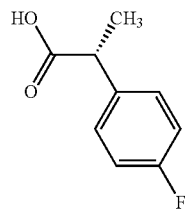

To a stirred solution of Int09.02 (23.6 g) in refluxing ethyl acetate (250 mL) was added a solution of (1S)-1-phenylethanamine (17.35 g) in ethyl acetate. The mixture was allowed to cool down to room temperature within 1 h. A white solid was collected by filtration, was washed with ethyl acetate and dried in vacuum to give 27.5 g of a solid. The solid was recrystallized from 400 mL refluxing ethyl acetate. The mixture was allowed to cool down to room temperature. A white solid was collected by filtration, was washed with ethyl acetate and dried in vacuum to give 18.3 g of a solid. The solid was twice recrystallized from refluxing ethyl acetate (350 mL; 300 mL). A white solid was collected by filtration, was washed with ethyl acetate and dried in vacuum to give 10.51 g of a solid. The solid was dissolved in water, hydrochloric acid (c=2.0 M) was added until pH 5 was reached and the reaction mixture was extracted with dichloromethane. The organic phase was dried (sodium sulfate) and the solvent was removed in vacuum to give 5.6 g of the title product. The crude product was used without further purification.

$^1$H-NMR (300 MHz, DMSO-$d_6$): δ [ppm]=1.31 (d, 3H), 3.66 (q, 1H), 7.05-7.16 (m, 2H), 7.24-7.33 (m, 2H), 12.28 (br. s., 1H).

$[\alpha]_D^{20}$: −79.3° (in DMSO)

Determination of Enantiomeric Purity by Analytical Chiral HPLC:

Column: Chiralcel OJ-H 150×4.6; Flow: 1.00 mL/min; Solvent: A: Hexane, B: 2-propanol with 0.1% formic acid; Solvent mixture: 80% A+20% B. Run Time: 30 min. Retention Time: 3.41 min; UV 254 nm; Enantiomeric Ratio: 99.8%:0.2%.

Intermediate Int09.02

Rac-2-(4-fluorophenyl)propanoic acid

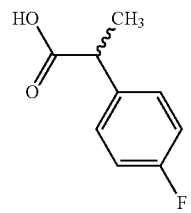

To a stirred solution of Int09.01 (18.9 g) in ethanol (200 mL) was added a solution of potassium hydroxide (35 g), dissolved in water (200 mL). The mixture was stirred at 0° C. for 4 h. Hydrochloric acid (c=4.0 M) was added until pH 5 was reached and the reaction mixture was extracted with ethyl acetate. The organic phase was separated and the solvent was removed in vacuum to give 15.64 g of the title product. The crude product was used without further purification.

$^1$H-NMR (300 MHz, DMSO-$d_6$): δ [ppm]=1.31 (d, 3H), 3.66 (q, 1H), 7.05-7.15 (m, 2H), 7.24-7.33 (m, 2H), 12.30 (s, 1H).

Intermediate Int09.01

Rac-methyl 2-(4-fluorophenyl)propanoate

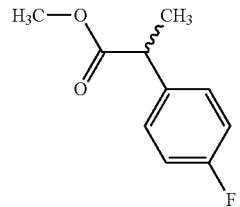

To a stirred solution of diisopropylamine (13.0 g) in tetrahydrofurane (160 mL) was added a solution of n-butyllithium in hexane (51.4 mL; c=2.5 M) at −78° C. The solution was stirred at 0° C. for 15 minutes. The solution was cooled to −78° C. and a solution of methyl (4-fluorophenyl) acetate (18.0 g), dissolved in tetrahydrofurane (40 mL) was added. The solution was stirred at −78° C. for 30 minutes. Methyl iodide (10.0 mL) was added at −78° C., and the solution was allowed to warm up to 0° C. within 1 h. Water was added and the reaction mixture was extracted with ethyl acetate. The organic phase was dried (sodium sulfate) and the solvent was removed in vacuum. Silicagel chromatography gave 18.9 g of the title compound.

$^1$H-NMR (400 MHz, DMSO-$d_6$): δ [ppm]=1.34 (d, 3H), 3.55 (s, 3H), 3.79 (q, 1H), 7.08-7.15 (m, 2H), 7.25-7.32 (m, 2H).

Intermediate Int21.03

6-chloro-N-[2-methoxy-4-(methylsulfonyl)phenyl][1,2,4]triazolo[1,5-α]pyridin-2-amine

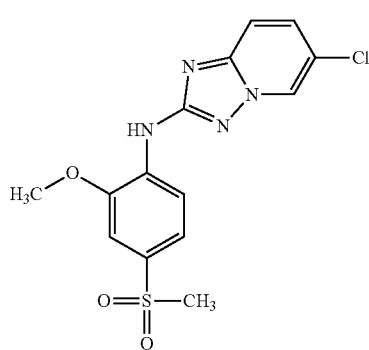 [SMILES: COc1cc(S(C)(=O)=O)ccc1Nc1nc2ccc(Cl)cn2n1]

To a stirred suspension of Int21.02 (0.7 g) in toluene (28 mL) was added Int03.02 (1.27 g), chloro(2-dicyclohexylphosphino-2',4',6'-tri-isopropyl-1,1'-biphenyl)[2-(2-aminoethyl)phenyl]palladium(II) methyl-tert-butylether adduct (343 mg), X-Phos (202 mg) and powdered potassium phosphate (3.09 g). The flask was degassed twice and backfilled with argon. The mixture was heated to reflux for 3 h. Further chloro(2-dicyclohexylphosphino-2',4',6'-tri-isopropyl-1,1'-biphenyl)[2-(2-aminoethyl)phenyl]palladium(II) methyl-tert-butylether adduct (30 mg) and X-Phos (19 mg) were added and the mixture was heated to reflux for 15 h. The solvent was removed in vacuum. Silicagel chromatography gave a solid that was triturated ethyl acetate to give 1.0 g of the title compound.

$^1$H-NMR (400 MHz, DMSO-$d_6$): δ [ppm]=3.16 (3H), 3.95 (3H), 7.42 (1H), 7.50 (1H), 7.62-7.69 (2H), 8.41 (1H), 8.70 (1H), 9.17 (1H).

Intermediate Int21.02

6-chloro[1,2,4]triazolo[1,5-α]pyridin-2-amine

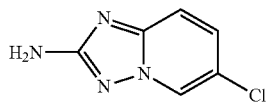 [SMILES: Nc1nc2ccc(Cl)cn2n1]

Hydroxylammonium chloride (4.4 g) was suspended in methanol (35 mL) and ethanol (35 mL) and Hünig Base (10.2 mL) was added at r.t. The mixture was heated to 60° C., Int21.01 (4.4 g) was added portionwise, and the mixture was stirred at 60° C. for 2 h. The solvent was removed in vacuum and water (150 mL) was added. A solid was collected by filtration and was washed with water and dried in vacuum.

Yield: 2.0 g of the title compound.

$^1$H-NMR (300 MHz, DMSO-$d_6$): δ [ppm]=6.09 (2H), 7.28-7.37 (1H), 7.39-7.49 (1H), 8.84 (1H).

Intermediate Int21.01

Ethyl [(5-chloropyridin-2-yl)carbamothioyl]carbamate

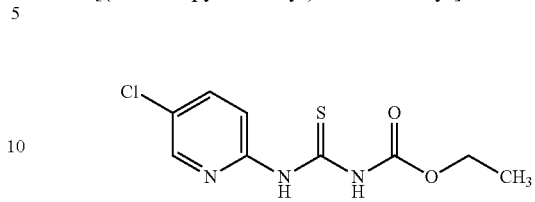

Ethoxycarbonylisothiocyanate (3.37 g) was added to a stirred solution of 2-amino-5-cloropyridine (3.0 g) in dioxane (100 mL). The mixture was stirred at r.t. for 14 h. The solvent was removed in vacuum. The solid was dissolved in dichloromethane and methanol (100:1), filtered and the solvent was removed in vacuum to give a solid that was recystallized from ethyl acetate to give 4.4 g of the title compound.

$^1$H-NMR (400 MHz, CHLOROFORM-d): δ [ppm]=1.35 (3H), 4.31 (2H), 7.71 (1H), 8.03 (1H), 8.34 (1H), 8.83 (1H), 12.09 (1H).

Preparation of Compound A2

(2R)-2-(4-fluorophenyl)-N-[4-(2-{[4-(methylsulfonyl)-2-(2,2,2-trifluoro-ethoxy)phenyl]amino}[1,2,4]triazolo[1,5-α]pyridin-6-yl)phenyl]-propanamide

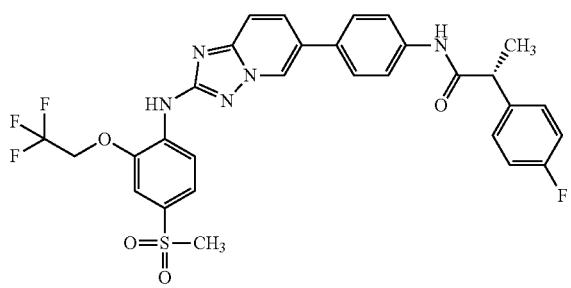 [SMILES: C[C@@H](C(=O)Nc1ccc(-c2ccc3nc(Nc4ccc(S(C)(=O)=O)cc4OCC(F)(F)F)nn3c2)cc1)c1ccc(F)cc1]

To a stirred suspension of Int08.021 (5.6 g) in DMF (45 mL) and dichloromethane (90 mL) was added sodium bicarbonate (1.97 g), (2R)-2-(4-fluorophenyl)propanoic acid (2.17 g) and HATU (6.69 g). The mixture was stirred at room temperature for 4 h. Water was added, and the mixture was stirred for 30 minutes. A half-saturated solution of sodium bicarbonate was added and the mixture was extracted with ethyl acetate. The organic phase was washed with saturated sodium chloride solution, dried (sodium sulfate) and the solvent was removed in vacuum. Aminophase-silica-gel chromatography gave a solid that was triturated with a mixture of ethyl acetate and cyclohexane to give 6.60 g of the title compound.

$^1$H-NMR (300 MHz, DMSO-$d_6$): δ [ppm]=1.39 (d, 3H), 3.17 (s, 3H), 3.83 (q, 1H), 5.00 (q, 2H), 7.08-7.19 (m, 2H), 7.35-7.45 (m, 2H), 7.58-7.76 (m, 7H), 7.93 (dd, 1H), 8.50 (d, 1H), 8.59 (s, 1H), 9.11 (d, 1H), 10.19 (s, 1H).

$[α]_D^{20}$: −69.3° (in DMSO).

Determination of Enantiomeric Purity by Analytical Chiral HPLC:

Column: Chiralcel OD-RH 150×4.6; Flow: 1.00 mL/min; Solvent: A: Water with 0.1% formic acid, B: Acetonitrile;

Solvent mixture: 40% A+60% B. Run Time: 20 min. Retention Time: 12.28 min; UV 254 nm; Enantiomeric Ratio: <1%:>99%.

Intermediate Example Int08.021

6-(4-aminophenyl)-N-[4-(methylsulfonyl)-2-(2, 2, 2-trifluoroethoxy)phenyl]-[1,2,4]triazolo[1,5-α]pyridin-2-amine

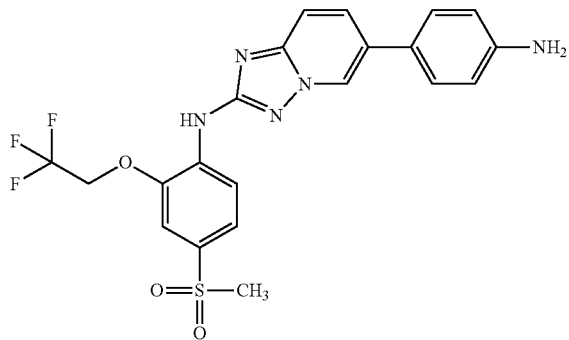 [SMILES: CS(=O)(=O)c1ccc(Nc2nc3ccc(-c4ccc(N)cc4)cn3n2)c(OCC(F)(F)F)c1]

To a stirred suspension of Int08.020 (11.9 g) in dichloromethane (80 mL) was added TFA (40 mL). The mixture was stirred at room temperature for 24 h. The solvent was removed in vacuum, and the residue was dissolved in ethyl acetate. A half-saturated solution of sodium bicarbonate was added until pH 9 was reached. The precipitated solid was collected by filtration to give 9.7 g of the title compound.

$^1$H-NMR (400 MHz, DMSO-$d_6$): δ [ppm]=3.16 (s, 3H), 5.00 (q, 2H), 5.34 (br. s., 2H), 6.60-6.68 (m, 2H), 7.39-7.48 (m, 2H), 7.57-7.66 (m, 3H), 7.85 (dd, 1H), 8.48 (s, 1H), 8.51 (d, 1H), 8.89-8.96 (m, 1H).

Intermediate Example Int08.020 tert-butyl [4-(2-{[4-(methylsulfonyl)-2-(2, 2, 2-trifluoroethoxy)phenyl]-amino}[1,2,4]triazolo[1,5-α]pyridin-6-yl)phenyl]carbamate

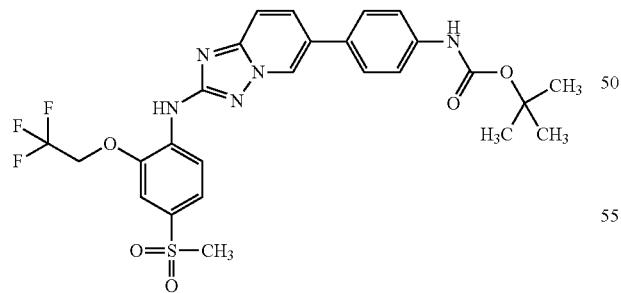

To a stirred suspension of Int01.03 (4.0 g) in toluene (77 mL) and NMP (7.7 mL) was added Int05.03 (4.91 g), chloro(2-dicyclohexylphosphino-2',4',6'-triisopropyl-1,1'-biphenyl)[2-(2-aminoethyl)phenyl]palladium(II) methyl-tert-butylether adduct (254 mg) and X-Phos (150 mg) and the flask was degassed twice and backfilled with argon. The mixture was stirred for 5 minutes at room temperature. Powdered potassium phosphate (9.13 g) was added and the flask was degassed twice and backfilled with argon. The mixture was heated to reflux for 1 h. The reaction mixture was filtered through an aminophase-silica-gel column and the solvent was removed in vacuum. Aminophase-silica-gel chromatography gave a solid that was triturated with a mixture of hexane and dichloromethane to give 6.05 g of the title compound.

$^1$H-NMR (400 MHz, DMSO-$d_6$): δ [ppm]=1.46 (s, 9H), 3.17 (s, 3H), 5.00 (q, 2H), 7.55 (d, 2H), 7.60-7.71 (m, 5H), 7.93 (dd, 1H), 8.50 (d, 1H), 8.54 (s, 1H), 9.09 (dd, 1H), 9.46 (s, 1H).

Intermediate Example Int05.03

1-bromo-4-(methylsulfonyl)-2-(2,2,2-trifluoroethoxy)benzene

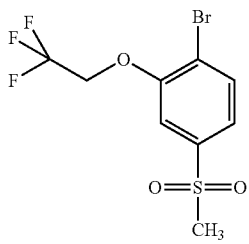 [SMILES: CS(=O)(=O)c1ccc(Br)c(OCC(F)(F)F)c1]

To a stirred solution of Int05.02 (3.8 g) in chloroform (100 mL) was added 3-chlorobenzenecarboperoxoic acid (mCPBA) (8.48 g). The mixture was stirred at room temperature for 16 h. With ice bath cooling, a half-saturated solution of sodium bicarbonate and a 0.2 M solution of sodium thiosulfate was added, the mixture was stirred for 30 minutes and the mixture was extracted with dichloromethane. The organic phase was washed with a 0.2 M solution of sodium thiosulfate and a saturated sodium chloride solution, dried (sodium sulfate) and the solvent was removed in vacuum. Silica gel chromatography gave a solid that was triturated with ether to give 2.1 g of the title compound.

$^1$H-NMR (400 MHz, CHLOROFORM-d): δ [ppm]=3.06 (s, 3H), 4.50 (q, 2H), 7.45 (d, 1H), 7.52 (dd, 1H), 7.81 (d, 1H).

Intermediate Example Int05.02

1-bromo-4-(methylsulfanyl)-2-(2, 2, 2-trifluoroethoxy)benzene

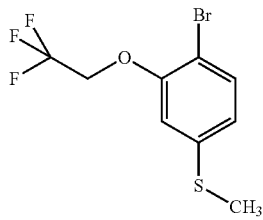

To a stirred solution of Int05.01 (4.0 g) in DMF (15 mL) was added sodium methanethiolate (1.0 g). The mixture was stirred for 2 h at 60° C. The mixture was cooled to room temperature. Water was added and the mixture was extracted with ethyl acetate. The organic phase was washed with saturated sodium chloride solution, dried (sodium sulfate) and the solvent was removed in vacuum to give 3.8 g of the crude title compound, that was used for the next step without purification.

¹H-NMR (300 MHz, CHLOROFORM-d): δ [ppm]=2.48 (s, 3H), 4.39 (q, 2H), 6.78-6.88 (m, 2H), 7.46 (d, 1H).

Intermediate Example Int05.01

1-bromo-4-fluoro-2-(2,2,2-trifluoroethoxy)benzene

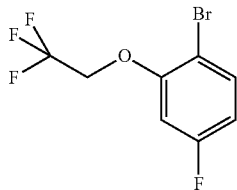 [SMILES: Fc1ccc(Br)c(OCC(F)(F)F)c1]

To a stirred solution of 2-bromo-5-fluorophenol (1.5 g) in acetonitrile (0.5 mL) and DMF (8.5 mL) in a microwave tube was added potassium carbonate (2.1 g) and 2,2,2-trifluoroethyl trifluoromethanesulfonate (2.37 g). The mixture was heated to 150° C. in a microwave oven for 30 minutes. In a second microwave tube the same reaction was repeated. Both mixtures were combined. The solvent was removed in vacuum, ethyl acetate and hexane (1:1) was added and the mixture was washed with water. The organic phase was washed with saturated sodium chloride solution, dried (sodium sulfate) and the solvent was removed in vacuum. Silica gel chromatography gave 4.0 g of the title compound.

¹H-NMR (300 MHz, CHLOROFORM-d): δ [ppm]=4.39 (q, 2H), 6.62-6.78 (m, 2H), 7.53 (dd, 1H).

Intermediate Example Int05.04

6-chloro-N-[4-(methylsulfonyl)-2-(2,2,2-trifluoroethoxy)phenyl][1,2,4]triazolo[1,5-α]pyridin-2-amine

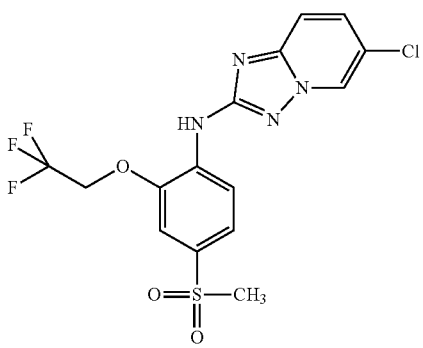 [SMILES: CS(=O)(=O)c1ccc(Nc2nc3ccc(Cl)cn3n2)c(OCC(F)(F)F)c1]

Starting with Intermediate Int21.02 (1.4 g) and Intermediate Example Int05.03 (3.18 g) Intermediate Example Int05.04 was prepared analogously to the procedure for the preparation of Intermediate Int21.03.

Yield: 3.49 g of the title compound.

Preparation of Compound A3

(2R)-N-{4-[2-({4-[(3-fluoroazetidin-1-yl)carbonyl]-2-methoxyphenyl}amino)-[1,2,4]triazolo[1,5-α]pyridin-6-yl]phenyl}-2-(4-fluorophenyl)propanamide

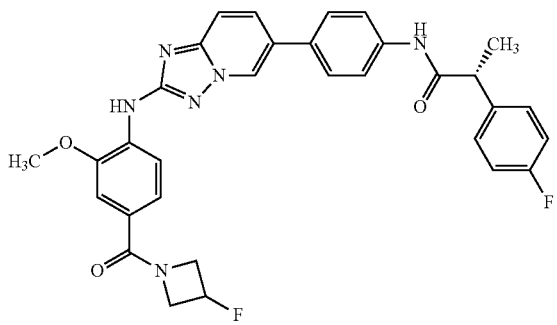 [SMILES: COc1cc(C(=O)N2CC(F)C2)ccc1Nc1nc2ccc(-c3ccc(NC(=O)[C@H](C)c4ccc(F)cc4)cc3)cn2n1]

To a stirred suspension of Int08.061 (1.10 g) in DMF (8.5 mL) and dichloromethane (17 mL) was added sodium bicarbonate (427 mg), (2R)-2-(4-fluorophenyl)propanoic acid (470 mg) and HATU (1.45 g). The mixture was stirred at room temperature for 4 h. Water was added, and the mixture was stirred for 30 minutes. A half-saturated solution of sodium bicarbonate was added and the mixture was extracted with ethyl acetate. The organic phase was washed with saturated sodium chloride solution, dried (sodium sulfate) and the solvent was removed in vacuum. Amino-phase-silica-gel chromatography gave 1.13 g of the title compound.

¹H-NMR (400 MHz, DMSO-d₆): δ [ppm]=1.42 (d, 3H), 3.86 (q, 1H), 3.93 (s, 3H), 3.98-4.80 (m, 4H), 5.44 (m, 1H, J=57.5 Hz), 7.12-7.20 (m, 2H), 7.26 (d, 1H), 7.30 (dd, 1H), 7.40-7.46 (m, 2H), 7.63-7.76 (m, 5H), 7.93 (dd, 1H), 8.31-8.39 (m, 2H), 9.11 (d, 1H), 10.19 (s, 1H).

$[\alpha]_D^{20}$: −70.0° (in DMSO).

Determination of Enantiomeric Purity by Analytical Chiral HPLC:

Column: Chiralcel OD-RH 150×4.6; Flow: 1.00 mL/min; Solvent: A: Water with 0.1% formic acid, B: Acetonitrile; Solvent mixture: 40% A+60% B. Run Time: 20 min. Retention Time: 13.88 min; UV 254 nm; Enantiomeric Ratio: <1%:>99%.

Intermediate Example Int08.061

(4-{[6-(4-aminophenyl)[1,2,4]triazolo[1,5-α]pyridin-2-yl]amino}-3-methoxyphenyl)(3-fluoroazetidin-1-yl)methanone

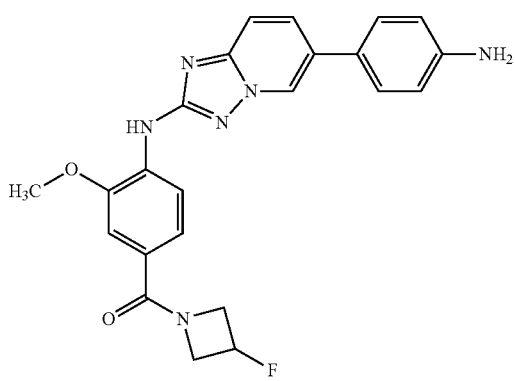 [SMILES: COc1cc(C(=O)N2CC(F)C2)ccc1Nc1nc2ccc(-c3ccc(N)cc3)cn2n1]

To a stirred suspension of Int08.060 (7.8 g) in dichloromethane (55 mL) was added TFA (28 mL). The mixture was stirred at room temperature for 16 h. The solvent was removed in vacuum and the residue was dissolved in ethyl acetate. A saturated solution of sodium bicarbonate was added until pH 9 was reached. The precipitated solid was collected by filtration to give 5.2 g of the title compound. The crude product was used for the next step without further purification.

$^1$H-NMR (300 MHz, DMSO-$d_6$): δ [ppm]=3.90 (s, 3H), 4.45 (br. s., 4H), 5.20-5.58 (m, 3H), 6.63 (d, 2H), 7.23 (d, 1H), 7.27 (dd, 1H), 7.42 (d, 2H), 7.52-7.61 (m, 1H), 7.81 (dd, 1H), 8.23 (s, 1H), 8.34 (d, 1H), 8.86-8.94 (m, 1H).

Intermediate Example Int08.060 tert-butyl {4-[2-({4-[(3-fluoroazetidin-1-yl)carbonyl]-2-methoxyphenyl}-amino)[1,2,4]triazolo[1,5-α]pyridin-6-yl]phenyl}carbamate

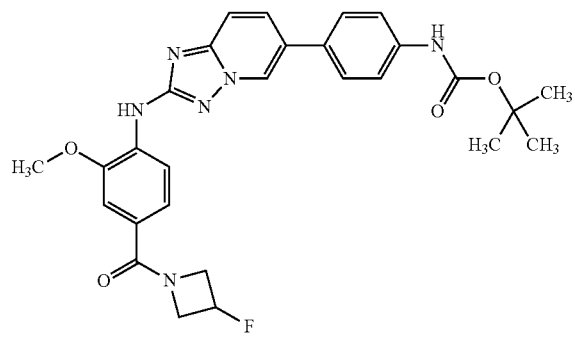 [SMILES: COc1cc(C(=O)N2CC(F)C2)ccc1Nc1nc2ccc(-c3ccc(NC(=O)OC(C)(C)C)cc3)cn2n1]

To a stirred suspension of Int01.03 (6.0 g) in toluene (350 mL) and NMP (29 mL) was added Int02.05 (6.91 g), chloro(2-dicyclohexylphosphino-2',4',6'-triisopropyl-1,1'-biphenyl)[2-(2-aminoethyl)phenyl]palladium(II) methyl-tert-butylether adduct (610 mg) and X-Phos (359 mg) and the flask was degassed twice and backfilled with argon. The mixture was stirred for 5 minutes at room temperature. Powdered potassium phosphate (13.7 g) was added and the flask was degassed twice and backfilled with argon. The mixture was heated to reflux for 1 h. The reaction mixture was filtered through an aminophase-silica-gel column and the solvent was removed in vacuum. Aminophase-silica-gel chromatography gave 7.9 g of the title compound.

$^1$H-NMR (300 MHz, DMSO-$d_6$): δ [ppm]=1.46 (s, 9H), 3.90 (s, 3H), 4.04-4.80 (m, 4H), 5.27-5.57 (m, 1H), 7.23 (d, 1H), 7.27 (dd, 1H), 7.54 (d, 2H), 7.59-7.71 (m, 3H), 7.89 (dd, 1H), 8.29 (s, 1H), 8.34 (d, 1H), 9.06 (d, 1H), 9.45 (s, 1H).

Intermediate Example Int02.05

(4-Bromo-3-methoxyphenyl)(3-fluoroazetidin-1-yl)methanone

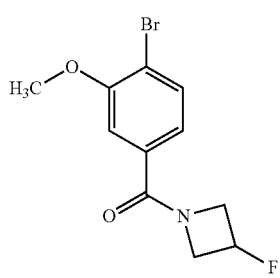 [SMILES: COc1cc(C(=O)N2CC(F)C2)ccc1Br]

To a stirred solution of 4-bromo-3-methoxybenzoic acid (1.4 g) in DMF (15 mL) was added potassium carbonate (2.51 g), 3-fluoroazetidine hydrochloride (1.01 g) and HATU (3.69 g). The mixture was stirred at room temperature for 18 h. Water was added, the mixture was stirred for 15 minutes and the solvent was removed in vacuum. Water was added and the mixture was extracted with ethyl acetate. The organic phase was washed with water, saturated sodium chloride solution, dried (sodium sulfate) and the solvent was removed in vacuum, to give 1.25 g of the title compound.

$^1$H-NMR (400 MHz, DMSO-$d_6$): δ [ppm]=3.90 (s, 3H), 3.99-4.16 (m, 1H), 4.31-4.65 (m, 3H), 5.36 (tt, 0.5H), 5.50 (tt, 0.5H), 7.14 (dd, 1H), 7.26 (d, 1H), 7.66 (d, 1H).

Preparation of Compound A4

(2R)-N-[4-(2-{[4-(azetidin-1-ylcarbonyl)-2-methoxyphenyl]amino}[1,2,4]-triazolo[1,5-α]pyridin-6-yl)phenyl]-2-(4-fluorophenyl)propanamide

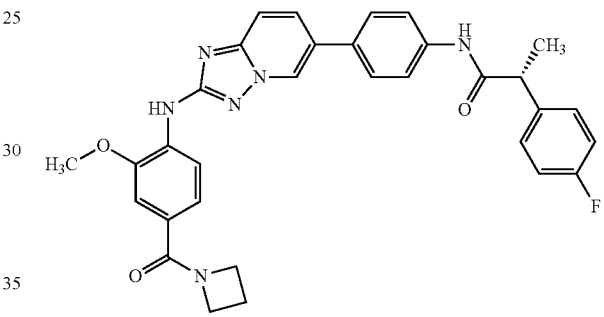

To a stirred suspension of Int08.071 (200 mg) in DMF (1.6 mL) and dichloromethane (3.2 mL) was added sodium bicarbonate (122 mg), (2R)-2-(4-fluorophenyl)propanoic acid (89 mg) and HATU (275 mg). The mixture was stirred at room temperature for 4 h. Water was added, and the mixture was stirred for 30 minutes. A half-saturated solution of sodium bicarbonate was added and the mixture was extracted with a mixture of dichloromethane and methanol (100:1). The organic phase was washed with saturated sodium chloride solution, dried (sodium sulfate) and the solvent was removed in vacuum. Aminophase-silica-gel chromatography followed by silica gel chromatography gave a solid that was triturated with ether to give 250 mg of the title compound.

$^1$H-NMR (300 MHz, DMSO-$d_6$): δ [ppm]=1.39 (d, 3H), 2.22 (quin, 2H), 3.78-3.92 (m, 4H), 4.00 (br. s., 2H), 4.32 (br. s, 2H), 7.09-7.17 (m, 2H), 7.20-7.26 (m, 2H), 7.36-7.44 (m, 2H), 7.59-7.75 (m, 5H), 7.89 (dd, 1H), 8.24-8.36 (m, 2H), 9.08 (d, 1H), 10.18 (s, 1H).

$[α]_D^{20}$: −63.5° (in DMSO).

Determination of Enantiomeric Purity by Analytical Chiral HPLC:

Column: Chiralcel OD-RH 150×4.6; Flow: 1.00 mL/min; Solvent: A: Water with 0.1% formic acid, B: Acetonitrile; Solvent mixture: 40% A+60% B. Run Time: 30 min. Retention Time: 14.22 min; UV 254 nm; Enantiomeric Ratio: <2%:>98%.

Intermediate Example Int08.071

(4-{[6-(4-aminophenyl)[1,2,4]triazolo[1,5-α]pyridin-2-yl]amino}-3-methoxyphenyl)(azetidin-1-yl)methanone

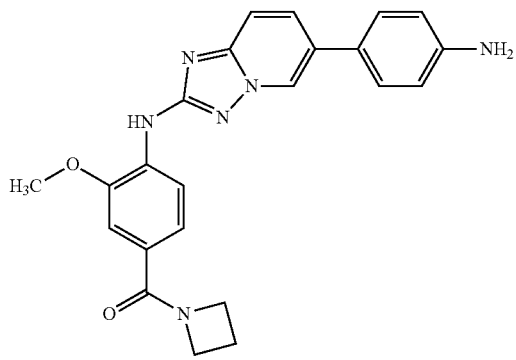 [SMILES: COc1cc(C(=O)N2CCC2)ccc1Nc1nc2ccc(-c3ccc(N)cc3)cn2n1]

To a stirred suspension of Int08.070 (600 mg) in dichloromethane (12 mL) was added TFA (2.2 mL). The mixture was stirred at room temperature for 16 h. A saturated solution of potassium carbonate was added until pH 9 was reached. The mixture was extracted with dichloromethane and methanol (10:1 mixture). The reaction mixture was filtered through an aminophase-silica-gel column and the solvent was removed in vacuum. The residue was triturated with ethanol to give 475 mg of the title compound.

$^1$H-NMR (300 MHz, DMSO-$d_6$): δ [ppm]=2.23 (quin, 2H), 3.88 (s, 3H), 4.00 (br. s., 2H), 4.33 (br. s., 2H), 5.30 (s, 2H), 6.62 (d, 2H), 7.18-7.28 (m, 2H), 7.42 (d, 2H), 7.57 (d, 1H), 7.81 (dd, 1H), 8.23 (s, 1H), 8.32 (d, 1H), 8.90 (d, 1H).

Intermediate Example Int08.070 tert-butyl [4-(2-{[4-(azetidin-1-ylcarbonyl)-2-methoxyphenyl]amino}-[1,2,4]triazolo[1,5-α]pyridin-6-yl)phenyl]carbamate

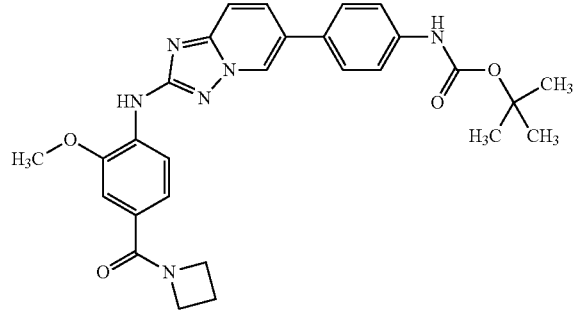 [SMILES: COc1cc(C(=O)N2CCC2)ccc1Nc1nc2ccc(-c3ccc(NC(=O)OC(C)(C)C)cc3)cn2n1]

To a stirred suspension of Int01.03 (672 mg) in toluene (13 mL) and NMP (1.3 mL) was added Int02.04 (670 mg), chloro(2-dicyclohexylphosphino-2',4',6'-tri-isopropyl-1,1'-biphenyl)[2-(2-aminoethyl)phenyl]palladium(II) methyl-tert-butylether adduct (85 g), X-Phos (50 mg) and powdered potassium phosphate (1.32 g). The flask was degassed twice and backfilled with argon. The mixture was heated to reflux for 16 h. Aminophase-silica-gel chromatography of the crude mixture gave 600 mg of the title compound, which contained a small amount of Int08.071. The crude product was used for the next step without further purification.

Intermediate Example Int02.04 azetidin-1-yl(4-bromo-3-methoxyphenyl)methanone

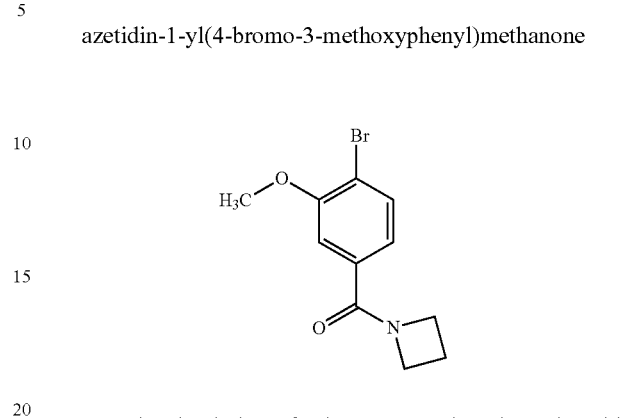

To a stirred solution of 4-bromo-3-methoxybenzoic acid (400 mg) in DMF (4.0 mL) was added potassium carbonate (720 mg), azetidine (148 mg) and TBTU (890 mg). The mixture was stirred at room temperature for 60 h. Water was added, the mixture was stirred for 15 minutes and the solvent was removed in vacuum. Water was added and the mixture was extracted with ethyl acetate. The organic phase was washed with saturated sodium chloride solution, dried (sodium sulfate) and the solvent was removed in vacuum. Silica gel chromatography gave 370 mg of the title compound.

$^1$H-NMR (400 MHz, DMSO-$d_6$): δ [ppm]=2.15-2.27 (m, 2H), 3.85 (s, 3H), 4.00 (t, 2H), 4.26 (t, 2H), 7.07 (dd, 1H), 7.21 (d, 1H), 7.61 (d, 1H).

Preparation of Compound A5

(2R)-N-{4-[2-({4-[(3-fluoroazetidin-1-yl)carbonyl]-2-(2,2,2-trifluoroethoxy)phenyl}amino)[1,2,4]triazolo[1,5-α]pyridin-6-yl]phenyl}-2-(4-fluorophenyl)propanamide

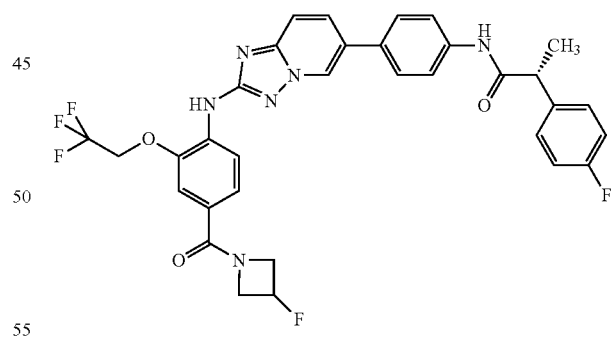

To a stirred suspension of Int08.111 (300 mg) in DMF (6.0 mL) and dichloromethane (12 mL) was added sodium bicarbonate (151 mg), (2R)-2-(4-fluorophenyl)propanoic acid (111 mg) and HATU (296 mg). The mixture was stirred at room temperature for 4 h. Water was added, and the mixture was stirred for 30 minutes. A half-saturated solution of sodium bicarbonate was added and the mixture was extracted with a mixture of dichloromethane and methanol (100:1). The organic phase was washed with saturated sodium chloride solution, dried (sodium sulfate) and the solvent was removed in vacuum. Aminophase-silica-gel chromatography followed by silica-gel chromatography gave a solid that was triturated with ethanol to give 240 mg of the title compound.

$^1$H-NMR (300 MHz, DMSO-d$_6$): δ [ppm]=1.39 (d, 3H), 3.83 (q, 1H), 3.91-4.73 (m, 4H), 4.92 (d, 2H), 5.25-5.58 (m, 1H), 7.13 (t, 2H), 7.33-7.46 (m, 4H), 7.59-7.76 (m, 5H), 7.91 (dd, 1H), 8.27 (s, 1H), 8.32-8.40 (m, 1H), 9.10 (s, 1H), 10.18 (s, 1H).

Determination of Enantiomeric Purity by Analytical Chiral HPLC:

Column: Chiralcel OD-RH 150×4.6; Flow: 1.00 mL/min; Solvent: A: Water with 0.1% formic acid, B: Acetonitrile; Solvent mixture: 40% A+60% B. Run Time: 30 min. Retention Time: 12.44 min; UV 254 nm; Enantiomeric Ratio: <2%:>98%.

Intermediate Example Int08.111

[4-{[6-(4-aminophenyl)[1,2,4]triazolo[1,5-α]pyridin-2-yl]amino}-3-(2,2,2-trifluoroethoxy)phenyl](3-fluoroazetidin-1-yl)methanone

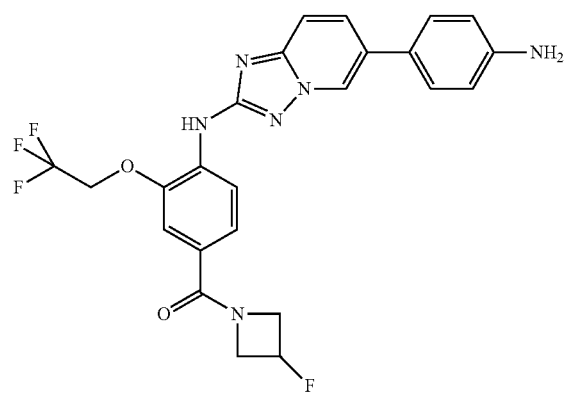 [SMILES: Nc1ccc(-c2ccc3nc(Nc4ccc(C(=O)N5CC(F)C5)cc4OCC(F)(F)F)nn3c2)cc1]

Starting with Int08.110, Int08.111 was prepared analogously to the procedure for the preparation of Int08.071.

Intermediate Example Int08.110 tert-butyl {4-[2-({4-[(3-fluoroazetidin-1-yl)carbonyl]-2-(2,2,2-trifluoroethoxy)phenyl}amino)[1,2,4]triazolo[1,5-α]pyridin-6-yl]phenyl}carbamate

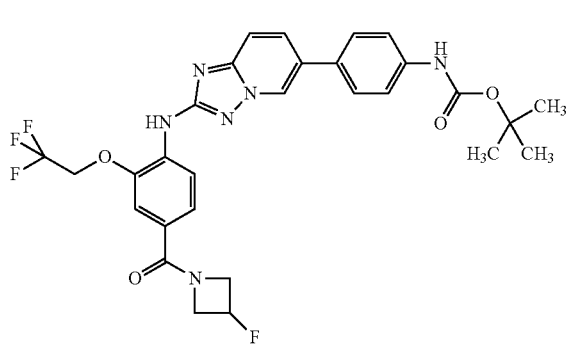 [SMILES: CC(C)(C)OC(=O)Nc1ccc(-c2ccc3nc(Nc4ccc(C(=O)N5CC(F)C5)cc4OCC(F)(F)F)nn3c2)cc1]

To a stirred suspension of Int01.03 in toluene (12 mL) and NMP (0.6 mL) was added Int06.04, chloro(2-dicyclohexylphosphino-2',4',6'-triisopropyl-1,1'-biphenyl)[2-(2-aminoethyl)phenyl]palladium(II) methyl-tert-butylether adduct, X-Phos and powdered potassium phosphate. The flask was degassed twice and backfilled with argon. The mixture was heated to reflux for 16 h. The solvent was removed in vacuum. Aminophase-silica-gel chromatography gave a solid that was triturated with ether.

Intermediate Example Int06.04

[4-bromo-3-(2,2,2-trifluoroethoxy)phenyl](3-fluoroazetidin-1-yl)methanone

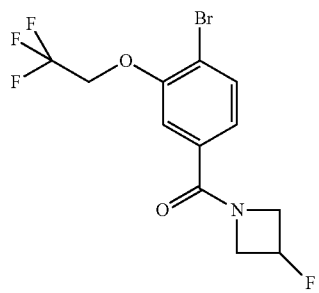 [SMILES: O=C(c1ccc(Br)c(OCC(F)(F)F)c1)N1CC(F)C1]

To a stirred solution of 4-bromo-3-(2,2,2-trifluoroethoxy) benzoic acid in DMF (15 mL) was added potassium carbonate (2.51 g), 3-fluoroazetidine hydrochloride and HATU (3.69 g). The mixture was stirred at room temperature for 18 h. Water was added, the mixture was stirred for 15 minutes and the solvent was removed in vacuum. Water was added and the mixture was extracted with ethyl acetate. The organic phase was washed with water, saturated sodium chloride solution, dried (sodium sulfate) and the solvent was removed in vacuum.

Intermediate Example Int06.05

{4-[(6-chloro[1,2,4]triazolo[1,5-α]pyridin-2-yl)amino]-3-(2,2,2-trifluoroethoxy)phenyl}(3-fluoroazetidin-1-yl)methanone

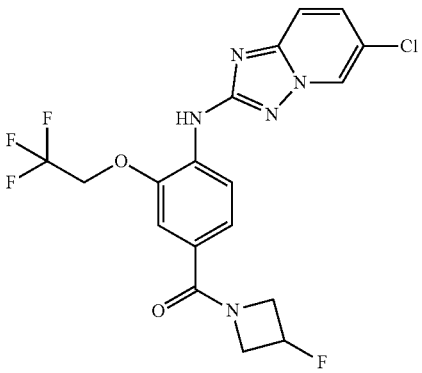 [SMILES: O=C(c1ccc(Nc2nc3ccc(Cl)cn3n2)c(OCC(F)(F)F)c1)N1CC(F)C1]

Starting with Intermediate Int21.02 (280 g) and Intermediate Example Int06.04 (680 mg), Intermediate Example Int06.05 was prepared analogously to the procedure for the preparation of Intermediate Int21.03.

Yield: 548 mg of the title compound.

Intermediate Example IntP01.01 chloromethyl (6-chloro[1,2,4]triazolo[1,5-α]pyridin-2-yl)[2-methoxy-4-(methylsulfonyl)phenyl]carbamate

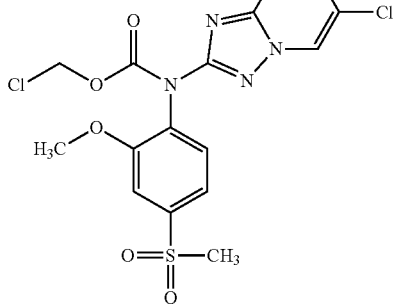

To a stirred solution of 6-chloro-N-[2-methoxy-4-(methylsulfonyl)phenyl][1,2,4]triazolo[1,5-α]pyridin-2-amine (Int21.03) (2.00 g) in THF (100 mL) was added sodium hydride (55% w/w in oil; 1.24 g) at room temperature and the mixture was stirred at 0° C. for 15 minutes. Chloromethyl chloroformate (1.29 mL) was added and the mixture was stirred at room temperature for 2 hours. A half-saturated solution of sodium chloride was added and the mixture was extracted with ethyl acetate. The organic phase was dried (sodium sulfate) and the solvent was removed in vacuum. Silicagel chromatography gave 1.66 g of the title compound.

Intermediate Example IntP01.02

1-tert-butyl 4-[({(6-chloro[1,2,4]triazolo[1,5-α]pyridin-2-yl)[2-methoxy-4-(methylsulfonyl)phenyl]carbamoyl}oxy)methyl]piperidine-1,4-dicarboxylate

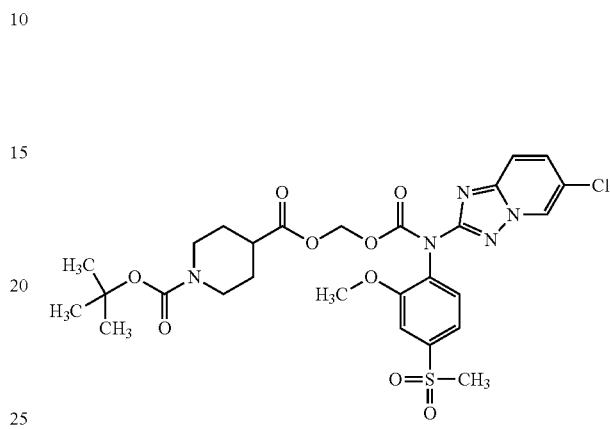

To a stirred solution of chloromethyl (6-chloro[1,2,4]triazolo[1,5-α]pyridin-2-yl)[2-methoxy-4-(methylsulfonyl)phenyl]carbamate (200 mg) in DMF (10 mL) was added 1-(tert-butoxycarbonyl)piperidine-4-carboxylic acid (257 mg) and cesium carbonate (731 mg). The mixture was stirred at room temperature for 3 h. Water was added, the mixture was extracted with ethyl acetate. The organic phase was washed with saturated sodium chloride solution, dried (sodium sulfate) and the solvent was removed in vacuum. Silicagel chromatography gave 250 mg of the title compound.

Intermediate Example IntP01.03

(2R)-2-(4-fluorophenyl)-N-[4-(2-{[2-methoxy-4-(methylsulfonyl)phenyl]amino}[1,2,4]triazolo[1,5-α]pyridin-6-yl)phenyl]propanamide

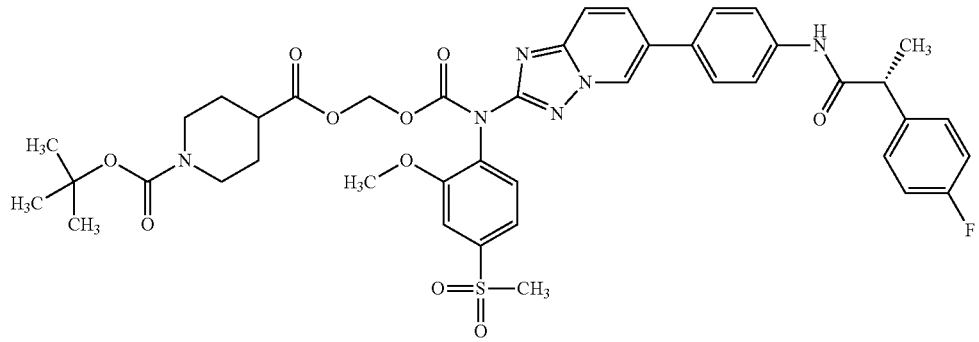 [SMILES: COc1cc(S(C)(=O)=O)ccc1N(C(=O)OCOC(=O)C1CCN(C(=O)OC(C)(C)C)CC1)c1nc2ccc(-c3ccc(NC(=O)[C@H](C)c4ccc(F)cc4)cc3)cn2n1]

To a stirred suspension of 1-tert-butyl 4-[({(6-chloro[1,2,4]triazolo[1,5-α]pyridin-2-yl)[2-methoxy-4-(methylsulfonyl)phenyl]carbamoyl}oxy)methyl]piperidine-1,4-dicarboxylate (250 mg) in toluene (10 mL) and NMP (0.5 mL) was added (4-{[(2R)-2-(4-fluorophenyl)propanoyl]amino}phenyl)boronic acid (167 mg), powdered potassium phosphate monohydrate (329 mg), dicyclohexyl(2',6'-dimethoxybiphenyl-2-yl)phosphine (31.8 mg) and palladium acetate (8.7 mg) and the flask was degassed twice and backfilled with argon. The mixture was heated to reflux for 30 minutes. The reaction mixture was filtered and the solvent was removed in vacuum. Silicagel chromatography followed by preparative reverse phase HPLC gave 90 mg of the title compound.

Intermediate Example IntP02.01 caesium (2S)-2-[(tert-butoxycarbonyl)amino]-3-methylbutanoate

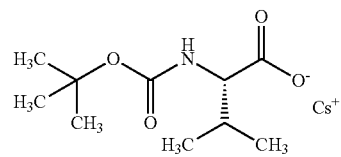

To a stirred solution of N-(tert-butoxycarbonyl)-L-valine (400 mg) in methanol (7.6 mL) was added a solution of caesium carbonate in water until pH 7 was reached (approx. 300 mg caesium carbonate in 1.52 mL water) and the solution was stirred for 30 minutes. The solvent was removed in vacuum, toluene was added and the solvent was again removed in vacuum to give 644 mg of the title compound.

Intermediate Example IntP02.02

({(6-chloro[1,2,4]triazolo[1,5-α]pyridin-2-yl)[2-methoxy-4-(methylsulfonyl)phenyl]carbamoyl}oxy)methyl N-(tert-butoxycarbonyl)-L-valinate

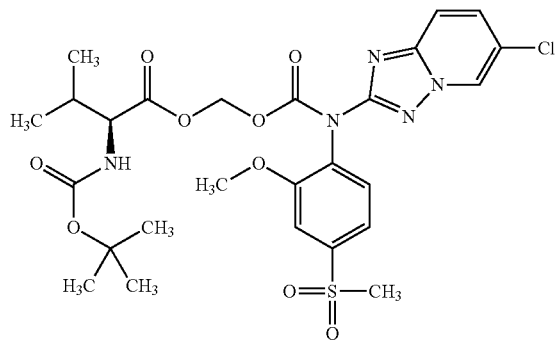 [SMILES: COc1cc(S(C)(=O)=O)ccc1N(C(=O)OCOC(=O)[C@@H](NC(=O)OC(C)(C)C)C(C)C)c1nc2ccc(Cl)cn2n1]

To a stirred solution of chloromethyl (6-chloro[1,2,4]triazolo[1,5-α]pyridin-2-yl)[2-methoxy-4-(methylsulfonyl)phenyl]carbamate (500 mg) in DMF (25 mL) was added caesium (2S)-2-[(tert-butoxycarbonyl)amino]-3-methylbutanoate (627 mg) and the mixture was stirred at room temperature for 16 h. Water was added, the mixture was extracted with ethyl acetate. The organic phase was washed with saturated sodium chloride solution, dried (sodium sulfate) and the solvent was removed in vacuum. Silicagel chromatography gave 568 mg of the title compound.

Intermediate Example IntP02.03

({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)methyl N-(tert-butoxycarbonyl)-L-valinate

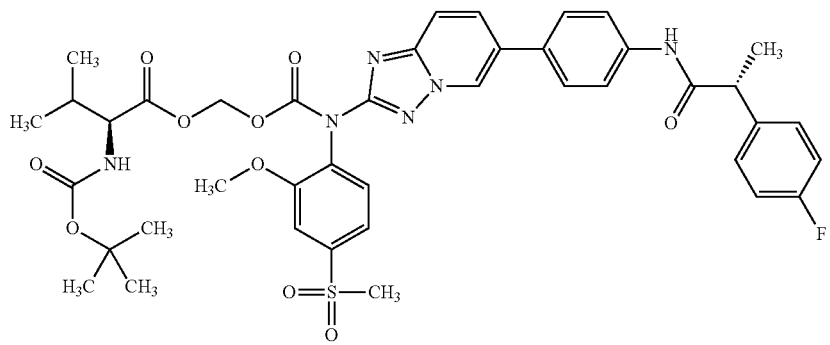 [SMILES: COc1cc(S(C)(=O)=O)ccc1N(C(=O)OCOC(=O)[C@@H](NC(=O)OC(C)(C)C)C(C)C)c1nc2ccc(-c3ccc(NC(=O)[C@H](C)c4ccc(F)cc4)cc3)cn2n1]

To a stirred suspension of ({(6-chloro[1,2,4]triazolo[1,5-α]pyridin-2-yl)[2-methoxy-4-(methylsulfonyl)phenyl]carbamoyl}oxy)methyl N-(tert-butoxycarbonyl)-L-valinate (580 mg) in toluene (20.5 mL) and NMP (2.0 mL) was added (4-{[(2R)-2-(4-fluorophenyl)propanoyl]amino}phenyl)boronic acid (399 mg), powdered potassium phosphate monohydrate (787 mg), dicyclohexyl(2',6'-dimethoxybiphenyl-2-yl)phosphine (76 mg) and palladium acetate (20.8 mg) and the flask was degassed twice and backfilled with argon. The mixture was heated to reflux for 20 minutes. The reaction mixture was filtered through a silica-gel column and the solvent was removed in vacuum. Silicagel chromatography gave 284 mg of the title compound.

Intermediate Example IntP03.01 caesium (2S)-2-[(tert-butoxycarbonyl)amino]-4-methylpentanoate

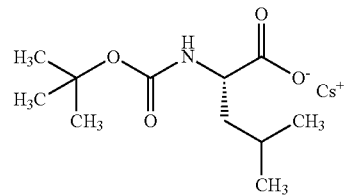

To a stirred solution of N-(tert-butoxycarbonyl)-L-leucine (1.0 g) in methanol (18.0 mL) was added a solution of caesium carbonate in water until pH 7 was reached (approx. 704 mg caesium carbonate in 3.6 mL water) and the solution was stirred for 30 minutes. The solvent was removed in vacuum, toluene was added and the solvent was again removed in vacuum to give 1.59 g of the title compound.

Intermediate Example IntP03.02

({(6-chloro[1,2,4]triazolo[1,5-α]pyridin-2-yl)[2-methoxy-4-(methylsulfonyl)phenyl]carbamoyl}oxy)methyl N-(tert-butoxycarbonyl)-L-leucinate

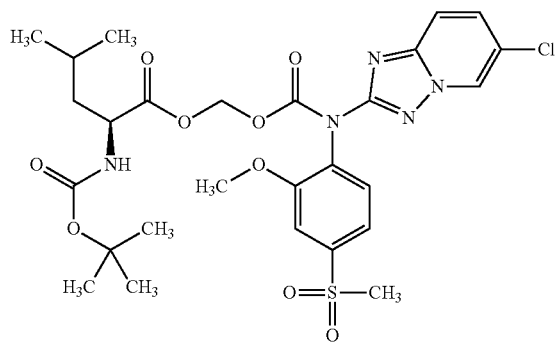 [SMILES: COc1cc(S(C)(=O)=O)ccc1N(C(=O)OCOC(=O)[C@H](CC(C)C)NC(=O)OC(C)(C)C)c1nc2ccc(Cl)cn2n1]

To a stirred solution of chloromethyl (6-chloro[1,2,4]triazolo[1,5-α]pyridin-2-yl)[2-methoxy-4-(methylsulfonyl)phenyl]carbamate (150 mg) in DMF (7.5 mL) was added caesium (2S)-2-[(tert-butoxycarbonyl)amino]-4-methylpentanoate (196 mg) and the mixture was stirred at room temperature for 16 h. Water was added, the mixture was extracted with ethyl acetate. The organic phase was washed with saturated sodium chloride solution, dried (sodium sulfate) and the solvent was removed in vacuum. Silicagel chromatography gave 179 mg of the title compound.

Intermediate Example IntP03.03

({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)methyl N-(tert-butoxycarbonyl)-L-leucinate

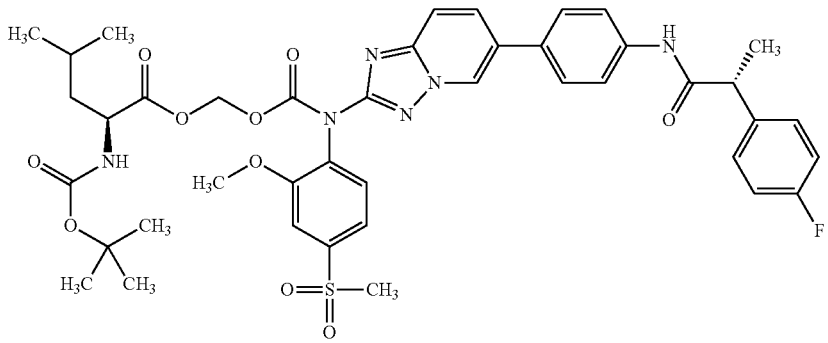 [SMILES: COc1cc(S(C)(=O)=O)ccc1N(C(=O)OCOC(=O)[C@H](CC(C)C)NC(=O)OC(C)(C)C)c1nc2ccc(-c3ccc(NC(=O)[C@H](C)c4ccc(F)cc4)cc3)cn2n1]

To a stirred suspension of ({(6-chloro[1,2,4]triazolo[1,5-α]pyridin-2-yl)[2-methoxy-4-(methylsulfonyl)phenyl]carbamoyl}oxy)methyl N-(tert-butoxycarbonyl)-L-leucinate (170 mg) in toluene (6.0 mL) and NMP (0.6 mL) was added (4-{[(2R)-2-(4-fluorophenyl)propanoyl]amino}phenyl)boronic acid (114 mg), powdered potassium phosphate monohydrate (225 mg), dicyclohexyl(2',6'-dimethoxybiphenyl-2-yl)phosphine (21.8 mg) and palladium acetate (6.0 mg) and the flask was degassed twice and backfilled with argon. The mixture was heated to reflux for 20 minutes. The reaction mixture was filtered through a silica-gel column and the solvent was removed in vacuum. Silicagel chromatography gave 76 mg of the title compound.

Intermediate Example IntP04.01 caesium (2S)-2-[(tert-butoxycarbonyl)(methyl)amino]-3-methylbutanoate

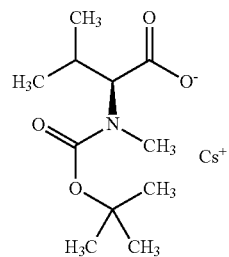

To a stirred solution of N-(tert-butoxycarbonyl)-N-methyl-L-valine (1.0 g) in methanol (18.0 mL) was added a solution of caesium carbonate in water until pH 7 was reached (approx. 704 mg caesium carbonate in 3.5 mL water) and the solution was stirred for 30 minutes. The solvent was removed in vacuum, toluene was added and the solvent was again removed in vacuum to give 1.55 g of the title compound.

Intermediate Example IntP04.02

({(6-chloro[1,2,4]triazolo[1,5-α]pyridin-2-yl)[2-methoxy-4-(methylsulfonyl)phenyl]carbamoyl}oxy)methyl N-(tert-butoxycarbonyl)-N-methyl-L-valinate To a stirred solution of chloromethyl (6-chloro[1,2,4]triazolo[1,5-α]pyridin-2-yl)[2-methoxy-4-(methylsulfonyl)phenyl]carbamate (220 mg) in DMF (11 mL) was added caesium (2S)-2-[(tert-butoxycarbonyl)(methyl)amino]-3-methylbutanoate (278 mg) and the mixture was stirred at room temperature for 16 h. Water was added, the mixture was extracted with ethyl acetate. The organic phase was washed with saturated sodium chloride solution, dried (sodium sulfate) and the solvent was removed in vacuum. Silicagel chromatography gave 298 mg of the title compound.

Intermediate Example IntP04.03

({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)methyl N-(tert-butoxycarbonyl)-N-methyl-L-valinate

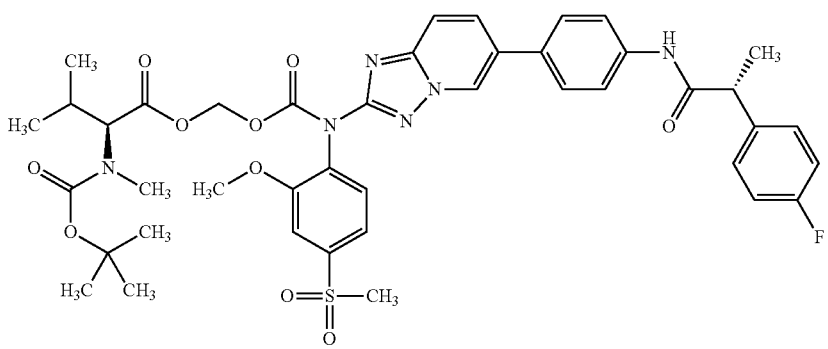 [SMILES: COc1cc(S(C)(=O)=O)ccc1N(C(=O)OCOC(=O)[C@H](C(C)C)N(C)C(=O)OC(C)(C)C)c1nc2ccc(-c3ccc(NC(=O)[C@H](C)c4ccc(F)cc4)cc3)cn2n1]

To a stirred suspension of ({(6-chloro[1,2,4]triazolo[1,5-α]pyridin-2-yl)[2-methoxy-4-(methylsulfonyl)phenyl]carbamoyl}oxy)methyl N-(tert-butoxycarbonyl)-N-methyl-L-valinate (292 mg) in toluene (10 mL) and NMP (1.0 mL) was added (4-{[(2R)-2-(4-fluorophenyl)propanoyl]amino}phenyl) boronic acid (196 mg), powdered potassium phosphate monohydrate (387 mg), dicyclohexyl(2',6'-dimethoxybiphenyl-2-yl)phosphine (37.5 mg) and palladium acetate (10.2 mg) and the flask was degassed twice and backfilled with argon. The mixture was heated to reflux for 20 minutes. The reaction mixture was filtered through a silica-gel column and the solvent was removed in vacuum. Silicagel chromatography gave 110 mg of the title compound.

Intermediate Example IntP05.01 caesium (2S)-2-[(tert-butoxycarbonyl)amino]-3,3-dimethylbutanoate

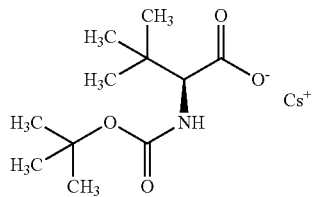

To a stirred solution of N-(tert-butoxycarbonyl)-N-methyl-L-valine (4.08 g) in methanol (36 mL) was added a solution of caesium carbonate in water until pH 7 was reached (approx. 2.85 g caesium carbonate in 36 mL water) and the solution was stirred for 30 minutes. The solvent was removed in vacuum, toluene was added and the solvent was again removed in vacuum to give 6.34 g of the title compound.

Intermediate Example IntP05.02

({(6-chloro[1,2,4]triazolo[1,5-α]pyridin-2-yl)[2-methoxy-4-(methylsulfonyl)phenyl]carbamoyl}oxy)methyl N-(tert-butoxycarbonyl)-3-methyl-L-valinate

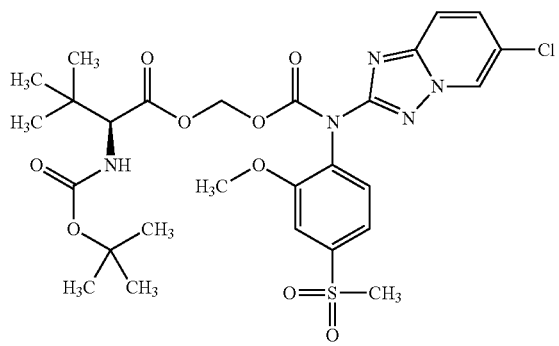 [SMILES: COc1cc(S(C)(=O)=O)ccc1N(C(=O)OCOC(=O)[C@@H](NC(=O)OC(C)(C)C)C(C)(C)C)c1nc2ccc(Cl)cn2n1]

To a stirred solution of chloromethyl (6-chloro[1,2,4]triazolo[1,5-α]pyridin-2-yl)[2-methoxy-4-(methylsulfonyl)phenyl]carbamate (1.66 g) in DMF (83 mL) was added caesium (2S)-2-[(tert-butoxycarbonyl)amino]-3,3-dimethylbutanoate (2.17 g) and the mixture was stirred at room temperature for 16 h. Water was added, the mixture was extracted with ethyl acetate. The organic phase was washed with saturated sodium chloride solution, dried (sodium sulfate) and the solvent was removed in vacuum. Silicagel chromatography gave 2.30 g of the title compound.

Intermediate Example IntP05.03

({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)methyl N-(tert-butoxycarbonyl)-3-methyl-L-valinate

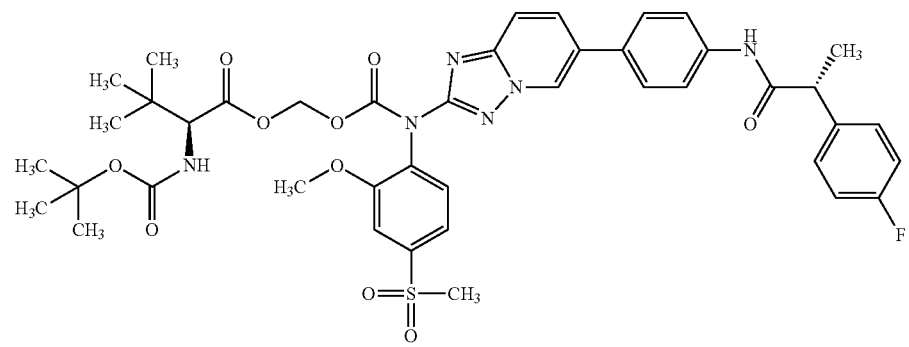 [SMILES: COc1cc(S(C)(=O)=O)ccc1N(C(=O)OCOC(=O)[C@@H](NC(=O)OC(C)(C)C)C(C)(C)C)c1nc2ccc(-c3ccc(NC(=O)[C@H](C)c4ccc(F)cc4)cc3)cn2n1]

To a stirred suspension of ({(6-chloro[1,2,4]triazolo[1,5-α]pyridin-2-yl)[2-methoxy-4-(methylsulfonyl)phenyl]carbamoyl}oxy)methyl N-(tert-butoxycarbonyl)-3-methyl-L-valinate (404 mg) in toluene (11.5 mL) was added (4-{[(2R)-2-(4-fluorophenyl)propanoyl]amino}phenyl) boronic acid (245 mg), powdered potassium phosphate monohydrate (482 mg), dicyclohexyl(2',6'-dimethoxybiphenyl-2-yl)phosphine (46.6 mg) and palladium acetate (12.8 mg) and the flask was degassed twice and backfilled with argon. The mixture was heated to 100° C. for 20 minutes. The reaction mixture was filtered through a silica-gel column and the solvent was removed in vacuum. Silicagel chromatography gave a solid that was triturated with a mixture of hexane and dichloromethane to give 223 mg of the title compound.

Intermediate Example IntP06.01

[(di-tert-butoxyphosphoryl)oxy]methyl (6-chloro[1,2,4]triazolo[1,5-α]pyridin-2-yl)[2-methoxy-4-(methylsulfonyl)phenyl]carbamate

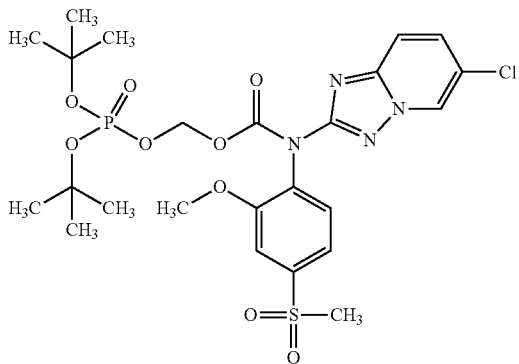 [SMILES: COc1cc(S(C)(=O)=O)ccc1N(C(=O)OCOP(=O)(OC(C)(C)C)OC(C)(C)C)c1nc2ccc(Cl)cn2n1]

To a stirred solution of chloromethyl (6-chloro[1,2,4]triazolo[1,5-α]pyridin-2-yl)[2-methoxy-4-(methylsulfonyl)phenyl]carbamate (200 mg) in DMF (6.0 mL) was added potassium di-tert-butyl phosphate (278 mg) and the mixture was heated to 75° C. for 75 minutes in a microwave oven. Water was added, the mixture was extracted with ethyl acetate. The organic phase was washed with saturated sodium chloride solution, dried (sodium sulfate) and the solvent was removed in vacuum. Silicagel chromatography gave 80 mg of the title compound.

Intermediate Example IntP06.02

[(di-tert-butoxyphosphoryl)oxy]methyl [6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamate

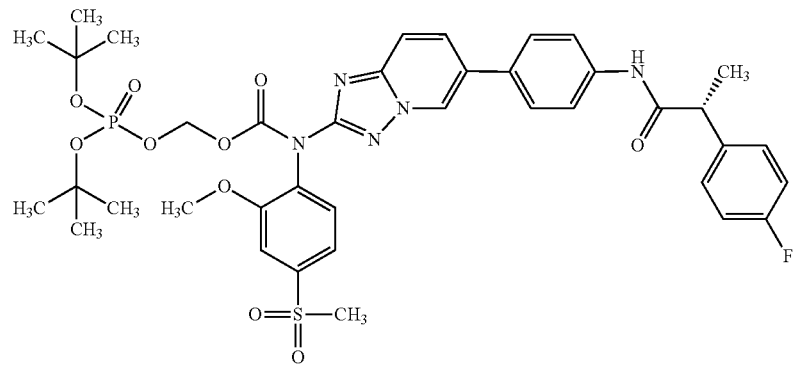 [SMILES: COc1cc(S(C)(=O)=O)ccc1N(C(=O)OCOP(=O)(OC(C)(C)C)OC(C)(C)C)c1nc2ccc(-c3ccc(NC(=O)[C@H](C)c4ccc(F)cc4)cc3)cn2n1]

To a stirred suspension of [(di-tert-butoxyphosphoryl)oxy]methyl (6-chloro[1,2,4]triazolo[1,5-α]pyridin-2-yl)[2-methoxy-4-(methylsulfonyl)phenyl]carbamate (77 mg) in toluene (3.0 mL) and NMP (0.3 mL) was added (4-{[(2R)-2-(4-fluorophenyl)propanoyl]amino}phenyl) boronic acid (53.6 mg), powdered potassium phosphate monohydrate (106 mg), dicyclohexyl(2',6'-dimethoxybiphenyl-2-yl)phosphine (10.2 mg) and palladium acetate (2.8 mg) and the flask was degassed twice and backfilled with argon. The mixture was heated to 100° C. for 20 minutes. The reaction mixture was filtered through a silica-gel column and the solvent was removed in vacuum. Silicagel chromatography gave a solid that was triturated with a mixture of hexane and dichloromethane to give 35 mg of the title compound.

Intermediate Example IntP07.01

({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)methyl $N^2,N^6$-bis(tert-butoxycarbonyl)-L-lysyl-L-valinate Intermediate Example IntP08.01

1-chloroethyl (6-chloro[1,2,4]triazolo[1,5-α]pyridin-2-yl)[2-methoxy-4-(methylsulfonyl)phenyl]carbamate

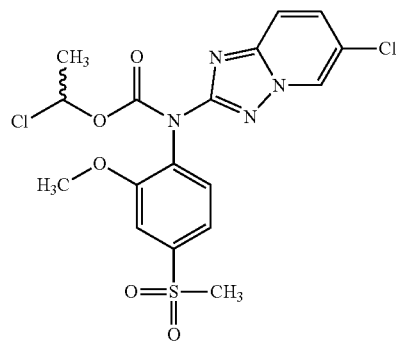

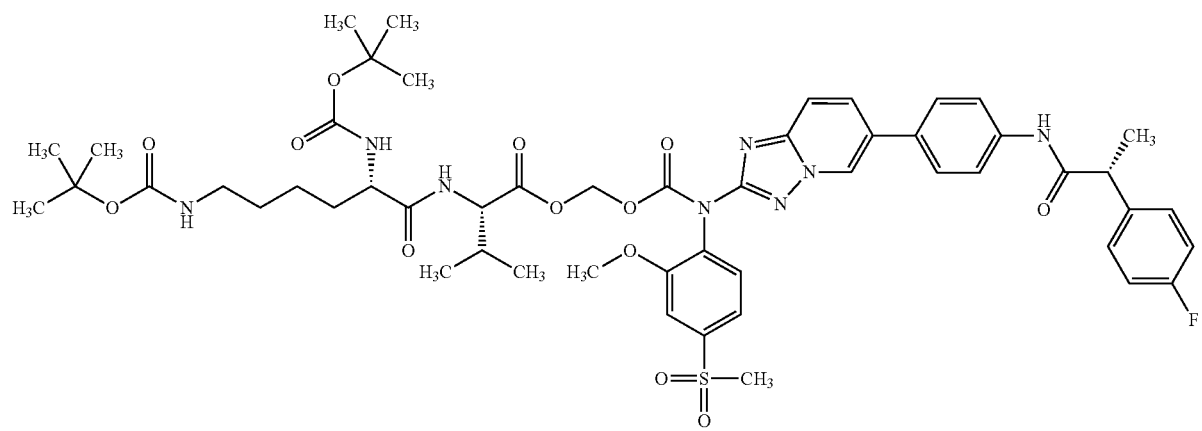 [SMILES: COc1cc(S(C)(=O)=O)ccc1N(C(=O)OCOC(=O)[C@@H](NC(=O)[C@H](CCCCNC(=O)OC(C)(C)C)NC(=O)OC(C)(C)C)C(C)C)c1nc2ccc(-c3ccc(NC(=O)[C@H](C)c4ccc(F)cc4)cc3)cn2n1]

To a stirred suspension of ({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)methyl L-valinate hydrochloride (122 mg) in DMF (2.6 mL) and dichloromethane (1.3 mL) was added sodium bicarbonate (37 mg), $N^2,N^6$-bis(tert-butoxycarbonyl)-L-lysine (56 mg) and HATU (84 mg). The mixture was stirred at room temperature for 3 h. Water was added, and the mixture was stirred for 2 h. Water was added and the mixture was extracted with ethyl acetate. The organic phase was washed with saturated sodium chloride solution, dried (sodium sulfate) and the solvent was removed in vacuum to give 61 mg of the title product as a crude product that was used for the next step without purification.

To a stirred solution of 6-chloro-N-[2-methoxy-4-(methylsulfonyl)phenyl][1,2,4]triazolo[1,5-α]pyridin-2-amine (Int21.03) (1.00 g) in THF (100 mL) was added sodium hydride (55% w/w in oil; 618 mg) at room temperature and the mixture was stirred at 0° C. for 15 minutes. 1-Chloroethyl chloroformate (0.78 mL) was added and the mixture was stirred at room temperature for 1 h. A half-saturated solution of sodium chloride was added and the mixture was extracted with ethyl acetate. The organic phase was dried (sodium sulfate) and the solvent was removed in vacuum. Silicagel chromatography gave 1.03 g of the title compound.

Intermediate Example IntP08.02

(1RS)-1-({(6-chloro[1,2,4]triazolo[1,5-α]pyridin-2-yl)[2-methoxy-4-(methylsulfonyl)phenyl]carbamoyl}oxy)ethyl N-(tert-butoxycarbonyl)-L-valinate (Mixture of 2 Epimers)

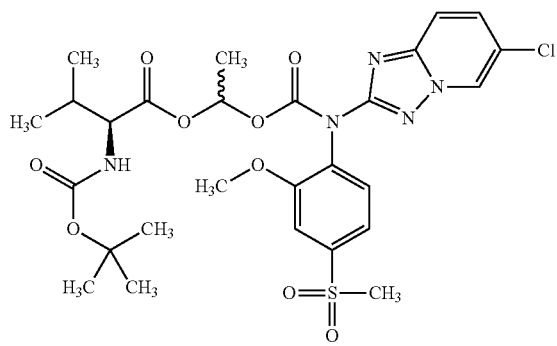 [SMILES: COc1cc(S(C)(=O)=O)ccc1N(C(=O)OC(C)OC(=O)[C@@H](NC(=O)OC(C)(C)C)C(C)C)c1nc2ccc(Cl)cn2n1]

To a stirred solution of 1-chloroethyl (6-chloro[1,2,4]triazolo[1,5-α]pyridin-2-yl)[2-methoxy-4-(methylsulfonyl)phenyl]carbamate (500 mg) in DMF (24 mL) was added caesium (2S)-2-[(tert-butoxycarbonyl)amino]-3-methylbutanoate (608 mg) and the mixture was heated to 50° C. for 16 h.

Water was added, the mixture was extracted with ethyl acetate. The organic phase was washed with saturated sodium chloride solution, dried (sodium sulfate) and the solvent was removed in vacuum. Silicagel chromatography gave 626 mg of the title compound.

Intermediate Example IntP08.03

(1RS)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)ethyl N-(tert-butoxycarbonyl)-L-valinate (Mixture of 2 Epimers)

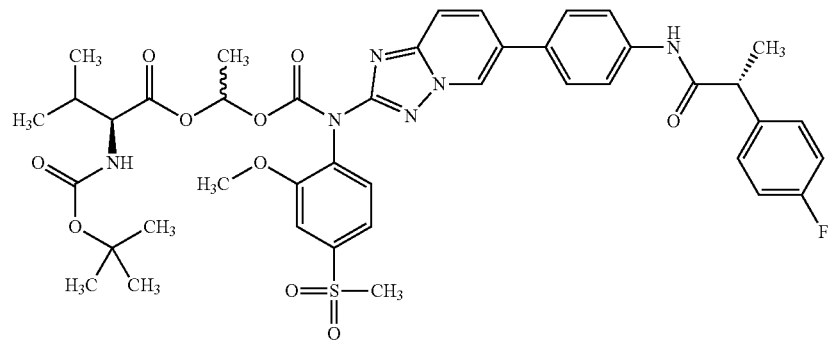 [SMILES: COc1cc(S(C)(=O)=O)ccc1N(C(=O)OC(C)OC(=O)[C@@H](NC(=O)OC(C)(C)C)C(C)C)c1nc2ccc(-c3ccc(NC(=O)[C@H](C)c4ccc(F)cc4)cc3)cn2n1]

To a stirred suspension of 1-({(6-chloro[1,2,4]triazolo[1,5-α]pyridin-2-yl)[2-methoxy-4-(methylsulfonyl)phenyl]carbamoyl}oxy)ethyl N-(tert-butoxycarbonyl)-L-valinate (595 mg) in toluene (20 mL) and NMP (2.0 mL) was added (4-{[(2R)-2-(4-fluorophenyl)propanoyl]amino}phenyl)boronic acid (400 mg), powdered potassium phosphate monohydrate (789 mg), dicyclohexyl(2',6'-dimethoxybiphenyl-2-yl)phosphine (76.3 mg) and palladium acetate (20.9 mg) and the flask was degassed twice and backfilled with argon. The mixture was heated to 100° C. for 20 minutes. The reaction mixture was filtered through a silica-gel column and the solvent was removed in vacuum. Silicagel chromatography gave 341 mg of the title compound.

Intermediate Example IntP09.01

(1RS)-1-({(6-chloro[1,2,4]triazolo[1,5-α]pyridin-2-yl)[2-methoxy-4-(methylsulfonyl)phenyl]carbamoyl}oxy)ethyl N-(tert-butoxycarbonyl)-3-methyl-L-valinate (Mixture of 2 Epimers)

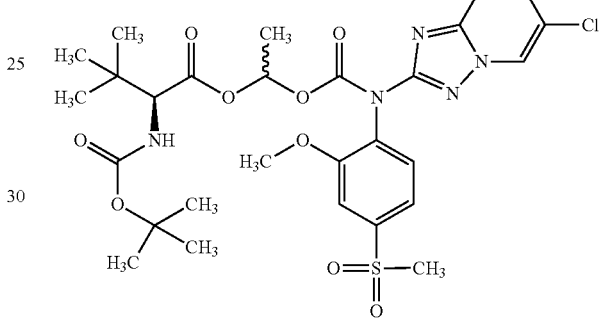

To a stirred solution of 1-chloroethyl (6-chloro[1,2,4]triazolo[1,5-α]pyridin-2-yl)[2-methoxy-4-(methylsulfonyl)phenyl]carbamate (500 mg) in DMF (24 mL) was added caesium (2S)-2-[(tert-butoxycarbonyl)amino]-3,3-dimethylbutanoate (633 mg) and the mixture was heated to 50° C. for 16 h. Water was added, the mixture was extracted with ethyl acetate. The organic phase was washed with saturated sodium chloride solution, dried (sodium sulfate) and the solvent was removed in vacuum. Silicagel chromatography gave 548 mg of the title compound.

Intermediate Example IntP09.02

(1RS)-1-({[6-(4-{[(2R)-2-(4-fluorophenyl)pro-panoyl]amino}phenyl)[1,2,4]triazolo[1,5-α]pyridin-2-yl][2-methoxy-4-(methylsulfonyl)phenyl]carbamoyl}oxy)ethyl N-(tert-butoxycarbonyl)-3-methyl-L-valinate (Mixture of 2 Epimers)

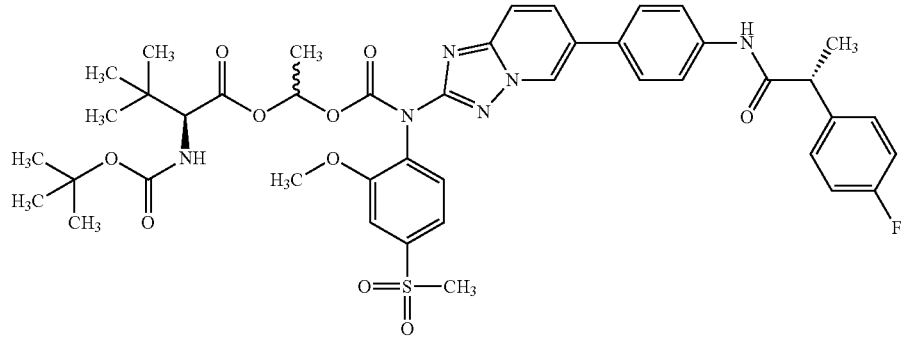 [SMILES: COc1cc(S(C)(=O)=O)ccc1N(C(=O)OC(C)OC(=O)[C@@H](NC(=O)OC(C)(C)C)C(C)(C)C)c1nc2ccc(-c3ccc(NC(=O)[C@H](C)c4ccc(F)cc4)cc3)cn2n1]

To a stirred suspension of (1RS)-1-({(6-chloro[1,2,4]triazolo[1,5-α]pyridin-2-yl)[2-methoxy-4-(methylsulfonyl)phenyl]carbamoyl}oxy)ethyl N-(tert-butoxycarbonyl)-3-methyl-L-valinate (mixture of 2 epimers) (100 mg) in toluene (3.4 mL) and NMP (0.34 mL) was added (4-{[(2R)-2-(4-fluorophenyl)propanoyl]amino}phenyl) boronic acid (65.8 mg), powdered potassium phosphate monohydrate (130 mg), dicyclohexyl(2',6'-dimethoxybiphenyl-2-yl)phosphine (12.6 mg) and palladium acetate (3.4 mg) and the flask was degassed twice and backfilled with argon. The mixture was heated to reflux for 20 minutes. The reaction mixture was filtered through a silica-gel column and the solvent was removed in vacuum. Silicagel chromatography gave 42 mg of the title compound as a mixture of 2 epimers.

Large Scale Procedure:

To a stirred suspension of 1-({(6-chloro[1,2,4]triazolo[1,5-α]pyridin-2-yl)[2-methoxy-4-(methylsulfonyl)phenyl]carbamoyl}oxy)ethyl N-(tert-butoxycarbonyl)-3-methyl-L-valinate (8830 mg) in toluene (250 mL) and NMP (12 mL) was added (4-{[(2R)-2-(4-fluorophenyl)propanoyl]amino}phenyl) boronic acid (4558 mg), powdered potassium phosphate monohydrate (9627 mg), dicyclohexyl(2',6'-dimethoxybiphenyl-2-yl)phosphine (931 mg) and palladium acetate (255 mg) and the flask was degassed twice and backfilled with argon. The mixture was heated to reflux for 20 minutes. The reaction mixture was twice filtered through a silica-gel column and the solvent was removed in vacuum. Silicagel chromatography gave 5035 mg of the title compound as a mixture of 2 epimers.

Intermediate Example IntP09.03

(1R or 1S)-1-({[6-(4-{[(2R)-2-(4-fluorophenyl)pro-panoyl]amino}phenyl)[1,2,4]triazolo[1,5-α]pyridin-2-yl][2-methoxy-4-(methylsulfonyl)phenyl]carbamoyl}oxy)ethyl-N-(tert-butoxycarbonyl)-3-methyl-L-valinate (Single Stereoisomer A)

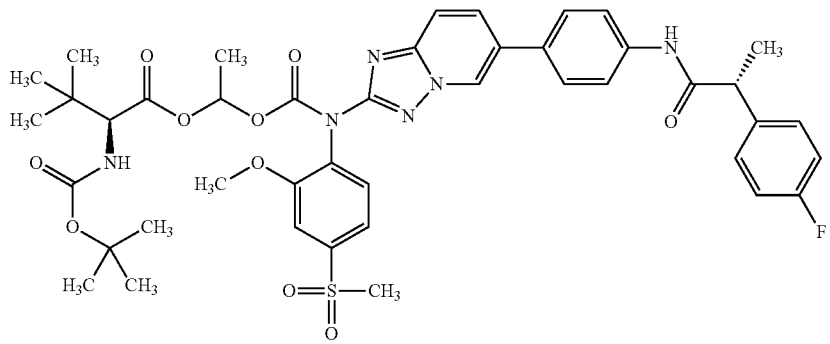 [SMILES: COc1cc(S(C)(=O)=O)ccc1N(C(=O)OC(C)OC(=O)[C@@H](NC(=O)OC(C)(C)C)C(C)(C)C)c1nc2ccc(-c3ccc(NC(=O)[C@H](C)c4ccc(F)cc4)cc3)cn2n1]

Intermediate Example IntP09.04

(1S or 1R)-1-({[6-(4-{[(2R)-2-(4-fluorophenyl)pro-
panoyl]amino}phenyl)[1,2,4]triazolo[1,5-α]pyridin-
2-yl][2-methoxy-4-(methylsulfonyl)phenyl]
carbamoyl}oxy)ethyl-N-(tert-butoxycarbonyl)-3-
methyl-L-valinate (Single Stereoisomer B)

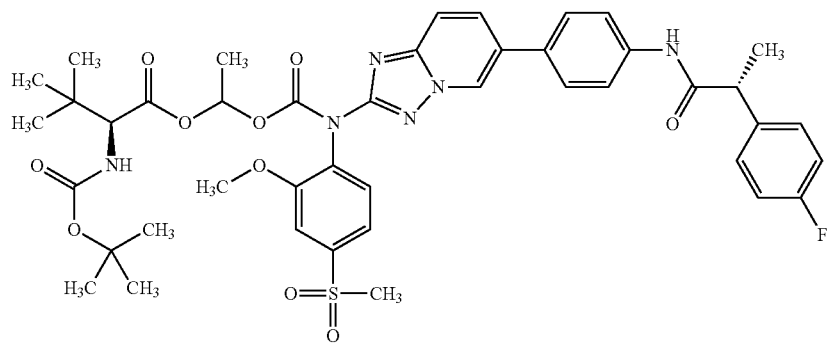 [SMILES: COc1cc(S(C)(=O)=O)ccc1N(C(=O)OC(C)OC(=O)[C@@H](NC(=O)OC(C)(C)C)C(C)(C)C)c1nc2ccc(-c3ccc(NC(=O)[C@H](C)c4ccc(F)cc4)cc3)cn2n1]

7.96 g of (1RS)-1-({[6-(4-{[(2R)-2-(4-fluorophenyl)pro-
panoyl]amino}phenyl) [1,2,4]triazolo[1,5-α]pyridin-2-yl]
[2-methoxy-4-(methylsulfonyl)phenyl]carbamoyl}oxy)
ethyl N-(tert-butoxycarbonyl)-3-methyl-L-valinate (mixture
of 2 epimers) was separated into the single stereoisomers
(Intermediate Example IntP09.03 and Intermediate Example
IntP09.04) via preparative, chiral HPLC.

| System: | Agilent: Prep 1200, 2 × Prep Pump, DLA, MWD, Gilson: Liquid Handler 215 |
|---|---|
| Column: | Chiralpak IB 5 μm 250 × 30 mm |
| Solvent: | Hexane/ethanol 70:30 (v/v) |
| Flow: | 50 mL/min |
| Temperature: | RT |
| Solution: | 7960 mg/29.6 mL DCM/MeOH |
| Injection: | 47 × 0.63 mL |
| Detection: | UV 280 nm |

| | Retention time in min | purity in % | yield |
|---|---|---|---|
| Intermediate Example IntP09.03 Stereoisomer A | 10.2-13.2 | >99.9% | 2997 mg |
| Intermediate Example IntP09.04 Stereoisomer B | 13.7-20.6 | 99.1% | 3386 mg |

Intermediate Example IntP10.01

Caesium (2S)-2-[(tert-butoxycarbonyl)amino]-2,3-
dimethylbutanoate

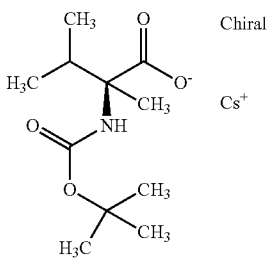

Intermediate Example IntP10.01. was prepared analogously to the procedure for the preparation of Intermediate Example IntP02.01.

Intermediate Example IntP10.02

({(6-chloro[1,2,4]triazolo[1,5-α]pyridin-2-yl)[2-methoxy-4-(methylsulfonyl)phenyl]carbamoyl}oxy)methyl N-(tert-butoxycarbonyl)-3-methyl-L-isovalinate

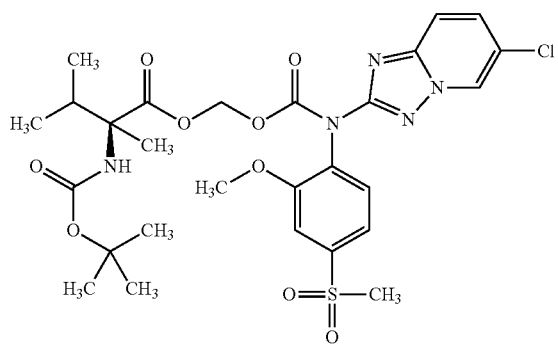 [SMILES: COc1cc(S(C)(=O)=O)ccc1N(C(=O)OCOC(=O)[C@@](C)(NC(=O)OC(C)(C)C)C(C)C)c1nc2ccc(Cl)cn2n1]

Starting with chloromethyl (6-chloro[1,2,4]triazolo[1,5-α]pyridin-2-yl)[2-methoxy-4-(methylsulfonyl)phenyl]carbamate and caesium (2S)-2-[(tert-butoxycarbonyl)amino]-2,3-dimethylbutanoate, Intermediate Example IntP10.02. was prepared analogously to the procedure for the preparation of Intermediate Example IntP02.02.

Intermediate Example IntP10.03

({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)methyl N-(tert-butoxycarbonyl)-3-methyl-L-isovalinate Starting with Intermediate Example IntP10.02 and (4-{[(2R)-2-(4-fluorophenyl)propanoyl]amino}phenyl)boronic acid, Intermediate Example IntP10.03. was prepared analogously to the procedure for the preparation of Intermediate Example IntP02.03.

Intermediate Example IntP11.01

Caesium 3-[(tert-butoxycarbonyl)amino]-2,2-dimethylpropanoate

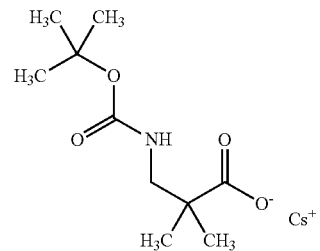

Intermediate Example IntP11.01. was prepared analogously to the procedure for the preparation of Intermediate Example IntP02.01.

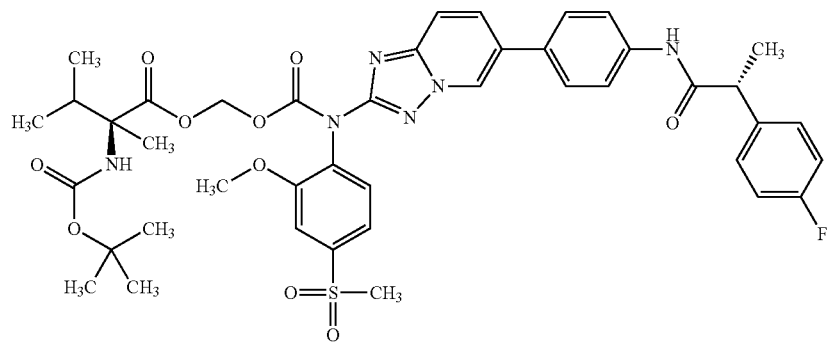 [SMILES: COc1cc(S(C)(=O)=O)ccc1N(C(=O)OCOC(=O)[C@@](C)(NC(=O)OC(C)(C)C)C(C)C)c1nc2ccc(-c3ccc(NC(=O)[C@H](C)c4ccc(F)cc4)cc3)cn2n1]

Intermediate Example IntP11.02

({(6-chloro[1,2,4]triazolo[1,5-α]pyridin-2-yl)[2-methoxy-4-(methylsulfonyl)phenyl]carbamoyl}oxy) methyl 3-[(tert-butoxycarbonyl)amino]-2,2-dimethylpropanoate

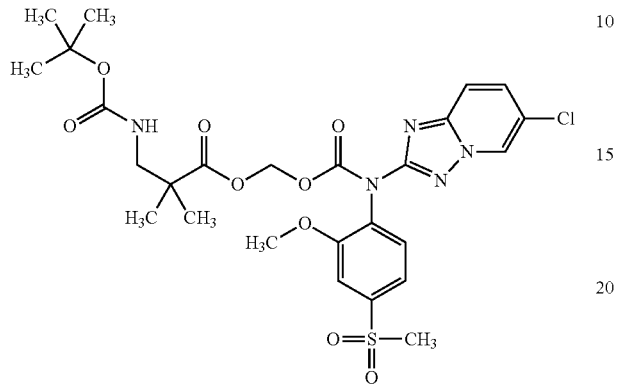

Intermediate Example IntP11.02. was prepared analogously to the procedure for the preparation of Intermediate Example IntP02.02.

Intermediate Example IntP11.03

({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy) methyl 3-[(tert-butoxycarbonyl)amino]-2,2-dimethylpropanoate

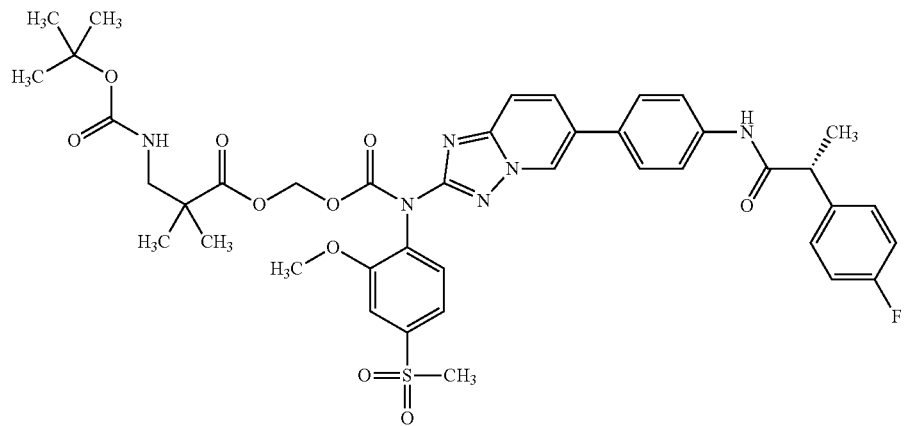 [SMILES: COc1cc(S(C)(=O)=O)ccc1N(C(=O)OCOC(=O)C(C)(C)CNC(=O)OC(C)(C)C)c1nc2ccc(-c3ccc(NC(=O)[C@H](C)c4ccc(F)cc4)cc3)cn2n1]

Starting with Intermediate Example IntP11.02 and (4-{[(2R)-2-(4-fluorophenyl)propanoyl]amino}phenyl)boronic acid, Intermediate Example IntP11.03. was prepared analogously to the procedure for the preparation of Intermediate Example IntP02.03.

Intermediate Example IntP12.01

(1RS)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)ethyl $N^2,N^6$-bis(tert-butoxycarbonyl)-L-lysyl-L-valinate (Mixture of 2 Epimers)

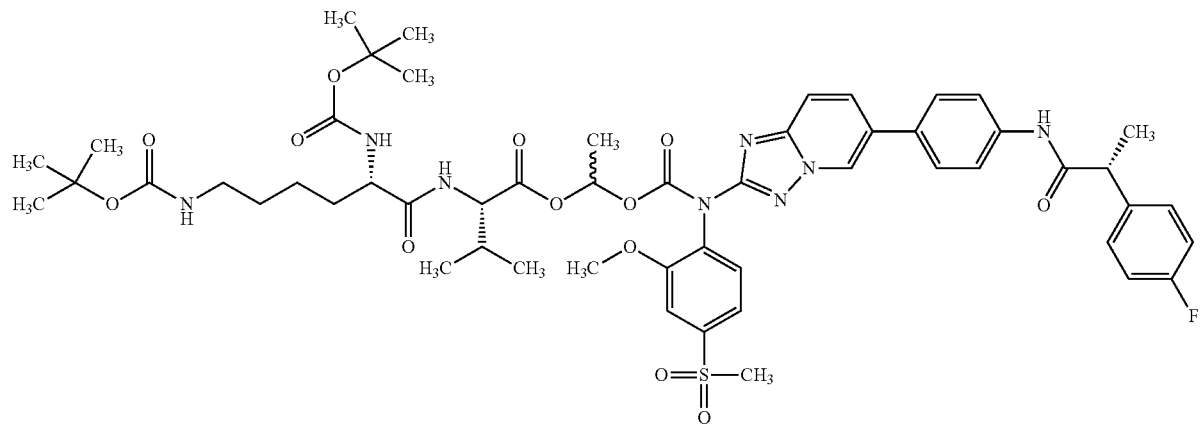 [SMILES: COc1cc(S(C)(=O)=O)ccc1N(C(=O)OC(C)OC(=O)[C@@H](NC(=O)[C@H](CCCCNC(=O)OC(C)(C)C)NC(=O)OC(C)(C)C)C(C)C)c1nc2ccc(-c3ccc(NC(=O)[C@H](C)c4ccc(F)cc4)cc3)cn2n1]

To a stirred suspension of (1RS)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)ethyl L-valinate hydrochloride (mixture of 2 epimers) (150 mg) in DMF (3.2 mL) and dichloromethane (3.2 mL) was added $N^2,N^6$-bis(tert-butoxycarbonyl)-L-lysine (93 mg) and HATU (115 mg). Then sodium bicarbonate (75 mg) was added in small portions and the mixture was stirred at room temperature for 4 h. Water was added, and the mixture was stirred for 2 h. Water was added and the mixture was extracted with ethyl acetate. The organic phase was washed with saturated sodium chloride solution, dried (sodium sulfate) and the solvent was removed in vacuum. Silicagel chromatography followed by preparative reverse phase HPLC gave 76 mg of the title compound.

Intermediate Example IntP13.01

({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)methyl N-(tert-butoxycarbonyl)-L-valyl-L-valinate

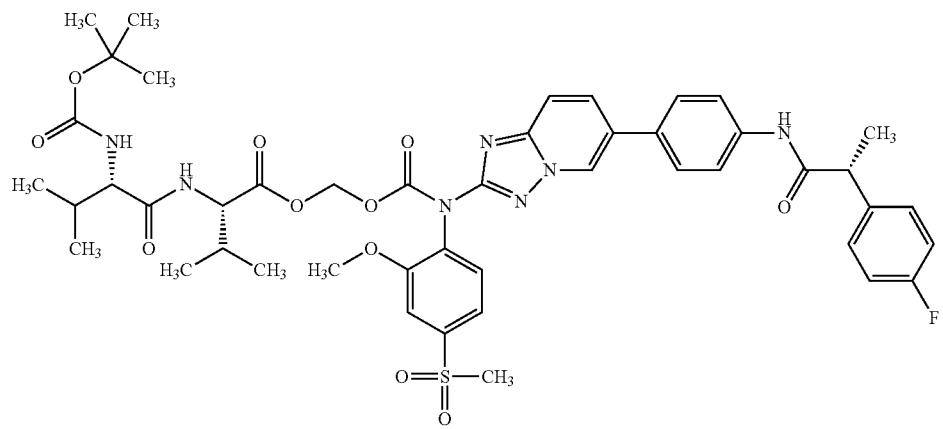 [SMILES: COc1cc(S(C)(=O)=O)ccc1N(C(=O)OCOC(=O)[C@@H](NC(=O)[C@@H](NC(=O)OC(C)(C)C)C(C)C)C(C)C)c1nc2ccc(-c3ccc(NC(=O)[C@H](C)c4ccc(F)cc4)cc3)cn2n1]

Intermediate Example IntP13.01. was prepared analogously to the procedure for the preparation of Intermediate Example IntP12.01.

Intermediate Example IntP14.01

(1RS)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)ethyl N-(tert-butoxycarbonyl)-L-valyl-L-valinate (Mixture of 2 Epimers)

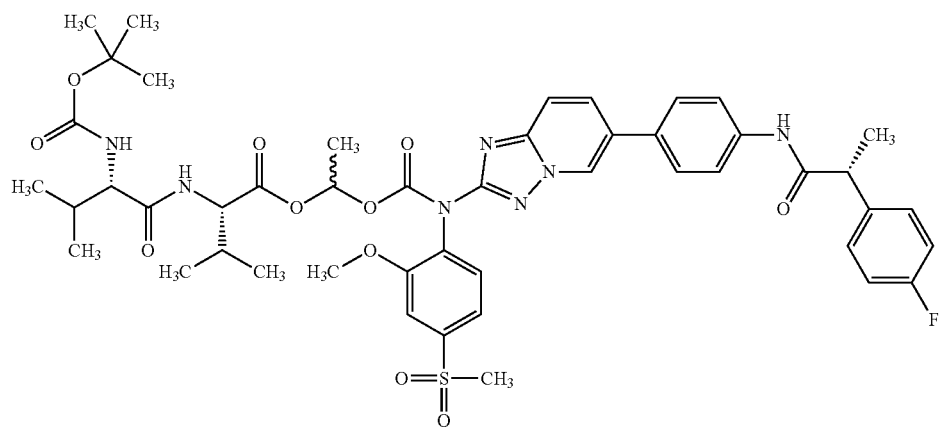 [SMILES: COc1cc(S(C)(=O)=O)ccc1N(C(=O)OC(C)OC(=O)[C@@H](NC(=O)[C@@H](NC(=O)OC(C)(C)C)C(C)C)C(C)C)c1nc2ccc(-c3ccc(NC(=O)[C@H](C)c4ccc(F)cc4)cc3)cn2n1]

Intermediate Example IntP14.01. was prepared analogously to the procedure for the preparation of Intermediate Example IntP12.01.

Intermediate Example IntP15.01

Caesium (2S,3S)-2-[(tert-butoxycarbonyl)amino]-3-methylpentanoate

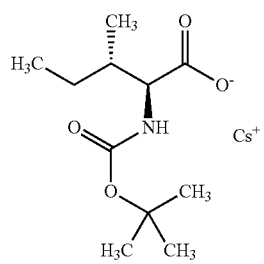

Intermediate Example IntP15.01. was prepared analogously to the procedure for the preparation of Intermediate Example IntP02.01.

Intermediate Example IntP15.02

(1RS)-1-({{(6-chloro[1,2,4]triazolo[1,5-α]pyridin-2-yl)[2-methoxy-4-(methylsulfonyl)phenyl]carbamoyl}oxy)ethyl N-(tert-butoxycarbonyl)-L-isoleucinate (Mixture of 2 Epimers)

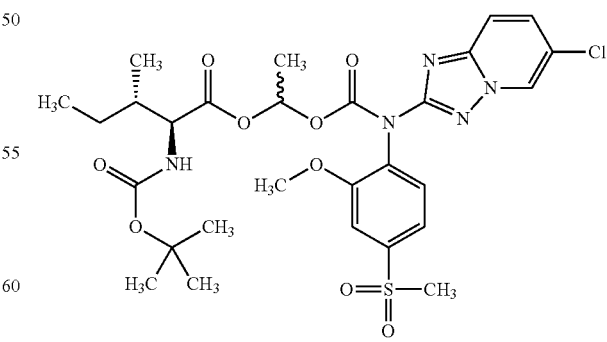

Intermediate Example IntP15.02. was prepared analogously to the procedure for the preparation of Intermediate Example IntP09.01.

Intermediate Example IntP15.03

(1RS)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)ethyl N-(tert-butoxycarbonyl)-L-isoleucinate (Mixture of 2 Epimers)

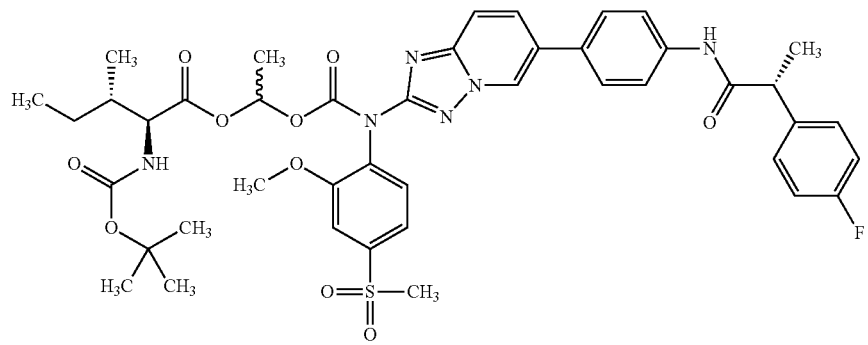 [SMILES: CC[C@H](C)[C@H](NC(=O)OC(C)(C)C)C(=O)OC(C)OC(=O)N(c1nc2ccc(-c3ccc(NC(=O)[C@H](C)c4ccc(F)cc4)cc3)cn2n1)c1ccc(S(C)(=O)=O)cc1OC]

Starting with Intermediate Example IntP15.02 (1.37 g) Intermediate Example IntP15.03. was prepared analogously to the procedure for the preparation of Intermediate Example IntP09.02. Yield: 623 mg of the title compound.

Intermediate Example IntP15.04

(1S or 1R)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)ethyl-N-(tert-butoxycarbonyl)-L-isoleucinate (Single Stereoisomer A)

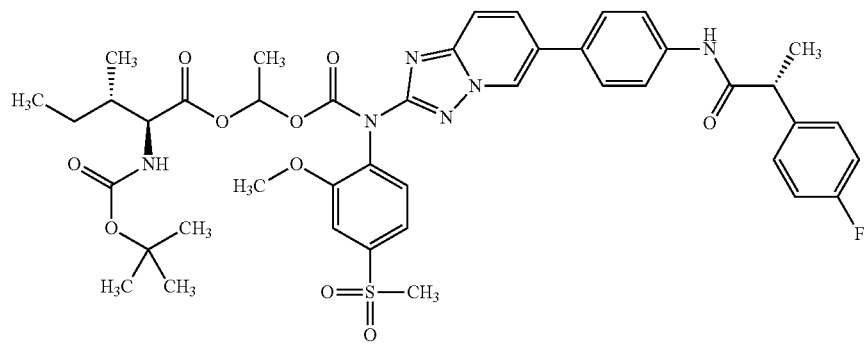 [SMILES: CC[C@H](C)[C@H](NC(=O)OC(C)(C)C)C(=O)OC(C)OC(=O)N(c1nc2ccc(-c3ccc(NC(=O)[C@H](C)c4ccc(F)cc4)cc3)cn2n1)c1ccc(S(C)(=O)=O)cc1OC]

Intermediate Example IntP15.05

(1R or 1S)-1-({[6-(4-{[(2R)-2-(4-fluorophenyl)pro-
panoyl]amino}phenyl)[1,2,4]triazolo[1,5-α]pyridin-
2-yl][2-methoxy-4-(methylsulfonyl)phenyl]
carbamoyl}oxy)ethyl-N-(tert-butoxycarbonyl)-L-
isoleucinate (Single Stereoisomer B)

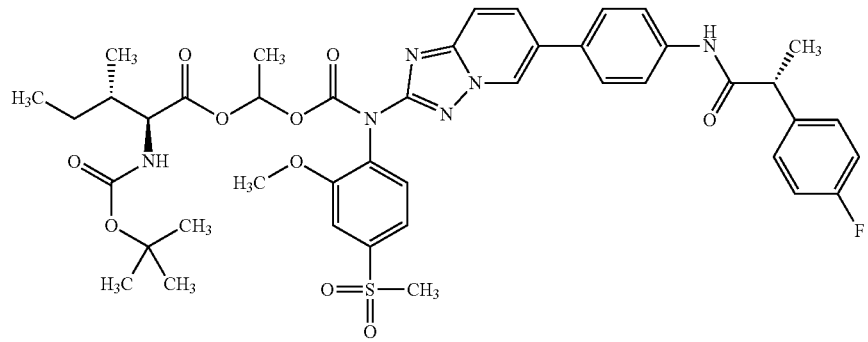 [SMILES: CC[C@H](C)[C@H](NC(=O)OC(C)(C)C)C(=O)OC(C)OC(=O)N(c1nc2ccc(-c3ccc(NC(=O)[C@H](C)c4ccc(F)cc4)cc3)cn2n1)c1ccc(S(C)(=O)=O)cc1OC]

(1RS)-1-({[6-(4-{[(2R)-2-(4-fluorophenyl)propanoyl]
amino}phenyl) [1, 2,4]triazolo[1,5-α]pyridin-2-yl][2-
methoxy-4-(methylsulfonyl)phenyl]carbamoyl}oxy)ethyl
N-(tert-butoxycarbonyl)-L-isoleucinate (mixture of 2
epimers) (523 mg) was separated into the single stereoiso-
mers (Intermediate Example IntP15.04 and Intermediate
Example IntP15.05) via preparative, chiral HPLC.

| System: | Agilent: Prep 1200, 2 × Prep Pump, DLA, MWD, Gilson: Liquid Handler 215 |
|---|---|
| Column: | Chiralpak IB 5 µm 250 × 30 mm |
| Solvent: | Hexane/ethanol 70:30 (v/v) |
| Flow: | 50 mL/min |
| Temperature: | RT |
| Solution: | 523 mg/4 mL DCM/MeOH |
| Injection: | 8 × 0.5 mL |
| Detection: | UV 254 nm |

| | Retention time in min | purity in % | yield |
|---|---|---|---|
| Intermediate Example IntP15.04 Stereoisomer A | 10-12.5 | >99.2% | 210 mg |
| Intermediate Example IntP15.05 Stereoisomer B | 15-20 | 98.45% | 235 mg |

Intermediate Example IntP16.01 chloromethyl (6-chloro[1,2,4]triazolo[1,5-α]pyridin-
2-yl)[4-(methylsulfonyl)-2-(2, 2, 2-trifluoroethoxy)
phenyl]carbamate

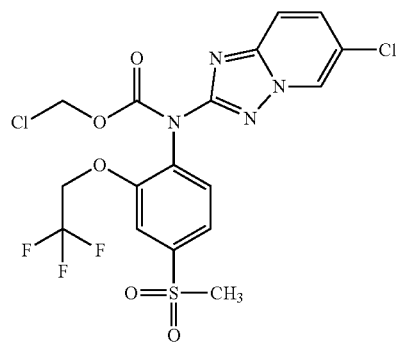 [SMILES: CS(=O)(=O)c1ccc(N(C(=O)OCCl)c2nc3ccc(Cl)cn3n2)c(OCC(F)(F)F)c1]

Starting with Intermediate Example Int05.04., IntP16.01.
was prepared analogously to the procedure for the prepara-
tion of Intermediate Example IntP01.01.

Intermediate Example IntP16.02

({(6-chloro[1,2,4]triazolo[1,5-α]pyridin-2-yl)[4-
(methylsulfonyl)-2-(2,2,2-trifluoroethoxy)phenyl]
carbamoyl}oxy)methyl N-(tert-butoxycarbonyl)-3-
methyl-L-valinate

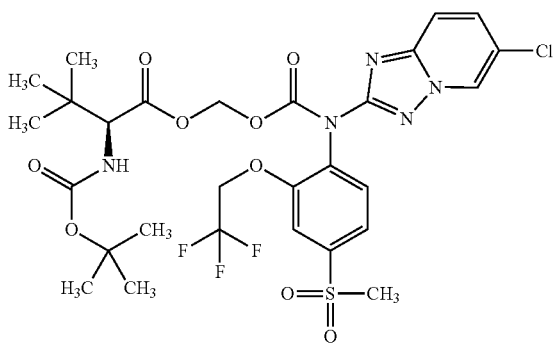 [SMILES: CC(C)(C)OC(=O)N[C@H](C(=O)OCOC(=O)N(c1nc2ccc(Cl)cn2n1)c1ccc(S(C)(=O)=O)cc1OCC(F)(F)F)C(C)(C)C]

To a stirred solution of chloromethyl (6-chloro[1,2,4]triazolo[1,5-α]pyridin-2-yl)[4-(methylsulfonyl)-2-(2,2,2-trifluoroethoxy)phenyl]carbamate (220 mg) in DMF (8.3 mL) was added caesium (2S)-2-[(tert-butoxycarbonyl)amino]-3,3-dimethylbutanoate (249 mg) and the mixture was stirred at room temperature for 16 h. Water was added, the mixture was extracted with ethyl acetate. The organic phase was washed with saturated sodium chloride solution, dried (sodium sulfate) and the solvent was removed in vacuum. Silicagel chromatography gave 260 mg of the title compound.

Intermediate Example IntP16.03

({[6-(4-{[(2R)-2-(4-fluorophenyl)propanoyl]amino}phenyl)[1,2,4]triazolo[1,5-α]pyridin-2-yl][4-(methylsulfonyl)-2-(2,2,2-trifluoroethoxy)phenyl]carbamoyl}oxy)methyl N-(tert-butoxycarbonyl)-3-methyl-L-valinate

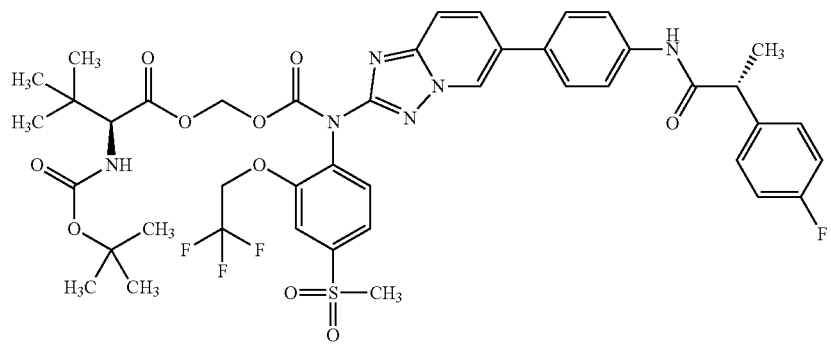 [SMILES: C[C@@H](C(=O)Nc1ccc(-c2ccc3nc(N(C(=O)OCOC(=O)[C@@H](NC(=O)OC(C)(C)C)C(C)(C)C)c4ccc(S(C)(=O)=O)cc4OCC(F)(F)F)nn3c2)cc1)c1ccc(F)cc1]

Starting with Intermediate Example IntP16.02 and (4-{[(2R)-2-(4-fluorophenyl)propanoyl]amino}phenyl)boronic acid, Intermediate Example IntP16.03. was prepared analogously to the procedure for the preparation of Intermediate Example IntP02.03.

Intermediate Example IntP17.01

({(6-chloro[1,2,4]triazolo[1,5-α]pyridin-2-yl)[4-(methylsulfonyl)-2-(2,2,2-trifluoroethoxy)phenyl]carbamoyl}oxy)methyl N-(tert-butoxycarbonyl)-L-valinate

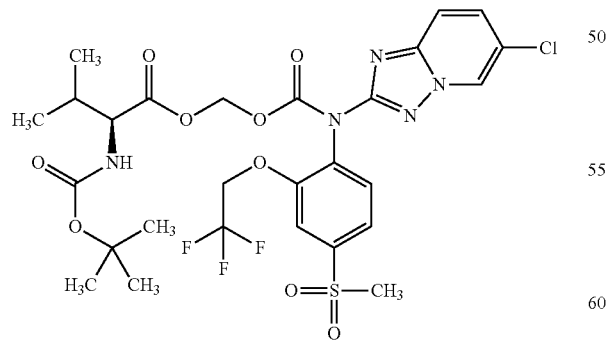

Starting with Intermediate Example IntP16.01 (230 mg) and IntP02.01 (250 mg) Intermediate Example IntP17.01. was prepared analogously to the procedure for the preparation of Intermediate Example IntP16.02.
Yield: 240 mg of the title compound.

Intermediate Example IntP17.02

({[6-(4-{[(2R)-2-(4-fluorophenyl)propanoyl]amino}phenyl)[1,2,4]triazolo[1,5-α]pyridin-2-yl][4-(methylsulfonyl)-2-(2,2,2-trifluoroethoxy)phenyl]carbamoyl}oxy)methyl N-(tert-butoxycarbonyl)-L-valinate

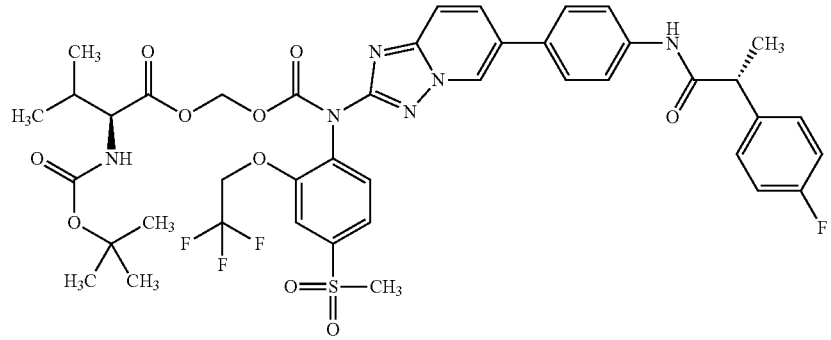 [SMILES: CC(C)[C@H](NC(=O)OC(C)(C)C)C(=O)OCOC(=O)N(c1nc2ccc(-c3ccc(NC(=O)[C@H](C)c4ccc(F)cc4)cc3)cn2n1)c1ccc(S(C)(=O)=O)cc1OCC(F)(F)F]

Starting with Intermediate Example IntP17.01 and (4-{[(2R)-2-(4-fluorophenyl)propanoyl]amino}phenyl)boronic acid, Intermediate Example IntP17.02. was prepared analogously to the procedure for the preparation of Intermediate Example IntP02.03.

Intermediate Example IntP18.01 chloromethyl (6-chloro[1,2,4]triazolo[1,5-α]pyridin-2-yl){4-[(3-fluoroazetidin-1-yl)carbonyl]-2-(2,2,2-trifluoroethoxy)phenyl}carbamate

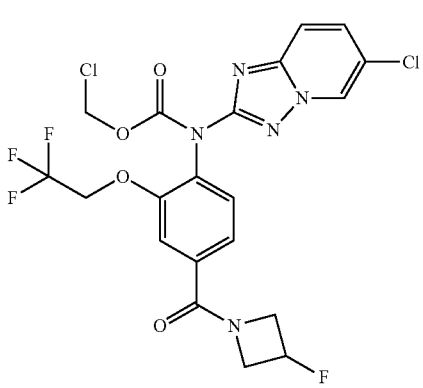 [SMILES: O=C(c1ccc(N(C(=O)OCCl)c2nc3ccc(Cl)cn3n2)c(OCC(F)(F)F)c1)N1CC(F)C1]

To a stirred solution of Intermediate Example Int06.05. (200 mg) in THF (10 mL) and NMP (2.0 mL) was added sodium hydride (55% w/w in oil; 98 mg) at room temperature and the mixture was stirred at room temperature for 15 minutes. Chloromethyl chloroformate (0.12 mL) was added and the mixture was stirred at room temperature for 1 hour. A half-saturated solution of ammonium chloride was added and the mixture was extracted with ethyl acetate. The organic phase was dried (sodium sulfate) and the solvent was removed in vacuum. Silicagel chromatography gave 153 mg of the title compound.

Intermediate Example IntP18.02

{[(6-chloro[1,2,4]triazolo[1,5-α]pyridin-2-yl){4-[(3-fluoroazetidin-1-yl)carbonyl]-2-(2,2,2-trifluoroethoxy)phenyl}carbamoyl]oxy}methyl N-(tert-butoxycarbonyl)-3-methyl-L-valinate

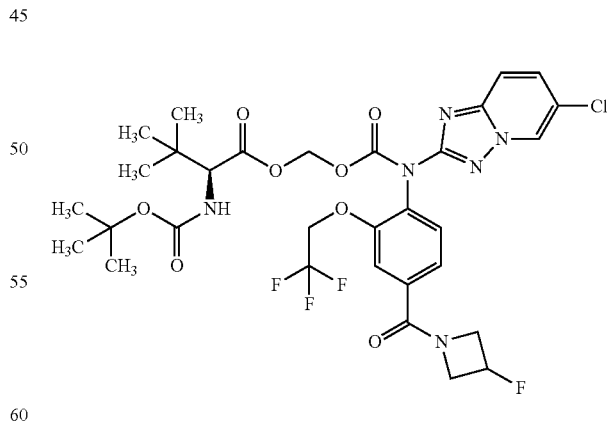

Starting with Intermediate Example IntP18.01 (150 mg) and caesium (2S)-2-[(tert-butoxycarbonyl)amino]-3,3-dimethylbutanoate (234 mg), Intermediate Example IntP18.02. was prepared analogously to the procedure for the preparation of Intermediate Example IntP16.02.

Yield: 153 mg of the title compound.

Intermediate Example IntP18.03

[({4-[(3-fluoroazetidin-1-yl)carbonyl]-2-(2,2,2-trifluoroethoxy)phenyl}[6-(4-{[(2R)-2-(4-fluorophenyl)propanoyl]amino}phenyl)[1,2,4]triazolo[1,5-α]pyridin-2-yl]carbamoyl)oxy]methyl N-(tert-butoxycarbonyl)-3-methyl-L-valinate

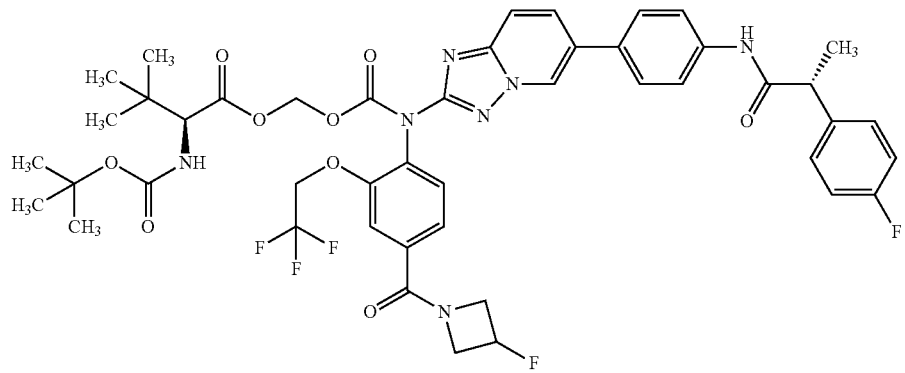 [SMILES: C[C@@H](C(=O)Nc1ccc(-c2ccc3nc(N(C(=O)OCOC(=O)[C@@H](NC(=O)OC(C)(C)C)C(C)(C)C)c4ccc(C(=O)N5CC(F)C5)cc4OCC(F)(F)F)nn3c2)cc1)c1ccc(F)cc1]

Starting with Intermediate Example IntP18.02 and (4-{[(2R)-2-(4-fluorophenyl)propanoyl]amino}phenyl)boronic acid, Intermediate Example IntP18.03. was prepared analogously to the procedure for the preparation of Intermediate Example IntP02.03.

Intermediate Example IntP19.01

1-chloro-2-methylpropyl (6-chloro[1,2,4]triazolo[1,5-α]pyridin-2-yl)[2-methoxy-4-(methylsulfonyl)phenyl]carbamate

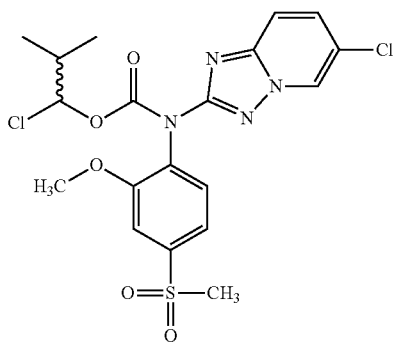 [SMILES: COc1cc(S(C)(=O)=O)ccc1N(C(=O)OC(Cl)C(C)C)c1nc2ccc(Cl)cn2n1]

To a stirred solution of 6-chloro-N-[2-methoxy-4-(methylsulfonyl)phenyl][1,2,4]triazolo[1,5-α]pyridin-2-amine (Int21.03) (4.00 g) in THF (200 mL) was added sodium hydride (55% w/w in oil; 2.47 g) at room temperature and the mixture was stirred at 0° C. for 15 minutes. 1-chloro-2-methylpropyl carbonochloridate (4.13 mL) was added and the mixture was stirred at room temperature for 4 hours. A half-saturated solution of sodium chloride was added and the mixture was extracted with ethyl acetate. The organic phase was dried (sodium sulfate) and the solvent was removed in vacuum. Silicagel chromatography gave 3.00 g of the title compound.

Intermediate Example IntP19.02

(1RS)-1-({(6-chloro[1,2,4]triazolo[1,5-α]pyridin-2-yl)[2-methoxy-4-(methylsulfonyl)phenyl]carbamoyl}oxy)-2-methylpropyl-N-(tert-butoxycarbonyl)-3-methyl-L-valinate

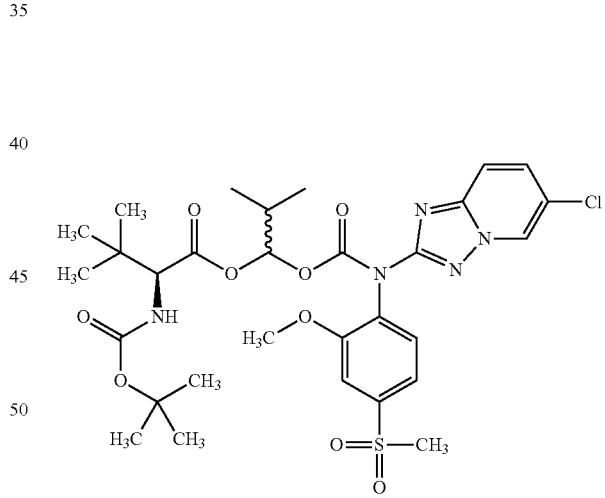

To a stirred solution of 1-chloro-2-methylpropyl (6-chloro[1,2,4]triazolo[1,5-α]pyridin-2-yl)[2-methoxy-4-(methylsulfonyl)phenyl]carbamate (2500 mg) in DMF (125 mL) was added caesium (2S)-2-[(tert-butoxycarbonyl)amino]-3,3-dimethylbutanoate (2981 mg) and the mixture was heated to 70° C. for 16 h. The mixture was added to a half-saturated solution of sodium chloride and the mixture was extracted with ethyl acetate. The organic phase was washed with saturated sodium chloride solution, dried (sodium sulfate), filtered and the solvent was removed in vacuum. Silicagel chromatography gave 2240 mg of the title compound.

Intermediate Example IntP19.03

(1RS)-1-({[6-(4-{[(2R)-2-(4-fluorophenyl)pro-
panoyl]amino}phenyl)[1,2,4]triazolo[1,5-α]pyridin-
2-yl][2-methoxy-4-(methylsulfonyl)phenyl]
carbamoyl}oxy)-2-methylpropyl N-(tert-
butoxycarbonyl)-3-methyl-L-valinate (Mixture of 2
Epimers)

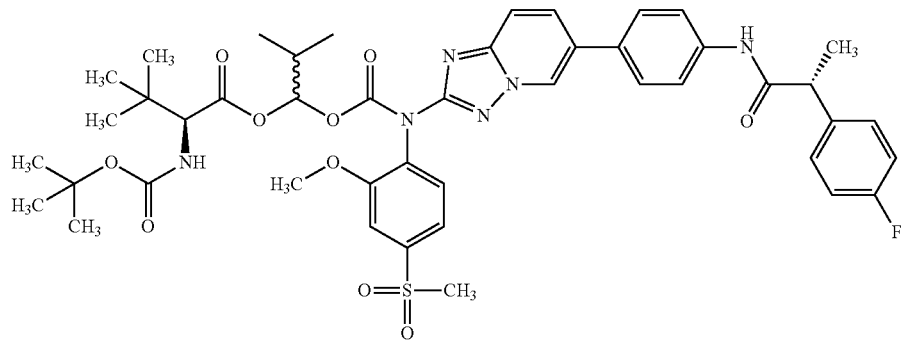 [SMILES: COc1cc(S(C)(=O)=O)ccc1N(C(=O)OC(OC(=O)[C@@H](NC(=O)OC(C)(C)C)C(C)(C)C)C(C)C)c1nc2ccc(-c3ccc(NC(=O)[C@H](C)c4ccc(F)cc4)cc3)cn2n1]

To a stirred suspension of (1RS)-1-({[(6-chloro[1,2,4]triazolo[1,5-α]pyridin-2-yl)[2-methoxy-4-(methylsulfonyl)phenyl]carbamoyl}oxy)-2-methylpropyl N-(tert-butoxycarbonyl)-3-methyl-L-valinate (2200 mg) in toluene (64.6 mL) and NMP (10.8 mL) was added (4-{[(2R)-2-(4-fluorophenyl)propanoyl]amino}phenyl) boronic acid (1389 mg), powdered potassium phosphate monohydrate (2738 mg), dicyclohexyl(2',6'-dimethoxybiphenyl-2-yl)phosphine (265 mg) and palladium acetate (72 mg) and the flask was degassed twice and backfilled with argon. The mixture was heated to reflux for 30 minutes. After cooling, the reaction mixture was diluted with water and extracted with ethyl acetate (3×). The combined organic phases were dried (sodium sulfate), filtered and the solvent was removed in vacuum. Silicagel chromatography gave 2200 mg of the title compound.

Intermediate Example IntP20.01

(1RS)-1-({[(6-chloro[1,2,4]triazolo[1,5-α]pyridin-2-
yl)[2-methoxy-4-(methylsulfonyl)phenyl]
carbamoyl}oxy)-2-methylpropyl-N-(tert-butoxycar-
bonyl)-L-valinate (Mixture of 2 Epimers)

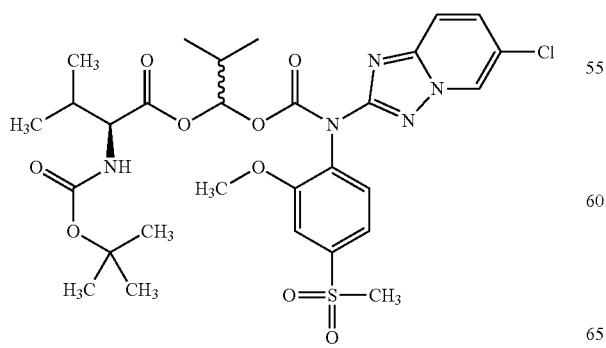

To a stirred solution of 1-chloro-2-methylpropyl (6-chloro[1,2,4]triazolo[1,5-α]pyridin-2-yl)[2-methoxy-4-(methylsulfonyl)phenyl]carbamate (5000 mg) in DMF (150 mL) was added caesium (2S)-2-[(tert-butoxycarbonyl)amino]-3-methylbutanoate (5373 mg) and the mixture was heated to 70° C. for 16 h. The mixture was added to water and extracted with ethyl acetate. The organic phase was washed with a half-saturated solution of sodium chloride, dried (sodium sulfate), filtered and the solvent was removed in vacuum. Preparative HPLC separation gave 4300 mg of the title compound.

Intermediate Example IntP20.02

(1RS)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)-2-methylpropyl-N-(tert-butoxycarbonyl)-L-valinate (Mixture of 2 Epimers) and Single Stereoisomers Intermediate Example IntP20.03 and Intermediate Example IntP20.04

|  | Retention time in min | purity in % | yield |
|---|---|---|---|
| Detection: UV 280 nm | | | |
| Intermediate Example IntP20.03 Stereoisomer A | 9.5-10.7 | >99.9% | 700 mg |
| Intermediate Example IntP20.04 Stereoisomer B | 10.9-12.4 | 97.1 | 725 mg |

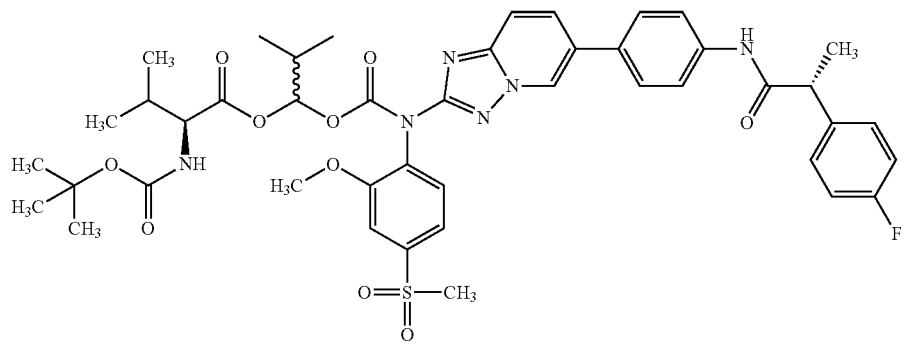 [SMILES: COc1cc(S(C)(=O)=O)ccc1N(C(=O)OC(OC(=O)[C@@H](NC(=O)OC(C)(C)C)C(C)C)C(C)C)c1nc2ccc(-c3ccc(NC(=O)[C@H](C)c4ccc(F)cc4)cc3)cn2n1]

To a stirred suspension of (1RS)-1-({[(6-chloro[1,2,4]triazolo[1,5-α]pyridin-2-yl)[2-methoxy-4-(methylsulfonyl)phenyl]carbamoyl}oxy)-2-methylpropyl-N-(tert-butoxycarbonyl)-L-valinate (2000 mg) in toluene (60.0 mL) and NMP (10.0 mL) was added (4-{[(2R)-2-(4-fluorophenyl)propanoyl]amino}phenyl) boronic acid (1289 mg), powdered potassium phosphate monohydrate (2541 mg), dicyclohexyl(2',6'-dimethoxybiphenyl-2-yl)phosphine (246 mg) and palladium acetate (67 mg) and the flask was degassed twice and backfilled with argon. The mixture was heated to reflux for 45 minutes. After cooling, the reaction mixture was diluted with water and extracted with ethyl acetate (3×). The combined organic phases were dried (sodium sulfate), filtered and the solvent was removed in vacuum. Silicagel chromatography gave 1500 mg of the title compound as a mixture of 2 stereoisomers (IntP20.02).

The mixture was separated into the single stereoisomers (Intermediate Example IntP20.03 and Intermediate Example IntP20.04.) via preparative, chiral HPLC.

| System: | Agilent: Prep 1200, 2 × Prep Pump, DLA, MWD, Gilson: Liquid Handler 215 |
|---|---|
| Column: | Chiralpak IB 5 μm 250 × 30 mm |
| Solvent: | Hexane/ethanol 70:30 (v/v) |
| Flow: | 50 mL/min |
| Temperature: | RT |
| Solution: | 1500 mg/19 mL DCM/MeOH |
| Injection: | 55 × 0.35 mL |

Intermediate Example IntP21.01 caesium 2-[(tert-butoxycarbonyl)amino]-2-methylpropanoate

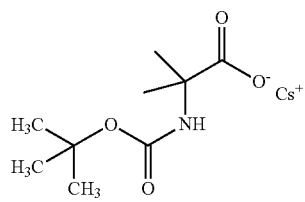

To a stirred solution of N-(tert-butoxycarbonyl)-2-methylalanine (4.00 g) in methanol (76 mL) was added a solution of caesium carbonate in water until pH 7 was reached (approx. 3.21 g caesium carbonate in 15 mL water) and the solution was stirred for 30 minutes. The solvent was removed in vacuum, toluene was added and the solvent was again removed in vacuum to give 7.00 g of the title compound.

Intermediate Example IntP21.02

(rac)-1-({(6-chloro[1,2,4]triazolo[1,5-α]pyridin-2-yl)[2-methoxy-4-(methylsulfonyl)phenyl]carbamoyl}oxy)-2-methylpropyl N-(tert-butoxycarbonyl)-2-methylalaninate

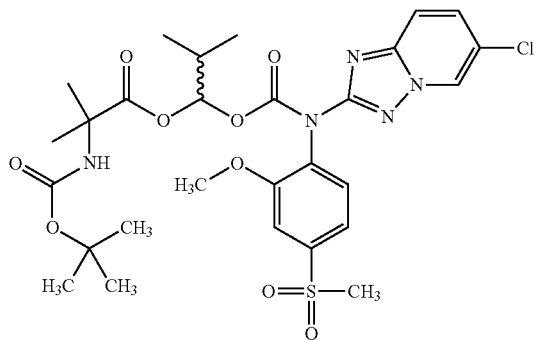 [SMILES: COc1cc(S(C)(=O)=O)ccc1N(C(=O)OC(OC(=O)C(C)(C)NC(=O)OC(C)(C)C)C(C)C)c1nc2ccc(Cl)cn2n1]

To a stirred solution of 1-chloro-2-methylpropyl (6-chloro[1,2,4]triazolo[1,5-α]pyridin-2-yl)[2-methoxy-4-(methylsulfonyl)phenyl]carbamate (2000 mg) in DMF (70 mL) was added caesium 2-[(tert-butoxycarbonyl)amino]-2-methylpropanoate (2063 mg) and the mixture was heated to 70° C. for 16 h. The mixture was added to water and extracted with ethyl acetate. The organic phase was washed with a half-saturated solution of sodium chloride, dried (sodium sulfate), filtered and the solvent was removed in vacuum. Preparative HPLC separation gave 1140 mg of the title compound.

Intermediate Example IntP21.03

(1RS)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)-2-methylpropyl-N-(tert-butoxycarbonyl)-2-methylalaninate (Mixture of 2 Epimers)

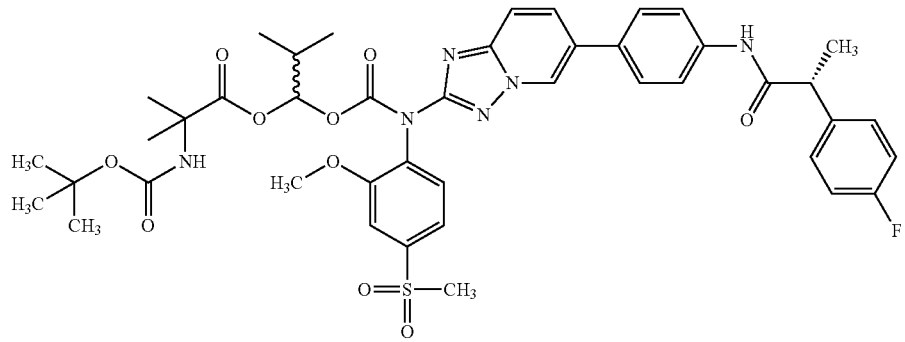 [SMILES: COc1cc(S(C)(=O)=O)ccc1N(C(=O)OC(OC(=O)C(C)(C)NC(=O)OC(C)(C)C)C(C)C)c1nc2ccc(-c3ccc(NC(=O)[C@H](C)c4ccc(F)cc4)cc3)cn2n1]

To a stirred suspension of 1-({(6-chloro[1,2,4]triazolo[1,5-α]pyridin-2-yl)[2-methoxy-4-(methylsulfonyl)phenyl]carbamoyl}oxy)-2-methylpropyl N-(tert-butoxycarbonyl)-2-methylalaninate (600 mg) in toluene (18.4 mL) and NMP (3.1 mL) was added (4-{[(2R)-2-(4-fluorophenyl)propanoyl]amino}phenyl) boronic acid (395 mg), powdered potassium phosphate monohydrate (779 mg), dicyclohexyl(2',6'-dimethoxybiphenyl-2-yl)phosphine (75 mg) and palladium acetate (21 mg) and the flask was degassed twice and backfilled with argon. The mixture was heated to reflux for 30 minutes. After cooling, the reaction mixture was diluted with water and extracted with ethyl acetate (3×). The combined organic phases were dried (sodium sulfate), filtered and the solvent was removed in vacuum. Silicagel chromatography gave 30 mg of the title compound as a mixture of 2 epimers.

Intermediate Example IntP22.01

4-nitrophenyl (6-chloro[1,2,4]triazolo[1,5-α]pyridin-2-yl)[2-methoxy-4-(methylsulfonyl)phenyl]carbamate

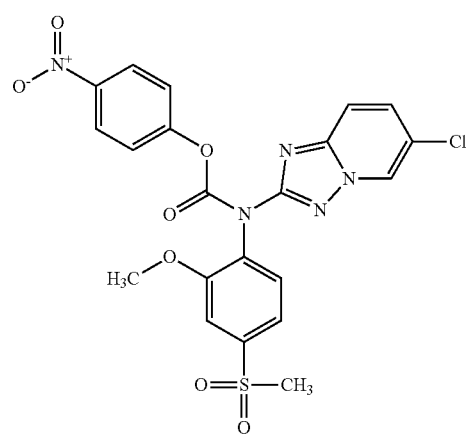 [SMILES: COc1cc(S(C)(=O)=O)ccc1N(C(=O)Oc1ccc([N+](=O)[O-])cc1)c1nc2ccc(Cl)cn2n1]

To a stirred solution of 6-chloro-N-[2-methoxy-4-(methylsulfonyl)phenyl][1,2,4]triazolo[1,5-α]pyridin-2-amine (Int21.03) (500 mg) in THF (50 mL) was added sodium hydride (55% w/w in oil; 1.24 g) at room temperature and the mixture was stirred at room temperature for 15 minutes. 4-Nitrophenyl chloroformate (0.29 mL) was added at 0° C. and the mixture was stirred at room temperature for 15 minutes. Aqueous hydrochloric acid (c=2M) was added until acidic pH was reached and the mixture was extracted with ethyl acetate. The organic phase was dried (sodium sulfate) and the solvent was removed in vacuum. Silicagel chromatography gave 725 mg of the title compound.

Intermediate Example IntP22.02 tert-butyl (2-hydroxyethyl)methylcarbamate

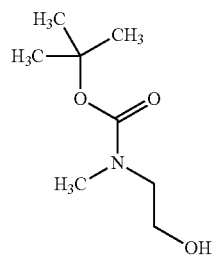

To a stirred suspension of 2-(methylamino)ethanol (5.0 g) in water (75 mL) was added potassium carbonate (15.3 g) and di-tert-butyl dicarbonate (12.1 g) and the mixture was stirred at room temperature for 16 hours. The mixture was extracted with dichloromethane. The organic phase was washed with saturated sodium chloride solution, dried (sodium sulfate) and the solvent was removed in vacuum. Aminophase-silica-gel chromatography gave 6.6 g of the title compound.

Intermediate Example IntP22.03

2-[(tert-butoxycarbonyl)(methyl)amino]ethyl (6-chloro[1,2,4]triazolo[1,5-α]pyridin-2-yl)[2-methoxy-4-(methylsulfonyl)phenyl]carbamate

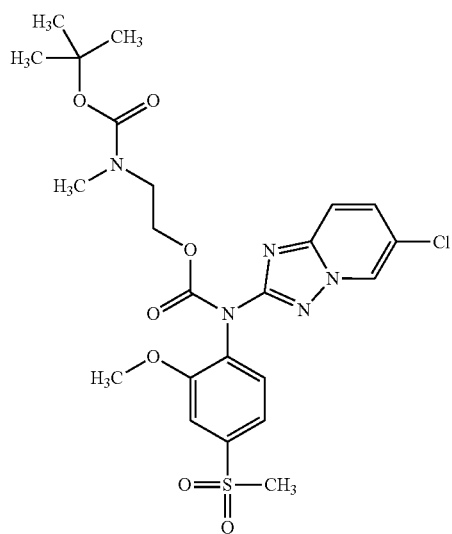 [SMILES: COc1cc(S(C)(=O)=O)ccc1N(C(=O)OCCN(C)C(=O)OC(C)(C)C)c1nc2ccc(Cl)cn2n1]

To a stirred solution of 4-nitrophenyl (6-chloro[1,2,4]triazolo[1,5-α]pyridin-2-yl)[2-methoxy-4-(methylsulfonyl)phenyl]carbamate (720 mg) in DMF (40 mL) was added caesium carbonate (4.53 g), and tert-butyl(2-hydroxyethyl) methylcarbamate (487 mg). The mixture was stirred at room temperature for 1 h. Water was added, and the mixture was extracted with ethyl acetate. The organic phase was washed with saturated sodium chloride solution, dried (sodium sulfate) and the solvent was removed in vacuum. Silicagel chromatography gave 425 mg of the title compound.

Intermediate Example IntP22.04

2-[(tert-butoxycarbonyl)(methyl)amino]ethyl [6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamate

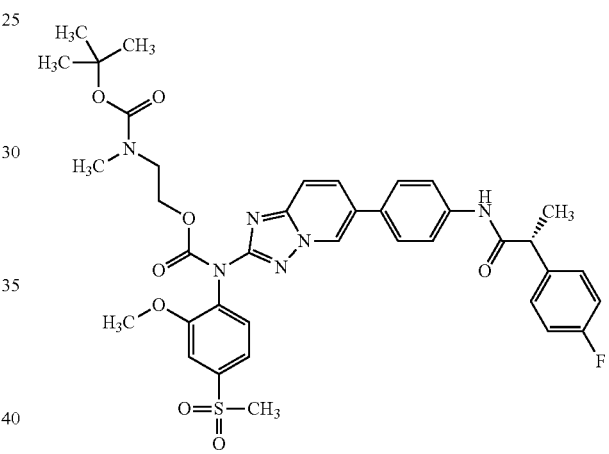

To a stirred suspension of 2-[(tert-butoxycarbonyl)(methyl)amino]ethyl (6-chloro[1, 2,4]triazolo[1,5-a]pyridin-2-yl)[2-methoxy-4-(methylsulfonyl)phenyl]carbamate (100 mg) in toluene (3.2 mL) was added potassium fluoride (47.2 mg) and powdered potassium phosphate (153 mg) and the flask was twice degassed and backfilled with argon. The mixture was stirred at room temperature for 15 minutes. (2R)-2-(4-fluorophenyl)-N-[4-(4,4,5,5-tetramethyl-1,3,2-dioxaborolan-2-yl)phenyl]propanamide (100 mg), dicyclohexyl(2',6'-dimethoxybiphenyl-2-yl)phosphine (14.8 mg) and palladium acetate (4.1 mg) were added and the flask was twice degassed and backfilled with argon. The mixture was heated to 85° C. for 5 h. Water was added and the reaction mixture was extracted with ethyl acetate. The organic phase was washed with saturated sodium chloride solution, dried (sodium sulfate) and the solvent was removed in vacuum. Silicagel chromatography followed by preparative reverse phase HPLC (gradient of water and acetonitrile containing conc. ammonium hydroxide as additive) gave 28 mg of the title compound.

Intermediate Example IntP23.01

2,5-dioxopyrrolidin-1-yl N-(tert-butoxycarbonyl)-N-methylglycinate

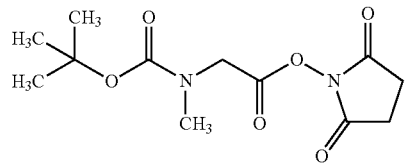 [SMILES: CN(CC(=O)ON1C(=O)CCC1=O)C(=O)OC(C)(C)C]

To a stirred solution of N,N'-dicyclohexylcarbodiimide (6.0 g) in THF (100 mL) at −5° C. was added N-(tert-butoxycarbonyl)-N-methylglycine (5.0 g) and 1-hydroxy-pyrrolidine-2,5-dione (4.7 g) and the mixture was allowed to warm up to room temperature over night. A solid was removed by filtration and the solution was concentrated in vacuum. Silicagel chromatography gave 5.0 g of the title compound.

Intermediate Example IntP23.02 tert-butyl (2-{(6-chloro[1,2,4]triazolo[1,5-α]pyridin-2-yl)[2-methoxy-4-(methylsulfonyl)phenyl]amino}-2-oxoethyl)methylcarbamate

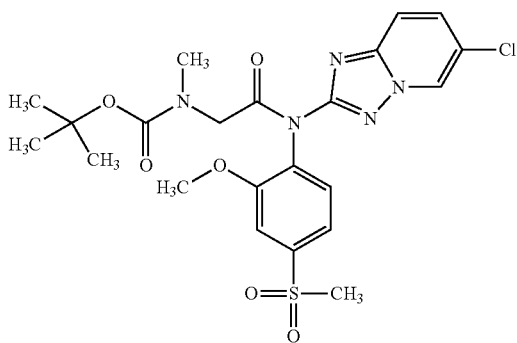 [SMILES: COc1cc(S(C)(=O)=O)ccc1N(C(=O)CN(C)C(=O)OC(C)(C)C)c1nc2ccc(Cl)cn2n1]

To a stirred solution of 6-chloro-N-[2-methoxy-4-(methylsulfonyl)phenyl][1,2,4]triazolo[1,5-α]pyridin-2-amine (Int21.03) (1.0 g) in THF (140 mL) was added sodium hydride (55% w/w in oil; 1.36 g) at room temperature and the mixture was stirred at room temperature for 15 minutes. 2,5-dioxopyrrolidin-1-yl N-(tert-butoxycarbonyl)-N-methylglycinate (1.62 g) was added and the mixture was stirred at room temperature for 10 minutes. A half-saturated aqueous solution of ammonium chloride was added and the mixture was extracted with ethyl acetate. The organic phase was dried (sodium sulfate) and the solvent was removed in vacuum. The residue was dissolved in dichloromethane and filtered through silicagel, and eluted with a mixture of dichloromethane and methanol (95:5) to give the crude product as a solid. The solid was triturated with warm ethanol, undissolved material was removed by filtration and the solution was concentrated in vacuum. Silicagel chromatography gave 1.2 g of the title compound.

Intermediate Example IntP23.03 tert-butyl (2-{[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]amino}-2-oxoethyl)methylcarbamate

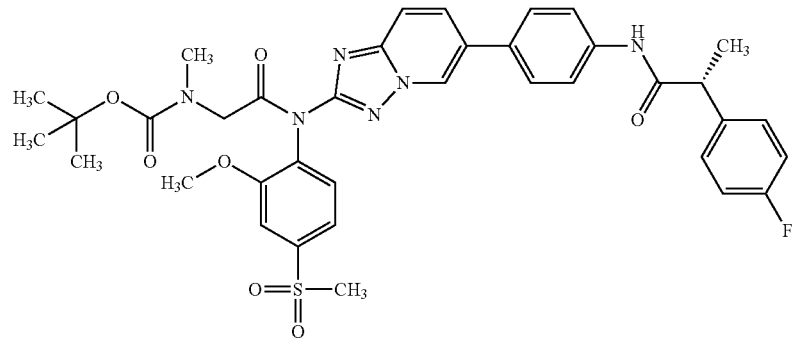 [SMILES: COc1cc(S(C)(=O)=O)ccc1N(C(=O)CN(C)C(=O)OC(C)(C)C)c1nc2ccc(-c3ccc(NC(=O)[C@H](C)c4ccc(F)cc4)cc3)cn2n1]

To a stirred suspension of tert-butyl (2-{(6-chloro[1,2,4]triazolo[1,5-α]pyridin-2-yl)[2-methoxy-4-(methylsulfonyl)phenyl]amino}-2-oxoethyl)methylcarbamate (350 mg) in toluene (11.7 mL) and NMP (0.58 mL) was added (4-{[(2R)-2-(4-fluorophenyl)propanoyl]amino}phenyl)boronic acid (249 mg), powdered potassium phosphate monohydrate (567 mg), dicyclohexyl(2',6'-dimethoxybiphenyl-2-yl)phosphine (54.8 mg) and Pd$_2$(dba)$_3$ (30.6 mg) and the flask was degassed twice and backfilled with argon. The mixture was heated to 90° C. for 60 minutes. The reaction mixture was filtered, water was added and the mixture was extracted with ethyl acetate. The organic phase was washed with saturated sodium chloride solution, dried (sodium sulfate) and the solvent was removed in vacuum. Silicagel chromatography followed by aminophase-silica-gel chromatography gave 170 mg of the title compound.

Intermediate Example 4.01A

Benzyl (4-chloro-4-oxobutyl)methylcarbamate

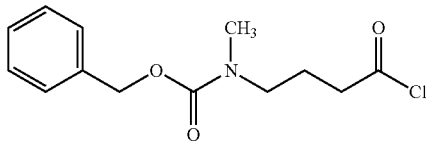 [SMILES: CN(CCCC(=O)Cl)C(=O)OCc1ccccc1]

The starting material, 4-[[(benzyloxy)carbonyl](methyl)amino]butyric acid, was prepared by a literature procedure [Y. Aramaki et al., Chem. Pharm. Bull. 52, 258 (2004)] from commercially available 4-{[(benzyloxy)carbonyl]amino}butyric acid. An alternative preparation was also to introduce the benzyloxycarbonyl protective group into ω-N-methylaminoalkylcarboxylic acids which were obtainable according to P. Quitt et al. [Helv. Chim. Acta 46, 327 (1963)].

1.74 g (6.92 mmol) of 4-[[(benzyloxy)carbonyl](methyl)amino]butyric acid were dissolved in 35 ml of dichloromethane and 3.5 ml (48 mmol) of thionyl chloride were added. The mixture was heated under reflux for 1 h. It was then concentrated in vacuo, and the residue was again mixed with dichloromethane and concentrated once again. A viscous oil remained and was dried under high vacuum. 1.8 g (96% of theory) of the target compound were obtained and were reacted further without further purification and characterization.

Intermediate Example 4.02A

4-{[(benzyloxy)carbonyl](methyl)amino}butanoic anhydride

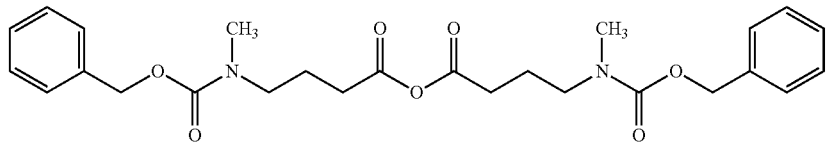 [SMILES: CN(CCCC(=O)OC(=O)CCCN(C)C(=O)OCc1ccccc1)C(=O)OCc1ccccc1]

The starting material, 4-[[(benzyloxy)carbonyl](methyl)amino]butyric acid, was prepared by a literature procedure [Y. Aramaki et al., Chem. Pharm. Bull. 52, 258 (2004)] from commercially available 4-{[(benzyloxy)carbonyl]amino}butyric acid. An alternative preparation was also to introduce the benzyloxycarbonyl protective group into ω-N-methylaminoalkylcarboxylic acids which were obtainable according to P. Quitt et al. [Helv. Chim. Acta 46, 327 (1963)].

2.36 g (9.39 mmol) of 4-[[(benzyloxy)carbonyl](methyl)amino]butyric acid were dissolved in 30 ml of dichloromethane and 0.969 g (4.7 mmol) of dicyclohexyl carbodiimide were added. The mixture was treated in ultrasonic equipment for 2 h. It was then concentrated in vacuo to about half of the original volume and the precipitate was filtered off. The remaining solution was concentrated in vacuo to dryness and the residue was dried under high vacuum. 2.33 g (84% of theory) of the target compound were obtained and reacted further without further purification.

LC-MS (method 1): R$_t$=1.2 min; m/z=485 (M+H)$^+$.

Intermediate Example 4.03A

5-{[(benzyloxy)carbonyl](4-methoxybenzyl)amino}butanoic anhydride

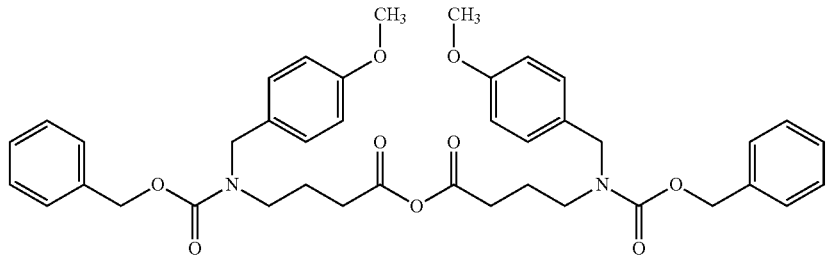 [SMILES: COc1ccc(CN(CCCC(=O)OC(=O)CCCN(Cc2ccc(OC)cc2)C(=O)OCc2ccccc2)C(=O)OCc2ccccc2)cc1]

Step a): 4-[(4-methoxybenzyl)amino]butanoic acid 20 g (194 mmol) of 4-aminobutanoic acid, 39.6 g (291 mmol) of p-anisaldehyde and 14 g (116 mmol) of magnesium sulphate were taken up in 300 ml of ethanol and heated under reflux overnight. The solid was filtered off and washed with ethanol. Subsequently a total of 4.4 g (116 mmol) of sodium borohydride were added in portions to the filtrate over the course of 15 min. The mixture was concentrated in vacuo and then 582 ml of a 2 M sodium hydroxide solution were added. After 5 min the mixture was extracted with 500 ml dichloromethane and twice with 200 ml of ethyl acetate each time. The aqueous phase was concentrated in vacuo. The residue was dried under high vacuum and reacted in the next step without further purification.

Step b): 4-{[(benzyloxy)carbonyl](4-methoxybenzyl)amino}butanoic acid 43 g of the crude p-methoxybenzyl protected 4-aminobutanoic acid derivative obtained in this way was taken up in dioxane/2M NaOH (1:1). 49 g (288 mmol) of benzyl chlorocarbonate were added dropwise and the pH was kept at 11-12 by adding 2M NaOH. After stirring at RT for 30 min, the dioxane was removed in vacuo and the remaining solution was adjusted to pH 2 with 2 M hydrochloric acid. The solution was extracted twice with 500 ml ethyl acetate. The organic phase was washed with a saturated solution of ammonium chloride and then concentrated in vacuo. The residue was dried under high vacuum and reacted in the next step without further purification.

Step c): 5-{[(benzyloxy)carbonyl](4-methoxybenzyl)amino}butanoic anhydride 1920 mg (5.372 mmol) of crude 4-[[(benzyloxy)carbonyl](4-methoxybenzyl)amino]butanoic acid were dissolved in 20 ml of dichloromethane and 554 mg (2.69 mmol) of dicyclohexyl carbodiimide were added. The mixture was stirred at RT for 1 h. It was then concentrated in vacuo to half of the original volume and the precipitate was filtered off. The remaining solution was concentrated in vacuo to dryness and the residue was dried under high vacuum. 1900 mg (97% of theory) of the target compound were obtained and reacted further without further purification.

LC-MS (method 1): $R_t$=1.43 min; m/z=697 (M+H)$^+$.

Compounds of the Present Invention

Example 1.1

({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)methyl piperidine-4-carboxylate trifluoroacetate

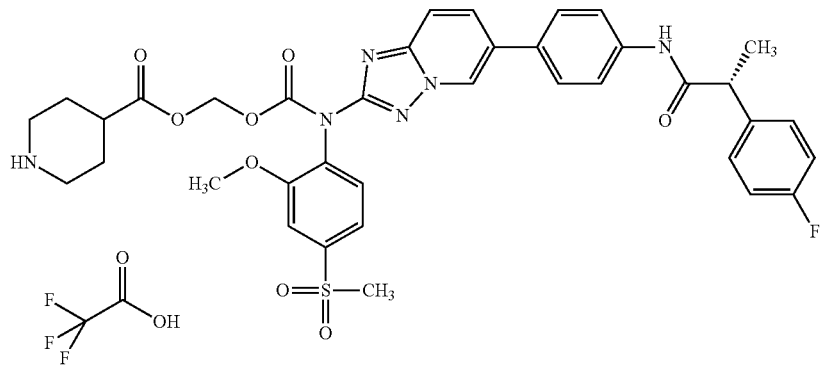 [SMILES: COc1cc(S(C)(=O)=O)ccc1N(C(=O)OCOC(=O)C1CCNCC1)c1nc2ccc(-c3ccc(NC(=O)[C@H](C)c4ccc(F)cc4)cc3)cn2n1 ; O=C(O)C(F)(F)F]

To a stirred solution of Intermediate Example IntP01.03 (90 mg) in dichloromethane (5 mL) and methanol (0.5 mL) was added a solution of hydrochloric acid in dioxane (2.66 mL; c=4.0 M). The mixture was stirred at room temperature for 10 minutes. The solvent was removed in vacuum. Preparative reverse phase HPLC followed by lyophilisation gave 14 mg of the title compound.

$^1$H-NMR (300 MHz, DMSO-$d_6$, detected signals), δ [ppm]=1.41 (3H), 1.61-1.78 (2H), 1.94-2.06 (2H), 2.74-2.85 (1H), 2.88-3.03 (2H), 3.19-3.29 (2H), 3.80-3.90 (4H), 5.72-5.83 (2H), 7.12-7.20 (2H), 7.42 (2H), 7.55 (2H), 7.64 (1H), 7.66-7.75 (4H), 7.79 (1H), 8.01 (1H), 8.24 (1H), 8.49 (1H), 9.19 (1H), 10.23 (1H).

Example 1.2

({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)methyl L-valinate hydrochloride

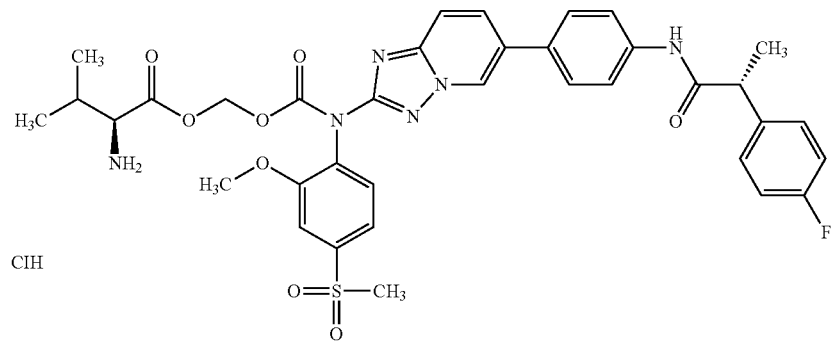 [SMILES: "CIH" ; COc1cc(S(C)(=O)=O)ccc1N(C(=O)OCOC(=O)[C@@H](N)C(C)C)c1nc2ccc(-c3ccc(NC(=O)[C@H](C)c4ccc(F)cc4)cc3)cn2n1]

To a stirred solution of Intermediate Example IntP02.03 (284 mg) in dichloromethane (3.5 mL) and methanol (0.35 mL) was added a solution of hydrochloric acid in dioxane (1.1 mL; c=4.0 M). The mixture was stirred at room temperature for 20 minutes. The solvent was removed in vacuum. The solid residue was triturated with dichloromethane for three times, the solvent was removed each time and the solid was dried in vacuum to give 255 mg of the title compound.

$^1$H-NMR (300 MHz, DMSO-$d_6$), δ [ppm]=0.92 (3H), 0.96 (3H), 1.41 (3H), 2.18 (1H), 3.32 (3H), 3.84-3.96 (4H), 4.03 (1H), 5.85 (1H), 5.97 (1H), 7.10-7.20 (2H), 7.44 (2H), 7.52-7.61 (2H), 7.65 (1H), 7.72 (4H), 7.79 (1H), 8.01 (1H), 8.52 (3H), 9.20 (1H), 10.38 (1H).

Example 1.3

({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)methyl L-leucinate hydrochloride

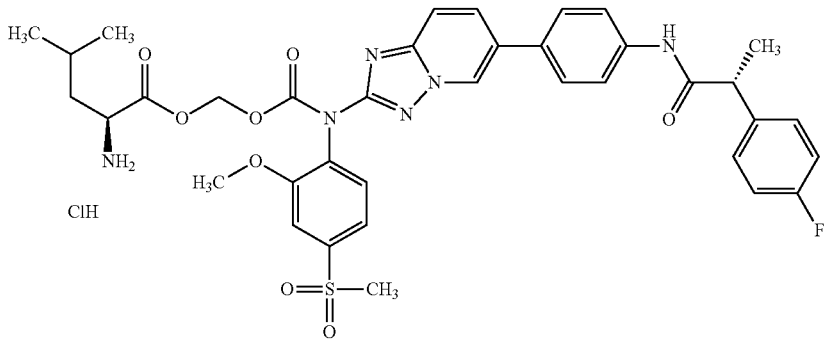 [SMILES: COc1cc(S(C)(=O)=O)ccc1N(C(=O)OCOC(=O)[C@@H](N)CC(C)C)c1nc2ccc(-c3ccc(NC(=O)[C@H](C)c4ccc(F)cc4)cc3)cn2n1 ; Cl]

To a stirred solution of Intermediate Example IntP03.03 (69 mg) in dichloromethane (0.8 mL) was added a solution of hydrochloric acid in dioxane (0.41 mL; c=4.0 M). The mixture was stirred at room temperature for 20 minutes. A solid precipitated. The solvent was removed by decantation. The solid residue was triturated with dichloromethane for three times, the solvent was removed each time and the solid was dried in vacuum to give 56 mg of the title compound.

$^1$H-NMR (300 MHz, DMSO-$d_6$), δ [ppm]=0.89 (6H), 1.41 (3H), 1.59-1.68 (2H), 1.74 (1H), 3.32 (3H), 3.81-3.97 (4H), 4.03-4.14 (1H), 5.86 (1H), 5.93 (1H), 7.15 (2H), 7.44 (2H), 7.53-7.61 (2H), 7.65 (1H), 7.72 (4H), 7.79 (1H), 8.02 (1H), 8.54 (3H), 9.20 (1H), 10.39 (1H).

Example 1.4

({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)methyl N-methyl-L-valinate hydrochloride temperature for 30 minutes. The solvent was removed in vacuum. The solid residue was triturated with dichloromethane for three times, the solvent was removed each time and the solid was dried in vacuum to give the title compound with some remaining starting material. Dichloromethane (0.5 mL) and a solution of hydrochloric acid in dioxane (0.25 mL; c=4.0 M) were added and the mixture was stirred at room temperature for 30 minutes. The solvent was removed in vacuum. The solid residue was triturated with dichloromethane for three times, the solvent was removed each time and the solid was dried in vacuum to give 58 mg of the title compound.

$^1$H-NMR (300 MHz, DMSO-$d_6$, detected signals), δ [ppm]=0.88 (3H), 1.01 (3H), 1.41 (3H), 2.21-2.34 (1H), 2.54-2.60 (3H), 3.32 (3H), 3.91 (3H), 4.11 (1H), 5.86 (1H), 6.00 (1H), 7.15 (2H), 7.43 (2H), 7.52-7.61 (2H), 7.65 (1H), 7.72 (4H), 7.79 (1H), 8.02 (1H), 9.14-9.44 (3H), 10.34 (1H).

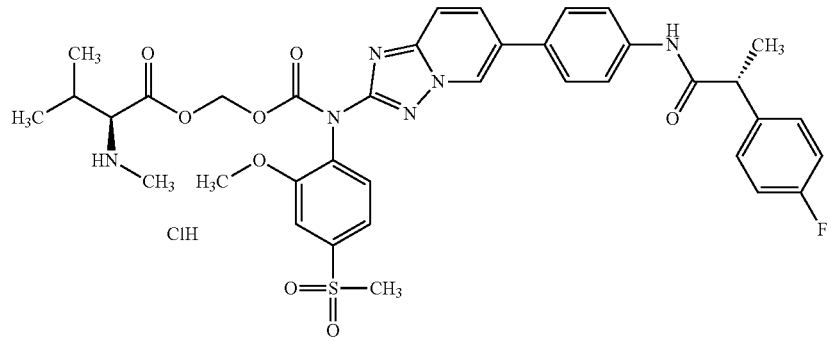 [SMILES: CN[C@H](C(=O)OCOC(=O)N(c1nc2ccc(-c3ccc(NC(=O)[C@H](C)c4ccc(F)cc4)cc3)cn2n1)c1ccc(S(C)(=O)=O)cc1OC)C(C)C ; Cl]

Example 1.5

({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)methyl 3-methyl-L-valinate hydrochloride

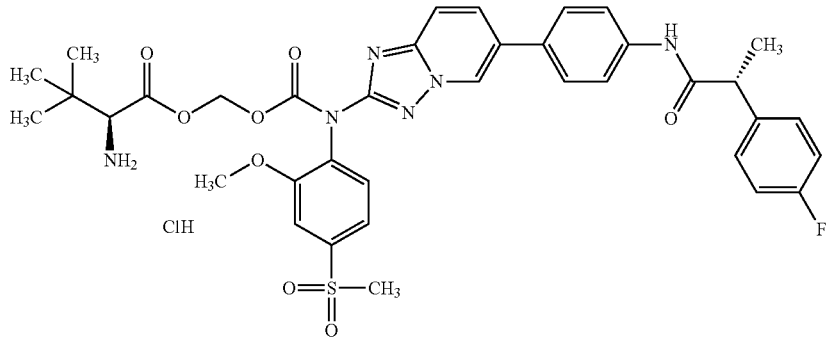 [SMILES: COc1cc(S(C)(=O)=O)ccc1N(C(=O)OCOC(=O)[C@@H](N)C(C)(C)C)c1nc2ccc(-c3ccc(NC(=O)[C@H](C)c4ccc(F)cc4)cc3)cn2n1 ; Cl]

To a stirred solution of Intermediate Example IntP04.03 (108 mg) in dichloromethane (2.5 mL) and methanol (0.76 mL) was added a solution of hydrochloric acid in dioxane (1.28 mL; c=4.0 M). The mixture was stirred at room To a stirred solution of Intermediate Example IntP05.03 (218 mg) in dichloromethane (4.0 mL) and methanol (0.4 mL) was added a solution of hydrochloric acid in dioxane (1.3 mL; c=4.0 M). The mixture was stirred at room temperature for 20 minutes. The solvent was removed in vacuum. The solid residue was triturated with dichloromethane for three times, the solvent was removed each time and the solid was dried in vacuum to give 170 mg of the title compound.

$^1$H-NMR (400 MHz, DMSO-d$_6$, detected signals), δ [ppm]=0.98 (9H), 1.41 (3H), 3.31 (3H), 3.84-3.94 (4H), 5.85 (1H), 5.97 (1H), 7.10-7.20 (2H), 7.40-7.46 (2H), 7.53-7.61 (2H), 7.64 (1H), 7.72 (4H), 7.78 (1H), 8.01 (1H), 8.44 (3H), 9.18 (1H), 10.33 (1H).

Example 1.6

(phosphonooxy)methyl [6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamate

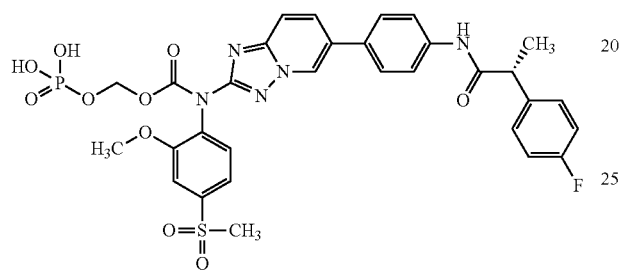

To a stirred solution of Intermediate Example IntP06.02 (33 mg) in dichloromethane (250 μL) was added a solution of hydrochloric acid in dioxane (30 μL; c=4.0 M). The mixture was stirred at room temperature for 40 minutes. A solid precipitated. The solvent was removed by decantation. The solid residue was triturated with dichloromethane for two times, the solvent was removed each time and the solid was dried in vacuum to give 22 mg of the title compound.

$^1$H-NMR (400 MHz, DMSO-d$_6$, detected signals), δ [ppm]=1.41 (3H), 3.31 (3H), 3.82-3.91 (4H), 5.52 (1H), 5.55 (1H), 7.11-7.19 (2H), 7.39-7.46 (2H), 7.52-7.64 (3H), 7.66-7.74 (4H), 7.78 (1H), 8.00 (1H), 9.20 (1H), 10.24 (1H).

Example 1.7

({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)methyl 3-methyl-L-isovalinate hydrochloride

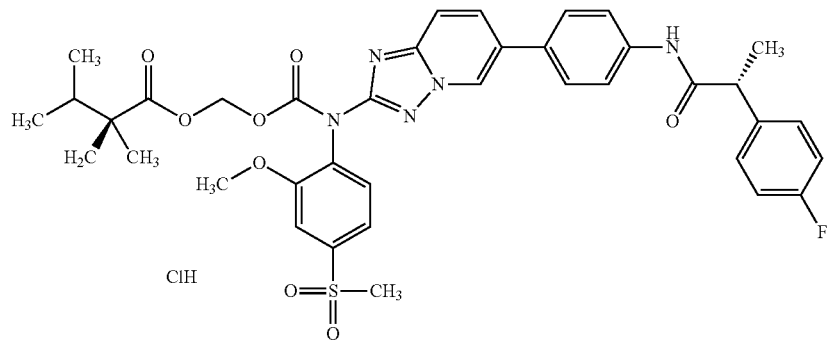

Starting with Intermediate Example IntP10.03, Example 1.7. was prepared analogously to the procedure for the preparation of Example 1.5.

$^1$H-NMR (300 MHz, DMSO-d$_6$), δ [ppm]=0.90 (6H), 1.35-1.51 (6H), 2.01-2.17 (1H), 3.32 (3H), 3.81-3.97 (4H), 5.83-5.97 (2H), 7.15 (2H), 7.44 (2H), 7.53-7.61 (2H), 7.65 (1H), 7.72 (4H), 7.79 (1H), 8.01 (1H), 8.59 (3H), 9.20 (1H), 10.38 (1H).

Example 1.8

({[6-(4-{[(2R)-2-(4-fluorophenyl)propanoyl]
amino}phenyl)[1,2,4]triazolo[1,5-α]pyridin-2-yl][2-
methoxy-4-(methylsulfonyl)phenyl]carbamoyl}oxy)
methyl 3-amino-2, 2-dimethylpropanoate
trifluoroacetate

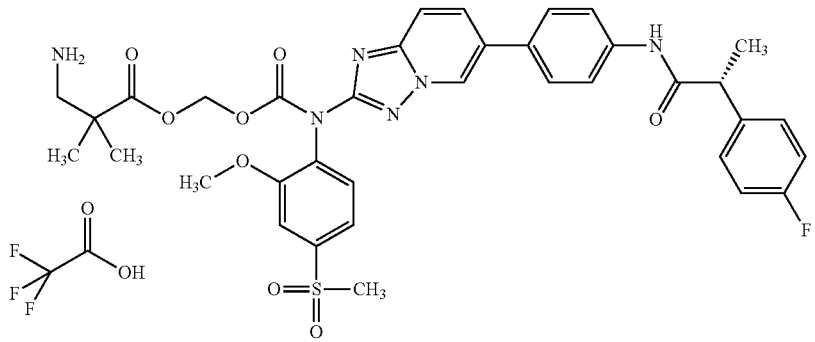

Starting with Intermediate Example IntP11.03, Example 1.8. was prepared analogously to the procedure for the preparation of Example 1.5. Final purification by preparative reverse phase HPLC (gradient of water and acetonitrile containing trifluoroacetic acid as additive) gave the title compound after lyophilisation.

$^1$H-NMR (300 MHz, DMSO-$d_6$), δ [ppm]=1.22 (6H), 1.41 (3H), 3.00 (2H), 3.32 (3H), 3.78-3.91 (4H), 5.80 (2H), 7.16 (2H), 7.42 (2H), 7.56 (2H), 7.62-7.92 (9H), 8.01 (1H), 9.20 (1H), 10.23 (1H).

Example 2.1

({[6-(4-{[(2R)-2-(4-fluorophenyl)propanoyl]
amino}phenyl)[1,2,4]triazolo[1,5-α]pyridin-2-yl][2-
methoxy-4-(methylsulfonyl)phenyl]carbamoyl}oxy)
methyl L-lysyl-L-valinate dihydrochloride To a stirred solution of Intermediate Example IntP07.01 (57 mg) in dichloromethane (1.1 mL) and methanol (0.3 mL) was added a solution of hydrochloric acid in dioxane (0.36 mL; c=4.0 M). The mixture was stirred at room temperature for 40 minutes. The solvent was removed in vacuum. The solid residue was triturated with dichloromethane for three times, the solvent was removed each time and the solid was dried in vacuum to give 27 mg of the title compound.

$^1$H-NMR (300 MHz, DMSO-$d_6$, detected signals), δ [ppm]=0.90 (6H), 1.41 (5H), 1.48-1.63 (2H), 1.73 (2H), 2.11 (1H), 2.72 (2H), 3.32 (3H), 3.84-3.95 (4H), 4.27 (1H), 5.72-5.79 (1H), 5.86 (1H), 7.15 (2H), 7.43 (2H), 7.56 (2H), 7.64 (1H), 7.72 (4H), 7.79 (1H), 7.91 (3H), 8.02 (1H), 8.27 (3H), 8.84 (1H), 9.20 (1H), 10.37 (1H).

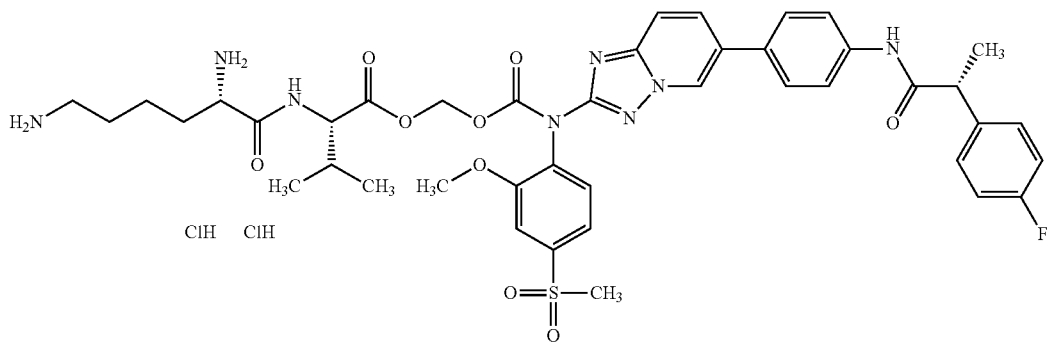 [SMILES: COc1cc(S(C)(=O)=O)ccc1N(C(=O)OCOC(=O)[C@@H](NC(=O)[C@@H](N)CCCCN)C(C)C)c1nc2ccc(-c3ccc(NC(=O)[C@H](C)c4ccc(F)cc4)cc3)cn2n1 ; Cl ; Cl]

Example 2.2

(1RS)-1-({[6-(4-{[(2R)-2-(4-fluorophenyl)pro-
panoyl]amino}phenyl)[1,2,4]triazolo[1,5-α]pyridin-
2-yl][2-methoxy-4-(methylsulfonyl)phenyl]
carbamoyl}oxy)ethyl L-lysyl-L-valinate
dihydrochloride (Mixture of 2 Epimers)

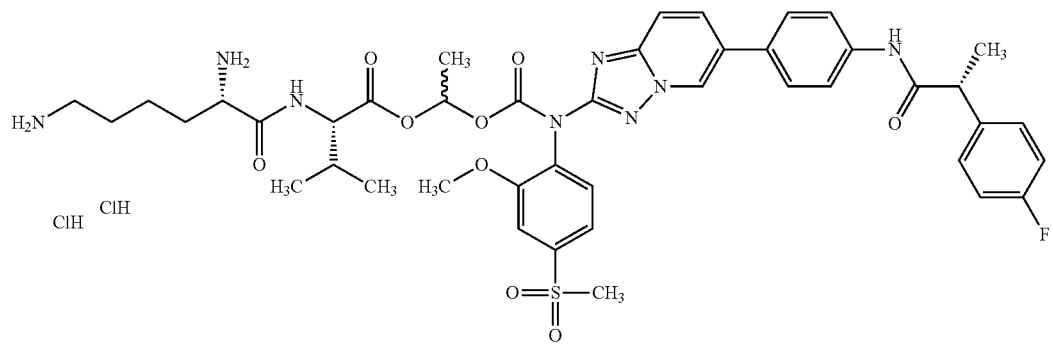 [SMILES: COc1cc(S(C)(=O)=O)ccc1N(C(=O)OC(C)OC(=O)[C@@H](NC(=O)[C@@H](N)CCCCN)C(C)C)c1nc2ccc(-c3ccc(NC(=O)[C@H](C)c4ccc(F)cc4)cc3)cn2n1 ; Cl ; Cl]

Starting with Intermediate Example IntP12.01, Example 2.2. was prepared analogously to the procedure for the preparation of Example 2.1.

$^1$H-NMR (400 MHz, DMSO-$d_6$), δ [ppm]=0.77-0.91 (6H), 1.32-1.47 (8H), 1.57 (2H), 1.67-1.79 (2H), 1.97-2.14 (1H), 2.73 (2H), 3.31 (3H), 3.88 (3H), 3.90-3.96 (2H), 4.18-4.27 (1H), 6.81 (1H), 7.09-7.19 (2H), 7.44 (2H), 7.49-7.59 (2H), 7.63 (1H), 7.72 (4H), 7.78 (1H), 7.88-8.05 (4H), 8.28 (3H), 8.80 (1H), 9.18 (1H), 10.38 (1H).

Example 2.3

({[6-(4-{[(2R)-2-(4-fluorophenyl)propanoyl]
amino}phenyl)[1,2,4]triazolo[1,5-α]pyridin-2-yl][2-
methoxy-4-(methylsulfonyl)phenyl]carbamoyl}oxy)
methyl L-valyl-L-valinate hydrochloride

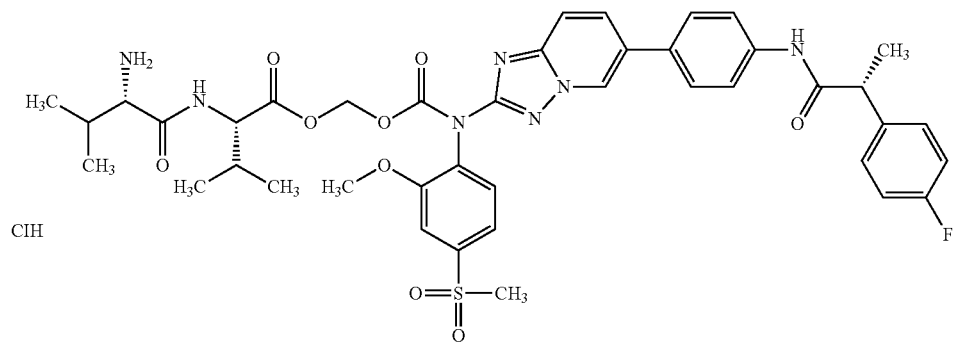 [SMILES: "CIH" ; COc1cc(S(C)(=O)=O)ccc1N(C(=O)OCOC(=O)[C@@H](NC(=O)[C@@H](N)C(C)C)C(C)C)c1nc2ccc(-c3ccc(NC(=O)[C@H](C)c4ccc(F)cc4)cc3)cn2n1]

Starting with Intermediate Example IntP13.01, Example 2.3. was prepared analogously to the procedure for the preparation of Example 2.1.

$^1$H-NMR (400 MHz, DMSO-$d_6$), δ [ppm]=0.85-0.98 (12H), 1.41 (3H), 2.02-2.16 (2H), 3.31 (3H), 3.70-3.75 (1H), 3.86 (3H), 3.89-3.93 (1H), 4.27 (1H), 5.76 (1H), 5.86 (1H), 7.15 (2H), 7.38-7.47 (2H), 7.55 (2H), 7.63 (1H), 7.72 (4H), 7.75-7.80 (1H), 8.00 (1H), 8.14 (3H), 8.66 (1H), 9.15-9.22 (1H), 10.32 (1H).

Example 2.4

(1RS)-1-({[6-(4-{[(2R)-2-(4-fluorophenyl)pro-
panoyl]amino}phenyl)[1,2,4]triazolo[1,5-α]pyridin-
2-yl][2-methoxy-4-(methylsulfonyl)phenyl]
carbamoyl}oxy)ethyl L-valyl-L-valinate
hydrochloride (Mixture of 2 Epimers)

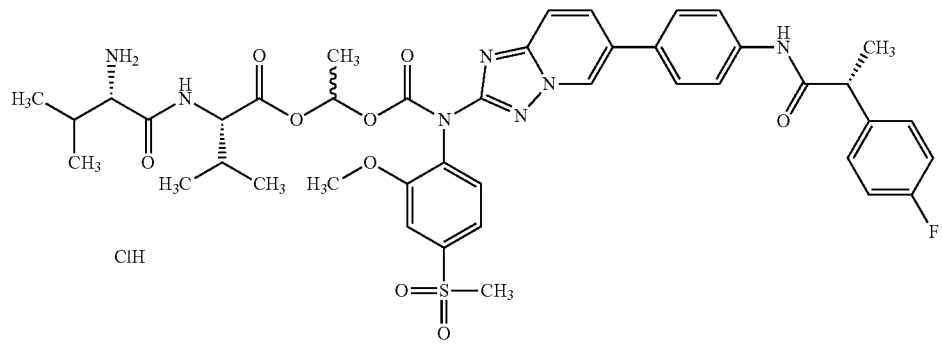 [SMILES: COc1cc(S(C)(=O)=O)ccc1N(C(=O)OC(C)OC(=O)[C@@H](NC(=O)[C@@H](N)C(C)C)C(C)C)c1nc2ccc(-c3ccc(NC(=O)[C@H](C)c4ccc(F)cc4)cc3)cn2n1 ; Cl]

Starting with Intermediate Example IntP14.01, Example 2.4. was prepared analogously to the procedure for the preparation of Example 2.1.

$^1$H-NMR (400 MHz, DMSO-$d_6$), δ [ppm]=0.78-0.98 (12H), 1.33-1.45 (6H), 2.06 (2H), 3.30 (3H), 3.68-3.78 (1H), 3.83-3.95 (4H), 4.15-4.26 (1H), 6.81 (1H), 7.10-7.20 (2H), 7.40-7.47 (2H), 7.49-7.57 (2H), 7.62 (1H), 7.68-7.74 (4H), 7.77 (1H), 8.00 (1H), 8.16 (3H), 8.65 (1H), 9.18 (1H), 10.37 (1H).

Example 3.1

(1RS)-1-({[6-(4-{[(2R)-2-(4-fluorophenyl)pro-
panoyl]amino}phenyl)[1,2,4]triazolo[1,5-α]pyridin-
2-yl][2-methoxy-4-(methylsulfonyl)phenyl]
carbamoyl}oxy)ethyl L-valinate hydrochloride
(Mixture of 2 Epimers)

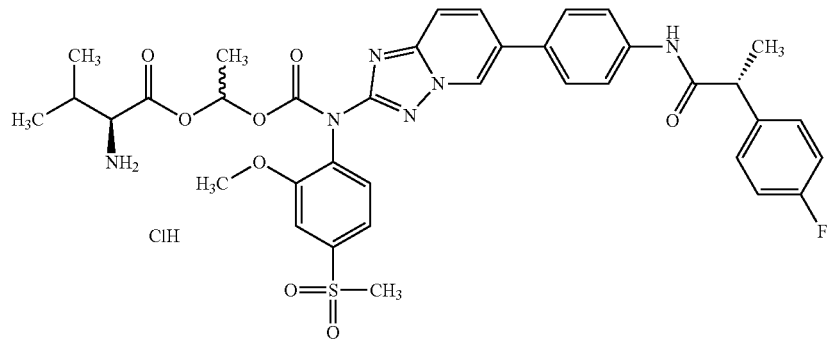 [SMILES: COc1cc(S(C)(=O)=O)ccc1N(C(=O)OC(C)OC(=O)[C@@H](N)C(C)C)c1nc2ccc(-c3ccc(NC(=O)[C@H](C)c4ccc(F)cc4)cc3)cn2n1 ; Cl]

To a stirred solution of Intermediate Example IntP08.03 (337 mg) in dichloromethane (4.0 mL) and methanol (0.4 mL) was added a solution of hydrochloric acid in dioxane (1.3 mL; c=4.0 M). The mixture was stirred at room temperature for 20 minutes. The solvent was removed in vacuum. The solid residue was triturated with dichloromethane for three times, the solvent was removed each time and the solid was dried in vacuum to give 309 mg of the title compound.

$^1$H-NMR (300 MHz, DMSO-$d_6$), δ [ppm]=0.77-1.01 (6H), 1.41 (3H), 1.43-1.51 (3H), 2.03-2.24 (1H), 3.31 (3H), 3.84-4.03 (5H), 6.81-7.00 (1H), 7.10-7.20 (2H), 7.39-7.48 (2H), 7.55 (2H), 7.63 (1H), 7.68-7.82 (5H), 8.01 (1H), 8.54 (3H), 9.19 (1H), 10.42 (1H).

Example 3.2

(1RS)-1-({[6-(4-{[(2R)-2-(4-fluorophenyl)pro-
panoyl]amino}phenyl)[1,2,4]triazolo[1,5-α]pyridin-
2-yl][2-methoxy-4-(methylsulfonyl)phenyl]
carbamoyl}oxy)ethyl 3-methyl-L-valinate
hydrochloride (Mixture of 2 Epimers)

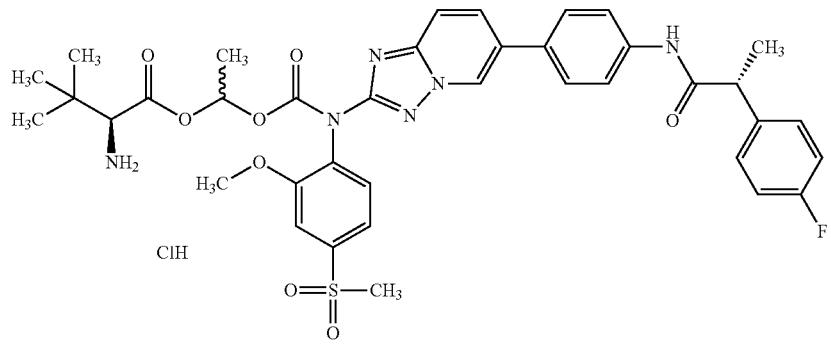 [SMILES: COc1cc(S(C)(=O)=O)ccc1N(C(=O)OC(C)OC(=O)[C@@H](N)C(C)(C)C)c1nc2ccc(-c3ccc(NC(=O)[C@H](C)c4ccc(F)cc4)cc3)cn2n1 ; Cl]

To a stirred solution of Intermediate Example IntP09.02 (39 mg) in dichloromethane (0.45 mL) and methanol (0.045 mL) was added a solution of hydrochloric acid in dioxane (0.15 mL; c=4.0 M). The mixture was stirred at room temperature for 3 h. The solvent was removed in vacuum. The solid residue was triturated with dichloromethane for three times, the solvent was removed each time and the solid was dried in vacuum to give 36 mg of the title compound.

$^1$H-NMR (400 MHz, DMSO-$d_6$), δ [ppm]=0.86-1.01 (9H), 1.41 (3H), 1.45-1.51 (3H), 3.27-3.34 (3H), 3.74-3.93 (5H), 6.82-6.98 (1H), 7.15 (2H), 7.43 (2H), 7.52-7.58 (2H), 7.63 (1H), 7.72 (4H), 7.78 (1H), 8.01 (1H), 8.42 (3H), 9.18 (1H), 10.32 (1H).

Example 3.3

(1R or 1S)-1-({[6-(4-{[(2R)-2-(4-fluorophenyl)pro-
panoyl]amino}phenyl)[1,2,4]triazolo[1,5-α]pyridin-
2-yl][2-methoxy-4-(methylsulfonyl)phenyl]
carbamoyl}oxy)ethyl-3-methyl-L-valinate
hydrochloride (Single Stereoisomer A)

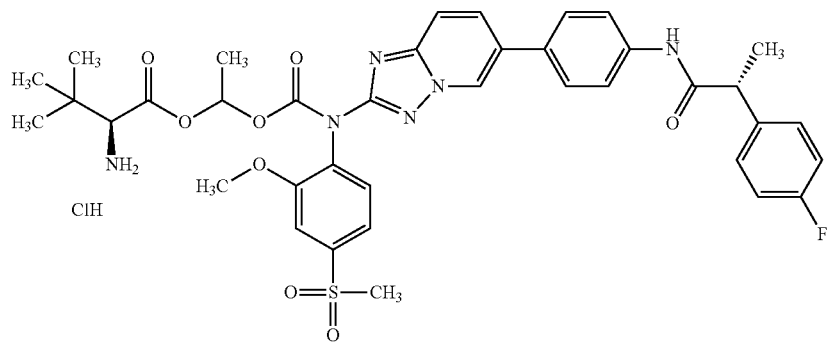 [SMILES: COc1cc(S(C)(=O)=O)ccc1N(C(=O)OC(C)OC(=O)[C@@H](N)C(C)(C)C)c1nc2ccc(-c3ccc(NC(=O)[C@H](C)c4ccc(F)cc4)cc3)cn2n1 ; Cl]

Starting with Intermediate Example IntP09.03 (2.99 g) Example 3.3. was prepared analogously to the procedure for the preparation of Example 3.2.

Yield: 2.76 g of the title compound.

$^1$H-NMR (400 MHz, DMSO-$d_6$), δ [ppm]=0.91 (9H), 1.41 (3H), 1.48 (3H), 3.30 (3H), 3.76 (1H), 3.88 (3H), 3.93 (1H), 6.81-6.91 (1H), 7.11-7.19 (2H), 7.39-7.48 (2H), 7.55 (2H), 7.63 (1H), 7.68-7.81 (5H), 8.00 (1H), 8.49 (3H), 9.18 (1H), 10.41 (1H).

Example 3.4

(1S or 1R)-1-({[6-(4-{[(2R)-2-(4-fluorophenyl)pro-
panoyl]amino}phenyl)[1,2,4]triazolo[1,5-α]pyridin-
2-yl][2-methoxy-4-(methylsulfonyl)phenyl]
carbamoyl}oxy)ethyl-3-methyl-L-valinate
hydrochloride (Single Stereoisomer B)

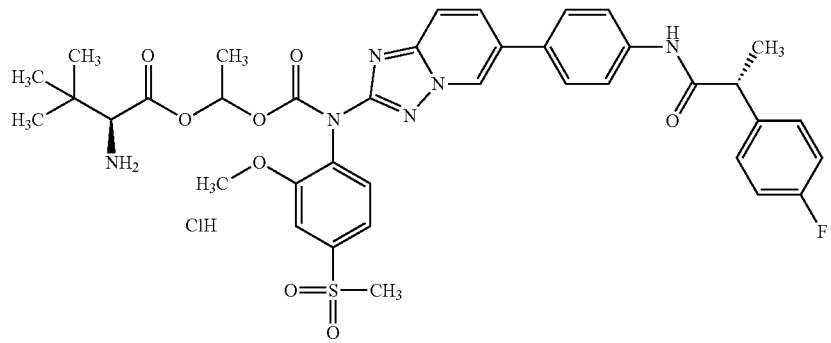 [SMILES: COc1cc(S(C)(=O)=O)ccc1N(C(=O)OC(C)OC(=O)[C@@H](N)C(C)(C)C)c1nc2ccc(-c3ccc(NC(=O)[C@H](C)c4ccc(F)cc4)cc3)cn2n1 ; Cl]

Starting with Intermediate Example IntP09.04 (3.38 g) Example 3.4. was prepared analogously to the procedure for the preparation of Example 3.2.

Yield: 3.13 g of the title compound.

$^1$H-NMR (400 MHz, DMSO-$d_6$), δ [ppm]=0.96 (9H), 1.41 (3H), 1.48 (3H), 3.31 (3H), 3.80 (1H), 3.85-3.98 (4H), 6.87-6.96 (1H), 7.09-7.19 (2H), 7.40-7.48 (2H), 7.52-7.60 (2H), 7.63 (1H), 7.67-7.81 (5H), 8.00 (1H), 8.53 (3H), 9.14-9.23 (1H), 10.42 (1H).

Example 3.5

(1RS)-1-({[6-(4-{[(2R)-2-(4-fluorophenyl)pro-
panoyl]amino}phenyl)[1,2,4]triazolo[1,5-α]pyridin-
2-yl][2-methoxy-4-(methylsulfonyl)phenyl]
carbamoyl}oxy)ethyl-L-isoleucinate hydrochloride
(Mixture of 2 Epimers)

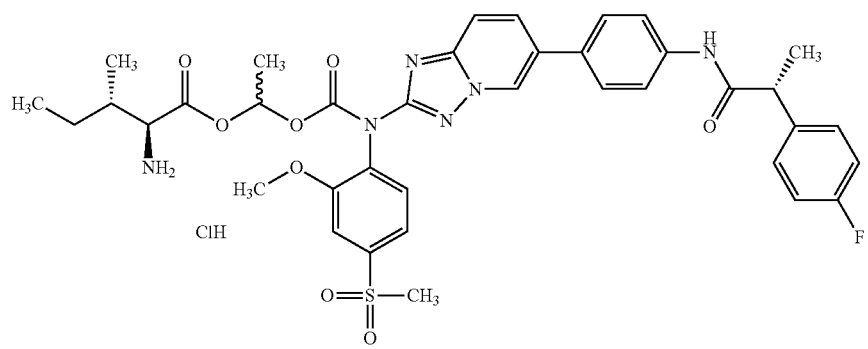 [SMILES: CC[C@H](C)[C@H](N)C(=O)OC(C)OC(=O)N(c1nc2ccc(-c3ccc(NC(=O)[C@H](C)c4ccc(F)cc4)cc3)cn2n1)c1ccc(S(C)(=O)=O)cc1OC ; Cl]

Starting with Intermediate Example IntP15.03 (100 mg) Example 3.5. was prepared analogously to the procedure for the preparation of Example 3.2.

Yield: 55 mg of the title compound.

$^1$H-NMR (400 MHz, DMSO-$d_6$), δ [ppm]=0.79 (3H), 0.85-0.93 (3H), 1.08-1.31 (2H), 1.39-1.51 (6H), 1.77-1.94 (1H), 3.33 (3H), 3.85-3.96 (4H), 3.98-4.10 (1H), 6.85-7.00 (1H), 7.12-7.21 (2H), 7.40-7.49 (2H), 7.53-7.60 (2H), 7.65 (1H), 7.74 (4H), 7.77-7.83 (1H), 8.03 (1H), 8.39-8.59 (3H), 9.20 (1H), 10.37 (1H).

Example 3.6

(1S or 1R)-1-({[6-(4-{[(2R)-2-(4-fluorophenyl)pro-
panoyl]amino}phenyl)[1,2,4]triazolo[1,5-α]pyridin-
2-yl][2-methoxy-4-(methylsulfonyl)phenyl]
carbamoyl}oxy)ethyl-isoleucinate hydrochloride
(Single Stereoisomer B)

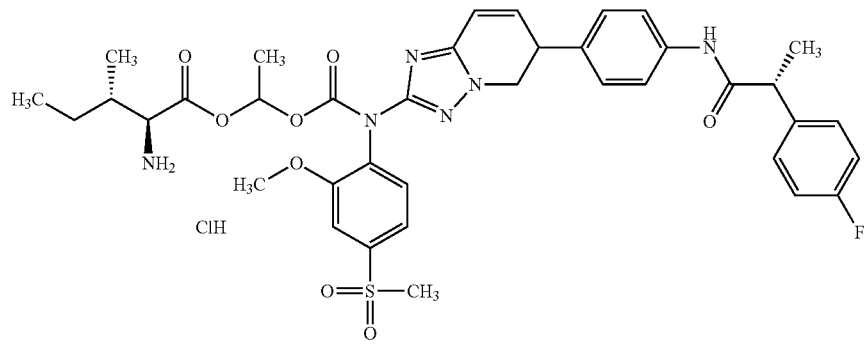 [SMILES: CC[C@H](C)[C@H](N)C(=O)OC(C)OC(=O)N(c1nc2n(n1)CC(c1ccc(NC(=O)[C@H](C)c3ccc(F)cc3)cc1)C=C2)c1ccc(S(C)(=O)=O)cc1OC ; Cl]

Starting with Intermediate Example IntP15.04 (205 mg) Example 3.6. was prepared analogously to the procedure for the preparation of Example 3.2.

Yield: 145 mg of the title compound.

$^1$H-NMR (300 MHz, DMSO-$d_6$, detected signals), δ [ppm]=0.77 (6H), 1.01-1.53 (8H), 1.83 (1H), 3.31 (3H), 3.86-3.94 (4H), 6.82-6.92 (1H), 7.10-7.21 (2H), 7.38-7.48 (2H), 7.51-7.59 (2H), 7.63 (1H), 7.68-7.82 (5H), 8.01 (1H), 8.50 (3H), 9.19 (1H), 10.39 (1H).

Example 3.7

(1R or 1S)-1-({[6-(4-{[(2R)-2-(4-fluorophenyl)pro-
panoyl]amino}phenyl)[1,2,4]triazolo[1,5-α]pyridin-
2-yl][2-methoxy-4-(methylsulfonyl)phenyl]
carbamoyl}oxy)ethyl-L-isoleucinate hydrochloride
(Single Stereoisomer A)

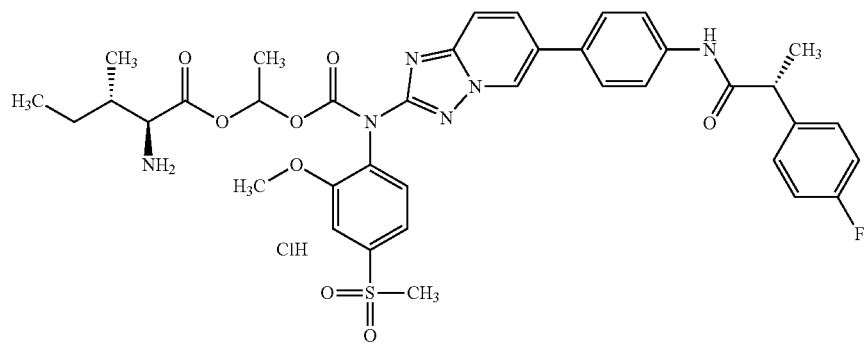 [SMILES: CC[C@H](C)[C@H](N)C(=O)OC(C)OC(=O)N(c1nc2ccc(-c3ccc(NC(=O)[C@H](C)c4ccc(F)cc4)cc3)cn2n1)c1ccc(S(C)(=O)=O)cc1OC ; Cl]

Starting with Intermediate Example IntP15.05 (230 mg) Example 3.7. was prepared analogously to the procedure for the preparation of Example 3.2.

Yield: 155 mg of the title compound.

$^1$H-NMR (300 MHz, DMSO-$d_6$), δ [ppm]=0.80-0.93 (6H), 1.17-1.50 (8H), 1.90 (1H), 3.32 (3H), 3.85-3.95 (4H), 4.05 (1H), 6.94 (1H), 7.15 (2H), 7.38-7.47 (2H), 7.56 (2H), 7.64 (1H), 7.72 (4H), 7.79 (1H), 8.01 (1H), 8.50 (3H), 9.19 (1H), 10.36 (1H).

Example 4.1

N-[6-(4-{[(2R)-2-(4-fluorophenyl)propanoyl]amino}phenyl)[1,2,4]triazolo[1,5-α]pyridin-2-yl]-N-[2-methoxy-4-(methylsulfonyl)phenyl]-4-(methylamino)butanamide trifluoroacetate

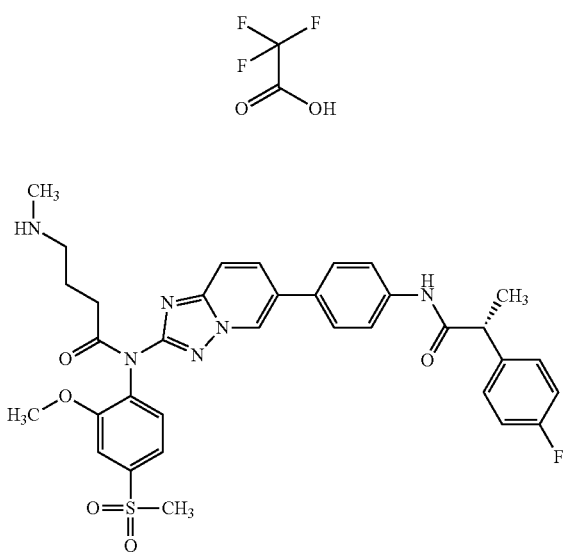 [SMILES: O=C(O)C(F)(F)F ; CNCCCC(=O)N(c1nc2ccc(-c3ccc(NC(=O)[C@H](C)c4ccc(F)cc4)cc3)cn2n1)c1ccc(S(C)(=O)=O)cc1OC]

400 mg (0.715 mmol) of (2R)-2-(4-fluorophenyl)-N-[4-(2-{[2-methoxy-4-(methylsulfonyl)phenyl]amino}[1,2,4]triazolo[1,5-α]pyridin-6-yl)phenyl]propanamide (see compound A1) and 4156 mg (8.58 mmol) 4-{[(benzyloxy)carbonyl](methyl)amino}butanoic anhydride were dissolved in 35 ml pyridine and 12 mg (0.071 mmol) DMAP were added. In 2 portions the mixture was heated in the microwave to 85° C. for 18 h. Both portions were unified and another 20 mg of DMAP were added and the mixture was stirred for additional 20 h at 90° C. The mixture was concentrated in vacuo and the remaining residue was dissolved in 300 ml dichloromethane. It was washed twice with 50 ml of 5% citric acid each, dried upon magnesium sulfate and concentrated in vacuo. The remaining residue was washed twice with 100 ml diethyl ether and dried in vacuo. 50 ml trifluoro acetic acid were added and the mixture was treated in ultrasonic equipment for 18 h. Trifluoro acetic acid was removed in vacuo and the remaining residue was washed twice with 100 ml diethyl ether and subsequently purified by HPLC (Reprosil C18-10/250-30 (Flow 16 ml/min; solvent A: water (0, 1% TFA); solvent B: acetonitrile). Relevant fractions were collected, 10 ml DMF were added and subsequently the solvents were removed in vacuo. The remaining residue was washed twice with 100 ml diethyl ether and dried in vacuo.

Yield: 273 mg (49%)

LC-MS (method 1): $R_t$=0.82 min; m/z=659 (M+H)$^+$.

$^1$H-NMR (400 MHz, DMSO-d$_6$), δ [ppm]=1.45 (3H), 1.95 (2H), 2.6 (3H), 2.95 (4H), 3.3 (3H), 3.85 (3H), 3.9 (1H), 7.15 (2H), 7.43 (2H), 7.58 (2H), 7.62 (1H), 7.72 (4H), 7.81 (1H), 8.02 (1H), 8.35 (2H), 9.2 (1H), 10.25 (1H).

Example 4.1.1

N-[6-(4-{[(2R)-2-(4-fluorophenyl)propanoyl]amino}phenyl)[1,2,4]triazolo[1,5-α]pyridin-2-yl]-N-[2-methoxy-4-(methylsulfonyl)phenyl]-4-(methylamino)butanamide hydrochloride

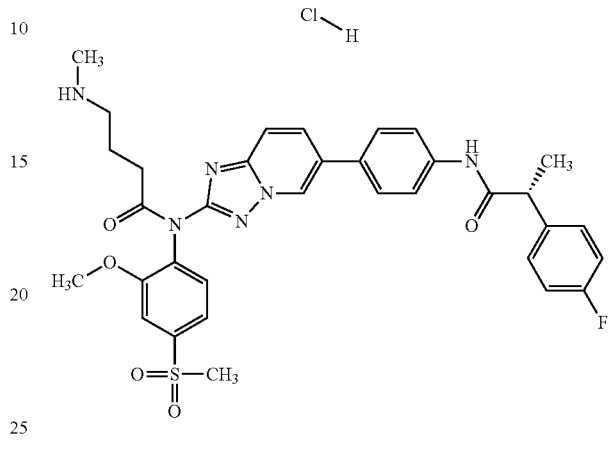

273 mg (0.353 mmol) of N-[6-(4-{[(2R)-2-(4-fluorophenyl)propanoyl]amino}phenyl)[1,2,4]triazolo[1,5-α]pyridin-2-yl]-N-[2-methoxy-4-(methylsulfonyl)phenyl]-4-(methylamino)butanamide trifluoroacetate were dissolved in 100 ml of a 0.1 M aqueous HCl solution and the solution was lyophilized. The procedure was repeated with another 100 ml of 0.1 M aqueous HCl solution. The remaining residue was solved in 100 ml of a mixture of acetonitrile and water and again lyophilized. 192 mg (78%) of the target compound were obtained as a white powder.

LC-MS (method 1): $R_t$=0.8 min; m/z=659 (M+H)$^+$.

$^1$H-NMR (400 MHz, DMSO-d$_6$), δ [ppm]=1.43 (3H), 1.95 (2H), 2.95 (4H), 3.3 (3H), 3.85 (3H), 3.9 (1H), 7.15 (2H), 7.43 (2H), 7.55 (2H), 7.62 (1H), 7.72 (4H), 7.81 (1H), 8.02 (1H), 8.5 (2H), 9.2 (1H), 10.3 (1H).

Reference Example R4.2

4-amino-N-[6-(4-{[(2R)-2-(4-fluorophenyl)propanoyl]amino}phenyl)[1,2,4]triazolo[1,5-α]pyridin-2-yl]-N-[2-methoxy-4-(methylsulfonyl)phenyl]butanamide trifluoroacetate

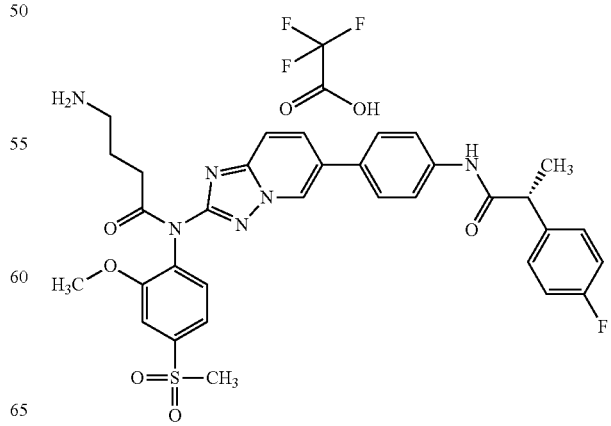

Step a) Benzyl (4-{[6-(4-{[(2R)-2-(4-fluorophenyl) propanoyl]amino}phenyl)[1,2,4]triazolo[1,5-c]pyridin-2-yl][2-methoxy-4-(methylsulfonyl)phenyl] amino}-4-oxobutyl)(4-methoxybenzyl)carbamate 210 mg (0.38 mmol) of (2R)-2-(4-fluorophenyl)-N-[4-(2-{[2-methoxy-4-(methylsulfonyl)phenyl]amino}[1,2,4]triazolo[1,5-α]pyridin-6-yl)phenyl]propanamide and 2615 mg (3.75 mmol) 5-{[(benzyloxy)carbonyl](4-methoxybenzyl) amino}butanoic anhydride were dissolved in 13 ml pyridine and 6.4 mg (0.04 mmol) DMAP were added. The mixture was heated in the microwave to 80° C. for 5 h. Another 60 mg of (2R)-2-(4-fluorophenyl)-N-[4-(2-{[2-methoxy-4-(methylsulfonyl)phenyl]amino}[1,2,4]triazolo[1,5-α]pyridin-6-yl)phenyl]propanamide, 1922 mg of 5-{[(benzyloxy)carbonyl](4-methoxybenzyl)amino}butanoic anhydride and 5 mg of DMAP were added and the mixture was heated in the microwave to 85° C. for 12 h. The mixture was concentrated in vacuo and the remaining residue was dissolved in 300 ml dichloromethane. It was washed twice with 50 ml of 5% citric acid each, dried upon magnesium sulfate and concentrated in vacuo. The remaining residue was washed twice with 50 ml diethyl ether and dried in vacuo. After purification by HPLC (Chromatorex C18-10/125-40 (Flow 16 ml/min; solvent A: water (0, 1% TFA); solvent B: acetonitrile) and drying in high vacuum 61 mg (10%) of the protected intermediate of the target compound was obtained.

LC-MS (method 1): $R_t$=1.31 min; m/z=899 (M+H)$^+$.

Step b) 4-amino-N-[6-(4-{[(2R)-2-(4-fluorophenyl) propanoyl]amino}phenyl)[1,2,4]triazolo[1,5-α]pyridin-2-yl]-N-[2-methoxy-4-(methylsulfonyl)phenyl] butanamide trifluoroacetate 35 mg (0.039 mmol) of the product obtained in step a) were dissolved in 7 ml trifluoro acetic acid and the mixture was treated in ultrasonic equipment for 6 h. Trifluoro acetic acid was removed in vacuo and the remaining residue purified by HPLC (Chromatorex C18-10/125-40 (Flow 16 ml/min; solvent A: water (0.1% TFA); solvent B: acetonitrile). Relevant fractions were collected and the solvents were removed in vacuo. The remaining residue was lyophilized from a 1:1 mixture of acetonitrile and water and 23 mg (77%) of a white powder were obtained.

LC-MS (method 1): $R_t$=0.81 min; m/z=645 (M+H)$^+$.

Reference Example R4.2.1

4-amino-N-[6-(4-{[(2R)-2-(4-fluorophenyl)propanoyl]amino}phenyl)[1,2,4]triazolo[1,5-α]pyridin-2-yl]-N-[2-methoxy-4-(methylsulfonyl)phenyl]butanamide hydrochloride

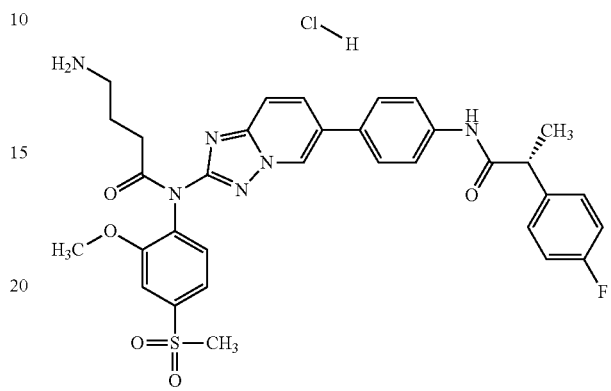

22 mg (0.024 mmol) of 4-amino-N-[6-(4-{[(2R)-2-(4-fluorophenyl) propanoyl]amino}phenyl)[1,2,4]triazolo[1,5-α]pyridin-2-yl]-N-[2-methoxy-4-(methylsulfonyl)phenyl] butanamide trifluoroacetate were dissolved in 2 ml of a 0.1 M aqueous HCl solution and the solution was lyophilized. The procedure was repeated with another 2 ml of 0.1 M aqueous HCl solution. The remaining residue was dissolved in 5 ml of a mixture of acetonitrile and water and again lyophilized. 17 mg (99%) of the target compound were obtained as a white powder.

LC-MS (method 1): $R_t$=0.81 min; m/z=645 (M+H)$^+$.
$^1$H-NMR (400 MHz, DMSO-d$_6$), δ [ppm]=1.42 (3H), 1.92 (2H), 2.87 (2H), 2.95 (2H), 3.3 (3H), 3.85 (3H), 3.9 (1H), 7.15 (2H), 7.45 (2H), 7.58 (2H), 7.62 (1H), 7.72 (4H), 7.81 (4H), 8.02 (1H), 9.2 (1H), 10.25 (1H).

Example 5.1

(1RS)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl] carbamoyl}oxy)-2-methylpropyl 3-methyl-L-valinate hydrochloride (Mixture of 2 Epimers)

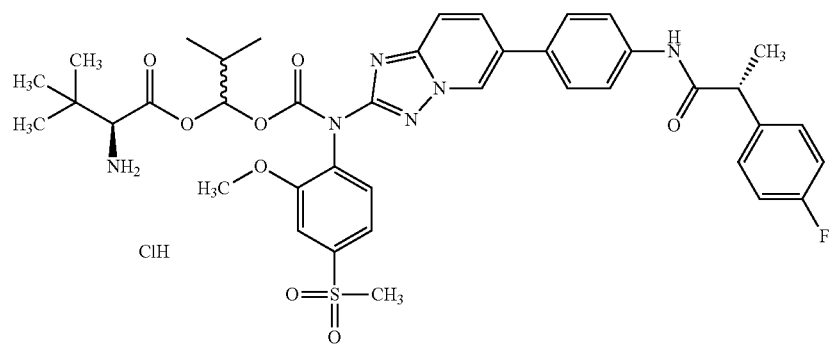

To a stirred solution of Intermediate Example IntP19.03 (250 mg) in dichloromethane (2.80 mL) and methanol (0.28 mL) was added a solution of hydrochloric acid in dioxane (0.94 mL; c=4.0 M). The mixture was stirred at room temperature for 30 minutes. The solvent was removed in vacuum. The solid residue was triturated with dichloromethane for three times, the solvent was removed each time and the solid was dried in vacuum to give 230 mg of the title compound.

$^1$H-NMR (400 MHz, DMSO-d$_6$), δ [ppm]=0.80-1.00 (15H), 1.41 (3H), 2.02 (1H), 3.30 (3H), 3.74-3.98 (5H), 6.63-6.72 (1H), 7.15 (2H), 7.43 (2H), 7.55 (1H), 7.57 (1H), 7.64 (1H), 7.72 (4H), 7.78 (1H), 8.01 (1H), 8.49 (3H), 9.18 (1H), 10.38 (1H).

Example 5.2

(1R or S)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)-2-methylpropyl-L-valinate hydrochloride (Single Stereoisomer A)

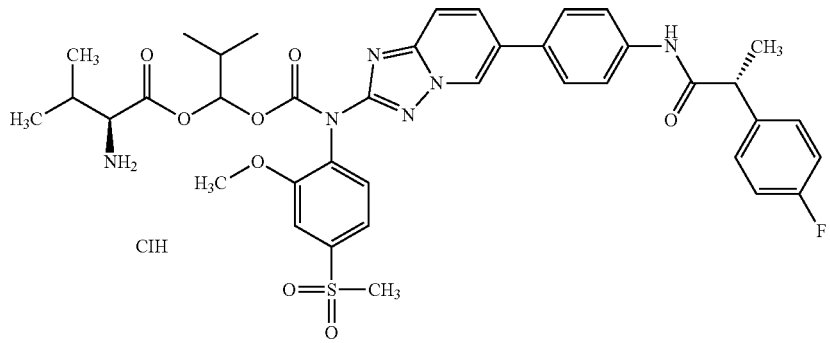 [SMILES: COc1cc(S(C)(=O)=O)ccc1N(C(=O)OC(OC(=O)[C@@H](N)C(C)C)C(C)C)c1nc2ccc(-c3ccc(NC(=O)[C@H](C)c4ccc(F)cc4)cc3)cn2n1 ; "CIH"]

To a stirred solution of Intermediate Example IntP20.03 (100 mg) in dichloromethane (2.00 mL) and methanol (0.17 mL) was added a solution of hydrochloric acid in dioxane (0.38 mL; c=4.0 M). The mixture was stirred at room temperature for 90 minutes. The solvent was removed in vacuum. The solid residue was triturated with dichloromethane for three times, the solvent was removed each time and the solid was dried in vacuum to give 90 mg of the title compound.

$^1$H-NMR (400 MHz, DMSO-d$_6$), δ [ppm]=0.75-1.00 (12H), 1.41 (3H), 1.99 (1H), 2.13 (1H), 3.30 (3H), 3.84-3.94 (4H), 4.01 (1H), 6.66 (1H), 7.15 (2H), 7.43 (2H), 7.55 (2H), 7.64 (1H), 7.72 (4H), 7.77 (1H), 8.00 (1H), 8.48 (3H), 9.18 (1H), 10.36 (1H).

Example 5.3

(1S or R)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)-2-methylpropyl-L-valinate hydrochloride (Single Stereoisomer B)

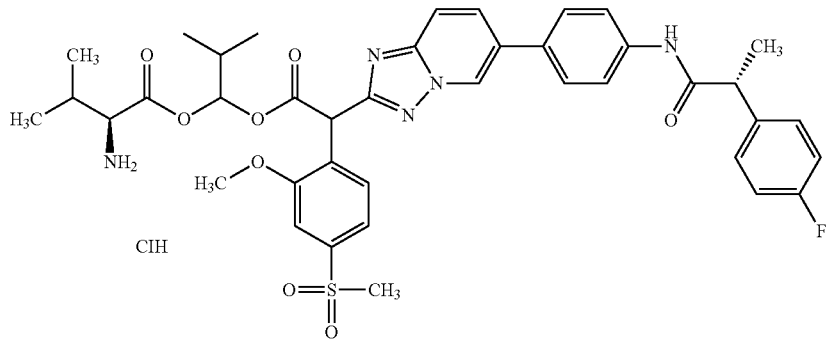 [SMILES: COc1cc(S(C)(=O)=O)ccc1C(C(=O)OC(OC(=O)[C@@H](N)C(C)C)C(C)C)c1nc2ccc(-c3ccc(NC(=O)[C@H](C)c4ccc(F)cc4)cc3)cn2n1 ; "CIH"]

To a stirred solution of Intermediate Example IntP20.04. (100 mg) in dichloromethane (2.00 mL) and methanol (0.17 mL) was added a solution of hydrochloric acid in dioxane (0.38 mL; c=4.0 M). The mixture was stirred at room temperature for 90 minutes. The solvent was removed in vacuum. The solid residue was triturated with dichloromethane for three times, the solvent was removed each time and the solid was dried in vacuum to give 93 mg of the title compound.

$^1$H-NMR (400 MHz, DMSO-$d_6$), δ [ppm]=0.75-1.00 (12H), 1.41 (3H), 1.99 (1H), 2.22 (1H), 3.31 (3H), 3.84-3.94 (4H), 4.05 (1H), 6.71 (1H), 7.15 (2H), 7.43 (2H), 7.58 (2H), 7.65 (1H), 7.72 (4H), 7.77 (1H), 8.00 (1H), 8.50 (3H), 9.18 (1H), 10.37 (1H).

Example 5.4

(1RS)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)-2-methylpropyl-L-valinate hydrochloride (Mixture of 2 Epimers)

To a stirred solution of Intermediate Example IntP20.02 (25 mg) in dichloromethane (0.28 mL) and methanol (0.03 mL) was added a solution of hydrochloric acid in dioxane (0.10 mL; c=4.0 M). The mixture was stirred at room temperature for 30 minutes. The solvent was removed in vacuum. The solid residue was triturated with dichloromethane for three times, the solvent was removed each time and the solid was dried in vacuum to give 22 mg of the title compound.

$^1$H-NMR (400 MHz, DMSO-$d_6$), δ [ppm]=0.75-1.00 (12H), 1.41 (3H), 1.99 (1H), 2.06-2.25 (1H), 3.30 (3H), 3.84-3.94 (4H), 3.99-4.07 (1H), 6.65-6.73 (1H), 7.15 (2H), 7.42 (2H), 7.55 (1H), 7.57 (1H), 7.64 (1H), 7.71 (4H), 7.77 (1H), 8.01 (1H), 8.40 (3H), 9.17 (1H), 10.28 (1H).

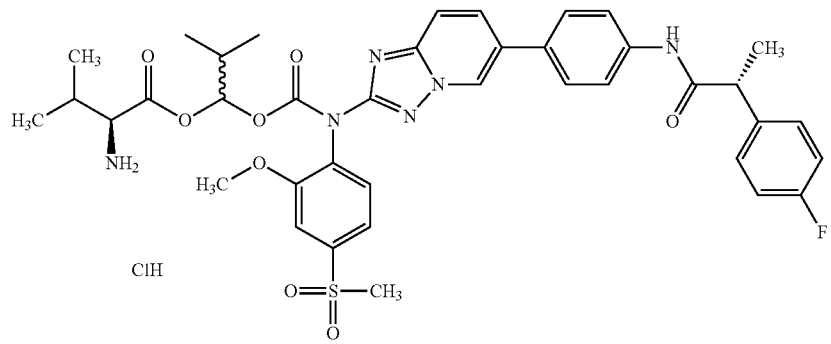 [SMILES: COc1cc(S(C)(=O)=O)ccc1N(C(=O)OC(OC(=O)[C@@H](N)C(C)C)C(C)C)c1nc2ccc(-c3ccc(NC(=O)[C@H](C)c4ccc(F)cc4)cc3)cn2n1 ; Cl]

Example 5.5

(1RS)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)-2-methylpropyl-2-methylalaninate hydrochloride (Mixture of 2 Epimers)

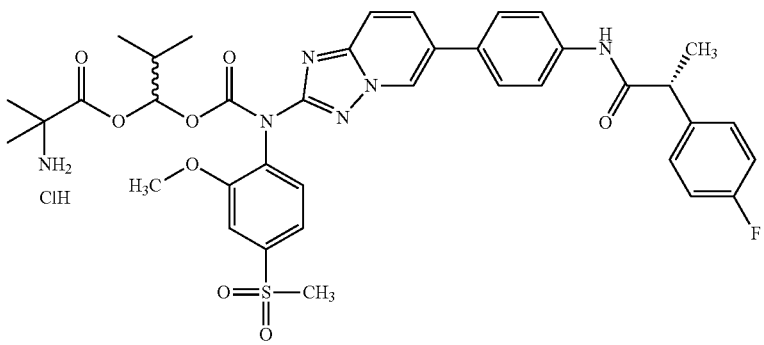 [SMILES: COc1cc(S(C)(=O)=O)ccc1N(C(=O)OC(OC(=O)C(C)(C)N)C(C)C)c1nc2ccc(-c3ccc(NC(=O)[C@H](C)c4ccc(F)cc4)cc3)cn2n1 ; Cl]

To a stirred solution of Intermediate Example IntP21.03 (30 mg) in dichloromethane (1.00 mL) and methanol (0.05 mL) was added a solution of hydrochloric acid in dioxane (0.13 mL; c=4.0 M). The mixture was stirred at room temperature for 2 hours. The solvent was removed in vacuum. The solid residue was triturated with dichloromethane for three times, the solvent was removed each time and the solid was dried in vacuum to give 14 mg of the title compound.

$^1$H-NMR (400 MHz, DMSO-$d_6$), δ [ppm]=0.82 (6H), 1.40 (3H), 1.49 (6H), 1.95 (1H), 3.31 (3H), 3.82-3.96 (4H), 6.60 (1H), 7.15 (2H), 7.43 (2H), 7.57 (2H), 7.65 (1H), 7.72 (4H), 7.77 (1H), 8.00 (1H), 8.70 (3H), 9.18 (1H), 10.38 (1H).

Example 6.1

({[6-(4-{[(2R)-2-(4-fluorophenyl)propanoyl]amino}phenyl)[1,2,4]triazolo[1,5-α]pyridin-2-yl][4-(methylsulfonyl)-2-(2,2,2-trifluoroethoxy)phenyl]carbamoyl}oxy)methyl 3-methyl-L-valinate hydrochloride

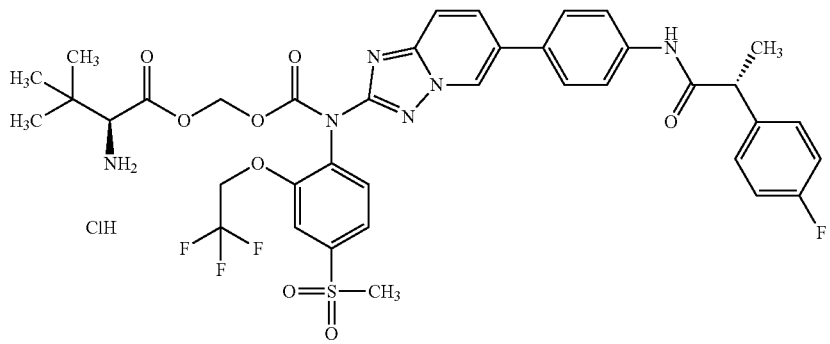 [SMILES: C[C@@H](C(=O)Nc1ccc(-c2ccc3nc(N(C(=O)OCOC(=O)[C@@H](N)C(C)(C)C)c4ccc(S(C)(=O)=O)cc4OCC(F)(F)F)nn3c2)cc1)c1ccc(F)cc1 ; Cl]

Starting with Intermediate Example IntP16.03. (80 mg) Example 6.1. was prepared analogously to the procedure for the preparation of Example 1.5.

Yield: 25 mg of the title compound.

$^1$H-NMR (400 MHz, DMSO-$d_6$), δ [ppm]=0.97 (9H), 1.41 (3H), 3.83-3.94 (2H), 4.92 (2H), 5.87 (1H), 5.96 (1H), 7.10-7.19 (2H), 7.39-7.46 (2H), 7.64-7.83 (8H), 8.01 (1H), 8.41 (3H), 9.18 (1H), 10.29 (1H).

Example 6.2

({[6-(4-{[(2R)-2-(4-fluorophenyl)propanoyl]amino}phenyl)[1,2,4]triazolo[1,5-α]pyridin-2-yl][4-(methylsulfonyl)-2-(2,2,2-trifluoroethoxy)phenyl]carbamoyl}oxy)methyl L-valinate hydrochloride

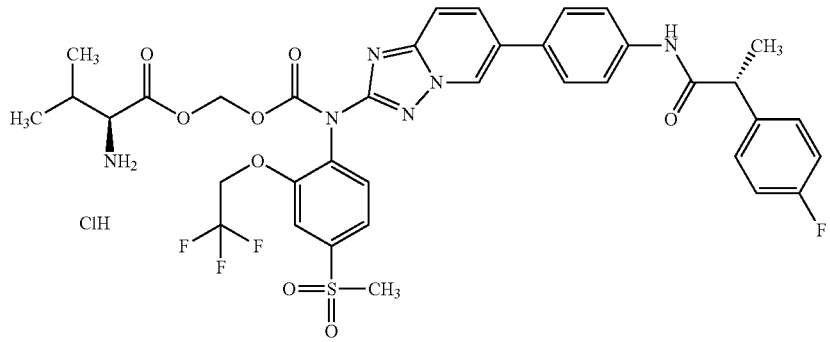

Starting with Intermediate Example IntP17.02. (140 mg) Example 6.2. was prepared analogously to the procedure for the preparation of Example 1.5.

Yield: 50 mg of the title compound.

$^1$H-NMR (400 MHz, DMSO-$d_6$), δ [ppm]=0.93 (6H), 1.41 (3H), 2.18 (1H), 3.32 (3H), 3.91 (1H), 3.98-4.05 (1H), 4.93 (2H), 5.86 (1H), 5.96 (1H), 7.10-7.20 (2H), 7.39-7.47 (2H), 7.66-7.68 (2H), 7.70-7.74 (4H), 7.77 (1H), 7.81 (1H), 8.01 (1H), 8.52 (3H), 9.19 (1H), 10.36 (1H).

Example 6.3

[({4-[(3-fluoroazetidin-1-yl)carbonyl]-2-(2,2,2-trifluoroethoxy)phenyl}[6-(4-{[(2R)-2-(4-fluorophenyl)propanoyl]amino}phenyl)[1,2,4]triazolo[1,5-α]pyridin-2-yl]carbamoyl)oxy]methyl 3-methyl-L-valinate hydrochloride

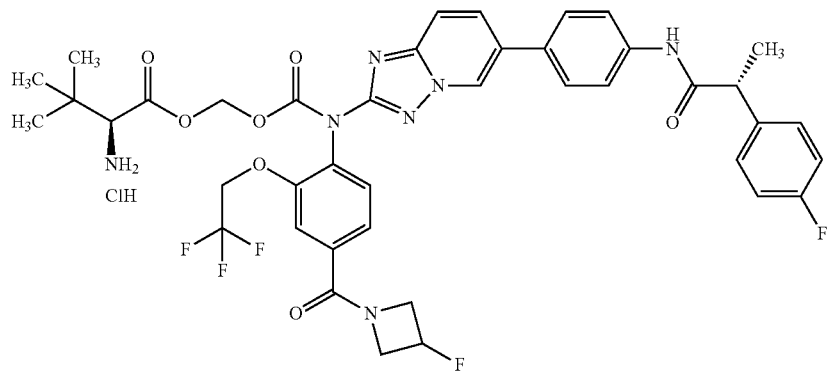 [SMILES: C[C@@H](C(=O)Nc1ccc(-c2ccc3nc(N(C(=O)OCOC(=O)[C@@H](N)C(C)(C)C)c4ccc(C(=O)N5CC(F)C5)cc4OCC(F)(F)F)nn3c2)cc1)c1ccc(F)cc1 ; Cl]

Starting with Intermediate Example IntP18.03 (160 mg) Example 6.3. was prepared analogously to the procedure for the preparation of Example 1.5.

Yield: 130 mg of the title compound.

$^1$H-NMR (300 MHz, DMSO-$d_6$), δ [ppm]=0.92-1.03 (9H), 1.37-1.44 (3H), 3.81-3.96 (2H), 3.97-4.24 (1H), 4.25-4.70 (3H), 4.83 (2H), 5.28-5.62 (1H), 5.85 (1H), 5.95 (1H), 7.08-7.22 (2H), 7.33-7.51 (5H), 7.67-7.82 (5H), 8.01 (1H), 8.47 (3H), 9.18 (1H), 10.38 (1H).

Example 7.1

2-(methylamino)ethyl [6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamate hydrochloride

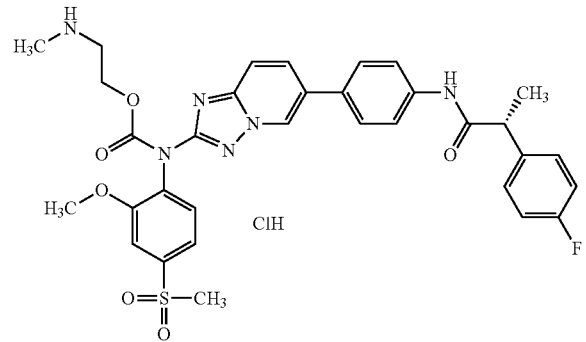 [SMILES: CNCCOC(=O)N(c1nc2ccc(-c3ccc(NC(=O)[C@H](C)c4ccc(F)cc4)cc3)cn2n1)c1ccc(S(C)(=O)=O)cc1OC ; Cl]

Starting with Intermediate Example IntP22.04. (25 mg) Example 7.1. was prepared analogously to the procedure for the preparation of Example 1.5.

Yield: 25 mg of the title compound.

$^1$H-NMR (300 MHz, DMSO-$d_6$, detected signals), δ [ppm]=1.41 (3H), 3.13-3.26 (2H), 3.32 (3H), 3.86 (3H), 3.89-3.98 (1H), 4.46 (2H), 7.15 (2H), 7.44 (2H), 7.53-7.67 (3H), 7.68-7.83 (5H), 8.01 (1H), 8.99 (2H), 9.19 (1H), 10.44 (1H).

Example 8.1

(2R)-2-(4-fluorophenyl)-N-[4-(2-{[2-methoxy-4-(methylsulfonyl)phenyl](N-methylglycyl)amino}[1,2,4]triazolo[1,5-α]pyridin-6-yl)phenyl]propanamide trifluoroacetate

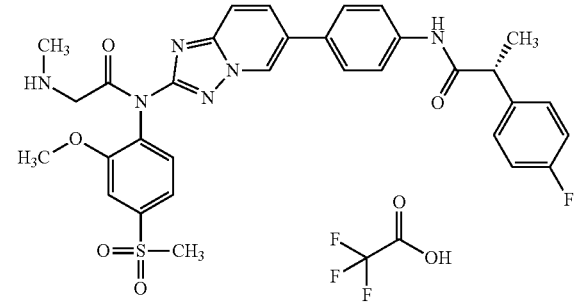 [SMILES: CNCC(=O)N(c1nc2ccc(-c3ccc(NC(=O)[C@H](C)c4ccc(F)cc4)cc3)cn2n1)c1ccc(S(C)(=O)=O)cc1OC ; O=C(O)C(F)(F)F]

To a stirred solution of Intermediate Example IntP23.03 (500 mg) in dichloromethane (20 mL) was added trifluoroacetic acid (2.6 mL). The mixture was stirred at room temperature for 2 h. The solvent was removed in vacuum. Silicagel chromatography followed by preparative reverse phase HPLC (gradient of water and acetonitrile containing trifluoroacetic acid as additive) gave 110 mg of the title compound after lyophilisation.

$^1$H-NMR (300 MHz, DMSO-d$_6$), δ [ppm]=1.41 (3H), 2.64 (3H), 3.35 (3H), 3.79-3.91 (4H), 4.64 (2H), 7.11-7.20 (2H), 7.42 (3H), 7.61-7.76 (7H), 7.85 (1H), 8.07 (1H), 8.93 (2H), 9.22 (1H), 10.24 (1H).

Solubility

The solubility of compound A1 at 25° C. in different solvents is shown in Table 1:

TABLE 1

Solubility of compound A1 at 25° C.

| solvent | dissolved amount in mg/100 mL solution |
|---|---|
| water | <0.1 |
| aqueous solution, phopshate buffer pH 8 | <0.1 |
| aqueous solution, phopshate buffer pH 7 | <0.1 |
| aqueous solution, acetate buffer pH 4.5 | <0.1 |
| 0.1M HCl in water | <0.1 |
| ethanol | 45.7 |
| acetonitrile | 350.2 |
| acetone | 1518.3 |

Biological Assay: Proliferation Assay

Cultivated tumor cells (MCF7, hormone dependent human mammary carcinoma cells, ATCC HTB22; NCI-H460, human non-small cell lung carcinoma cells, ATCC HTB-177; DU 145, hormone-independent human prostate carcinoma cells, ATCC HTB-81; HeLa-MaTu, human cervical carcinoma cells, EPO-GmbH, Berlin; HeLa-MaTu-ADR, multidrug-resistant human cervical carcinoma cells, EPO-GmbH, Berlin; HeLa human cervical tumor cells, ATCC CCL-2; B16F10 mouse melanoma cells, ATCC CRL-6475) were plated at a density of 5000 cells/well (MCF7, DU145, HeLa-MaTu-ADR), 3000 cells/well (NCI-H460, HeLa-MaTu, HeLa), or 1000 cells/well (B16F10) in a 96-well multititer plate in 200 μl of their respective growth medium supplemented 10% fetal calf serum. After 24 hours, the cells of one plate (zero-point plate) were stained with crystal violet (see below), while the medium of the other plates was replaced by fresh culture medium (200 μl), to which the test substances were added in various concentrations (0 μM, as well as in the range of 0.01-30 μM; the final concentration of the solvent dimethyl sulfoxide was 0.5%). The cells were incubated for 4 days in the presence of test substances. Cell proliferation was determined by staining the cells with crystal violet: the cells were fixed by adding 20 μl/measuring point of an 11% glutaric aldehyde solution for 15 minutes at room temperature. After three washing cycles of the fixed cells with water, the plates were dried at room temperature. The cells were stained by adding 100 μl/measuring point of a 0.1% crystal violet solution (pH 3.0). After three washing cycles of the stained cells with water, the plates were dried at room temperature. The dye was dissolved by adding 100 μl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 μm) cells (=100%). The IC$_{50}$ values were determined by means of a 4 parameter fit. The compounds A1, A2, A3, A4 and A5 are characterized by an IC$_{50}$ determined in a HeLa-MaTu-ADR cell proliferation assay (as described above) that is lower than 10 μM. The IC$_{50}$ of preferred compounds is even lower than 2.0 μM. The IC$_{50}$ of more preferred compounds is even lower than 500 nM. The IC$_{50}$ of even more preferred compounds is even lower than 250 nM. The IC$_{50}$ of most preferred compounds is even lower than 200 nM.

The compounds A1, A2, A3, A4 and A5 are characterized by the following IC$_{50}$ values, determined in a HeLa cell proliferation assay (as described above):

| Compound | Inhibition of cell proliferation, cell Line: HeLa IC$_{50}$ |
|---|---|
| A1 | <400 nM |
| A2 | <200 nM |
| A3 | <100 nM |
| A4 | <100 nM |
| A5 | <100 nM |

Mps-1 Kinase Assay

The human kinase Mps-1 phosphorylates a biotinylated substrate peptide. Detection of the phosphorylated product is achieved by time-resolved fluorescence resonance energy transfer (TR-FRET) from Europium-labelled anti-phospho-Serine/Threonine antibody as donor to streptavidin labelled with cross-linked allophycocyanin (SA-XLent) as acceptor. Compounds are tested for their inhibition of the kinase activity.

N-terminally GST-tagged human full length recombinant Mps-1 kinase (purchased from Invitrogen, Karslruhe, Germany, cat. no PV4071) was used. As substrate for the kinase reaction a biotinylated peptide of the amino-acid sequence PWDPDDADITEILG (SEQ ID: 1) (C-terminus in amide form, purchased from Biosynthan GmbH, Berlin) was used.

For the assay 50 nl of a 100-fold concentrated solution of the test compound in DMSO was pipetted into a black low volume 384 well microtiter plate (Greiner Bio-One, Frickenhausen, Germany), 2 μl of a solution of Mps-1 in assay buffer [0.1 mM sodium-ortho-vanadate, 10 mM MgCl$_2$, 2 mM DTT, 25 mM Hepes pH 7.7, 0.05% BSA, 0.001% Pluronic F-127] were added and the mixture was incubated for 15 min at 22° C. to allow pre-binding of the test compounds to Mps-1 before the start of the kinase reaction. Then the kinase reaction was started by the addition of 3 μl of a solution of 16.7 adenosine-tri-phosphate (ATP, 16.7 μM=>final conc. in the 5 μl assay volume is 10 μM) and peptide substrate (1.67 μM=>final conc. in the 5 μl assay volume is 1 μM) in assay buffer and the resulting mixture was incubated for a reaction time of 60 min at 22° C. The concentration of Mps-1 in the assay was adjusted to the activity of the enzyme lot and was chosen appropriate to have the assay in the linear range, typical enzyme concentrations were in the range of about 1 nM (final conc. in the 5 μl assay volume). The reaction was stopped by the addition of 3 μl of a solution of HTRF detection reagents (100 mM Hepes pH 7.4, 0.1% BSA, 40 mM EDTA, 140 nM Streptavidin-XLent [# 61GSTXLB, Fa. Cis Biointernational, Marcoule, France], 1.5 nM anti-phospho(Ser/Thr)-Europium-antibody [#AD0180, PerkinElmer LAS, Rodgau-Jügesheinn, Germany].

The resulting mixture was incubated 1 h at 22° C. to allow the binding of the phosphorylated peptide to the anti-phospho(Ser/Thr)-Europium-antibody. Subsequently the amount of phosphorylated substrate was evaluated by measurement of the resonance energy transfer from the Europium-labelled anti-phospho(Ser/Thr) antibody to the Streptavidin-XLent. Therefore, the fluorescence emissions at 620 nm and 665 nm after excitation at 350 nm was measured in a Viewlux TR-FRET reader (PerkinElmer LAS, Rodgau-Jügesheinn, Germany). The "blank-corrected normalized ratio" (a Viewlux specific readout, similar to the traditional ratio of the emissions at 665 nm and at 622 nm, in which blank and Eu-donor crosstalk are subtracted from the 665 nm signal before the ratio is calculated) was taken as the measure for the amount of phosphorylated substrate. The data were normalised (enzyme reaction without inhibitor=0% inhibition, all other assay components but no enzyme=100% inhibition). Test compounds were tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit.

The compounds A1, A2, A3, A4 and A5 are characterized by the following $IC_{50}$ values, determined in Mps-1 kinase assays (as described above):

| Compound | Mps-1 Inhibition, $IC_{50}$ in M (Assay with 10 μM ATP) | Mps-1 Inhibition, $IC_{50}$ in M (Assay with 2 mM ATP) |
|---|---|---|
| A1 | <1 nM | 1.9 nM |
| A2 | <1 nM | <1 nM |
| A3 | <1 nM | <1 nM |
| A4 | <1 nM | <1 nM |
| A5 | <1 nM | <1 nM |

Spindle Assembly Checkpoint Assay

The spindle assembly checkpoint assures the proper segregation of chromosomes during mitosis. Upon entry into mitosis, chromosomes begin to condensate which is accompanied by the phosphorylation of histone H3 on serine 10. Dephosphorylation of histone H3 on serine 10 begins in anaphase and ends at early telophase. Accordingly, phosphorylation of histone H3 on serine 10 can be utilized as a marker of cells in mitosis. Nocodazole is a microtubule destabilizing substance. Thus, nocodazole interferes with microtubule dynamics and mobilises the spindle assembly checkpoint. The cells arrest in mitosis at G2/M transition and exhibit phosphorylated histone H3 on serine 10. An inhibition of the spindle assembly checkpoint by Mps-1 inhibitors overrides the mitotic blockage in the presence of nocodazole, and the cells complete mitosis prematurely. This alteration is detected by the decrease of cells with phosphorylation of histone H3 on serine 10. This decline is used as a marker to determine the capability of compounds of the present invention to induce a mitotic breakthrough.

Cultivated cells of the human cervical tumor cell line HeLa (ATCC CCL-2) were plated at a density of 2500 cells/well in a 384-well microtiter plate in 20 μl Dulbeco's Medium (w/o phenol red, w/o sodium pyruvate, w 1000 mg/ml glucose, w pyridoxine) supplemented with 1% (v/v) glutamine, 1% (v/v) penicillin, 1% (v/v) streptomycin and 10% (v/v) fetal calf serum. After incubation overnight at 37° C., 10 μl/well nocodazole at a final concentration of 0.1 μg/ml were added to cells. After 24 h incubation, cells were arrested at G2/M phase of the cell cycle progression. Test compounds solubilised in dimethyl sulfoxide (DMSO) were added at various concentrations (0 μM, as well as in the range of 0.005 μM-10 μM; the final concentration of the solvent DMSO was 0.5% (v/v)). Cells were incubated for 4 h at 37° C. in the presence of test compounds. Thereafter, cells were fixed in 4% (v/v) paraformaldehyde in phosphate buffered saline (PBS) at 4° C. overnight then permeabilised in 0.1% (v/v) Triton X™ 100 in PBS at room temperature for 20 min and blocked in 0.5% (v/v) bovine serum albumin (BSA) in PBS at room temperature for 15 min. After washing with PBS, 20 μl/well antibody solution (anti-phospho-histone H3 clone 3H10, FITC; Upstate, Cat#16-222; 1:200 dilution) was added to cells, which were incubated for 2 h at room temperature. Afterwards, cells were washed with PBS and 20 μl/well HOECHST 33342 dye solution (5 μg/ml) was added to cells and cells were incubated 12 min at room temperature in the dark. Cells were washed twice with PBS then covered with PBS and stored at 4° C. until analysis. Images were acquired with a Perkin Elmer OPERA™ High-Content Analysis reader. Images were analyzed with image analysis software MetaXpress™ from Molecular devices utilizing the Cell Cycle application module. In this assay both labels HOECHST 33342 and phosphorylated Histone H3 on serine 10 were measured. HOECHST 33342 labels DNA and is used to count cell number. The staining of phosphorylated Histone H3 on serine 10 determines the number of mitotic cells. Inhibition of Mps-1 decreases the number of mitotic cells in the presence of nocodazole indicating an inappropriate mitotic progression. The raw assay data were further analysed by four parameter logistic regression analysis to determine the $IC_{50}$ value for each tested compound.

Stability in Buffer at pH 7.4

0.3 mg of the test compound are solved in 0.1 ml dimethylsulfoxide and 0.4 ml acetonitrile. For complete dissolution the HPLC vial with the sample solution is sonified for about 20 seconds. Then 1.0 ml of the buffer solution is added, and the sample is again treated in the ultrasonic bath.

Preparation of the Buffer Solution:

90 g of sodium chloride, 13.61 g of potassium dihydrogen phosphate and 83.35 g of 1 M sodium hydroxide solution are made up to 1 liter with Millipore water and then diluted 1:10.

10 μl portions of the sample solution are analysed by HPLC to determine the amount of the test compound over a period of 24 hours at 37° C. The peak areas in percentage are used for quantification.

HPLC Method:

Agilent 1100 with DAD (G1315B), binary pump (G1312A), autosampler (G1329A), column oven (G1316A), thermostat (G1330B); column: Kromasil 100 C18, 250 mm×4 mm, 5 μm; column temperature: 37° C.; eluent A: water+5 ml of perchloric acid/liter, eluent B: acetonitrile.

Gradient:

0 min 98% A, 2% B→0-3.0 min 85% A, 15% B→3.0-8.0 min 50% A, 50% B→8.0-16.0 min 50% A, 50% B→16.0-20.0 min 10% A, 90% B→20.0-21.0 10% A, 90% B→21.0-24.0 min 98% A, 2% B→24.0-25.0 min 98% A, 2% B; flow rate: 1.5 ml/min; UV detection: 210 nm.

The ratio of the peak areas (F) at different time points in relation to the peak areas at the starting time are shown in Table 2 for representative examples:

TABLE 2

Stability in buffer at pH 7.4

| Example No. | % Test Compound after 24 h [F(t = 24 h) × 100/F(t = 0 h)] |
|---|---|
| 1.1. | 35.0 *) |
| 1.2 | 0.0 |
| 1.4 | 0.0 |
| 1.5 | 0.0 |
| 1.7 | 0.0 |
| 1.8 | 0.0 |
| 2.1 | 0.0 |
| 2.2 | 0.0 |
| 2.3 | 16 |
| 2.4 | 48 |
| 3.1 | 0.0 |
| 3.2 | 0.0 |
| 3.3 | 0.0 |
| 3.4 | 0.0 |
| 3.6 | 0.0 |
| 3.7 | 0.0 |
| 4.1 | 23 |
| 4.1.1 | 21 |
| 5.1 | 21 |
| 5.2 | 48 |
| 5.3 | 11 |
| 5.4 | 17 |
| 6.1. | 0.0 |
| 6.3. | 0.0 |
| 7.1 | 48 |

*) measured for formic acid salt

In vitro Stability in Rat and Human Plasma (HPLC Detection)

1 mg of test compound is dissolved in 1.25 ml dimethylsulfoxide. Then 1.25 ml water are added. 0.5 ml of this sample solution are mixed with 0.5 ml heparinized and 37° C. warm plasma (wistar rat plasma or human plasma). A first sample (10 µl) is immediately taken for HPLC analysis. In the period up to 4 h after the start of incubation further 10 µl aliquots are taken after 30, 60, 90, 120 and 240 minutes and the amount of the test compound is determined.

HPLC Method:

Agilent 1100 with DAD (G1315A), binary pump (G1312A), autosampler (G1329A), column oven (G1316A), thermostat (G1330B); column: Kromasil 100 C18, 250 mm×4 mm, 5 µm; column temperature: 45° C.; eluent A: water+5 ml of perchloric acid/liter, eluent B: acetonitrile.

Gradient:

0 min 98% A, 2% B→0-3.0 min 85% A, 15% B→3.0-8.0 min 55% A, 45% B→8.0-16.0 min 55% A, 45% B→16.0-20.0 min 10% A, 90% B→20.0-21.0 10% A, 90% B→21.0-24.0 min 98% A, 2% B→24.0-25.0 min 98% A, 2% B; flow rate: 1.5 ml/min; UV detection: 222 nm.

The ratio of the peak areas (F) at the respective time points in relation to the peak areas at the starting time indicates the remaining parent compound, hence indicating stability under the experimental conditions described.

TABLE 3

In vitro stability in rat plasma

| Example No. | % Test Compound after 4 h [F(t = 24 h) × 100/F(t = 0 h)] |
|---|---|
| 1.2 | 0.0 |
| 1.3 | 0.0 |
| 1.4 | 14 |
| 1.5 | 0.0 |
| 1.6 | 0.0 |
| 1.7 | 36 |
| 1.8 | 3 |
| 2.1 | 0.0 |
| 2.2 | 5 |
| 2.3 | 37 |
| 2.4 | 45 |
| 3.1 | 0.0 |
| 3.2 | 0.0 |
| 3.3 | 22 |
| 3.4 | 29 |
| 3.5 | 19 |
| 4.1 | 12 |
| 4.1.1 | 32 |
| 5.1 | 19 |
| 5.2 | 44 |
| 5.3 | 45 |
| 5.4 | 44 |
| 5.5 | 33 |
| 6.1. | 4 |
| 6.2. | 6 |
| 6.3. | 0.0 |
| 7.1 | 80 |
| 8.1 | 57 |

Determination of Metabolic Stability in vitro (Including Calculation of Hepatic in vivo Blood Clearance (CL) and of Maximal Oral Bioavailability ($F_{max}$))

The metabolic stability of test compounds in vitro was determined by incubating them at 1 µM with a suspension liver microsomes in 100 mM phosphate buffer, pH7.4 ($NaH_2PO_4 \times H_2O + Na_2HPO_4 \times 2H_2O$) at a protein concentration of 0.5 mg/mL and at 37° C. The reaction was activated by adding a co-factor mix containing 1.2 mg NADP, 3 IU glucose-6-phosphate dehydrogenase, 14.6 mg glucose-6-phosphate and 4.9 mg $MgCl_2$ in phosphate buffer, pH 7.4. Organic solvent in the incubations was limited to <0.2% dimethylsulfoxide (DMSO) and <1% methanol. During incubation, the microsomal suspensions were continuously shaken and aliquots were taken at 2, 8, 16, 30, 45 and 60 min, to which equal volumes of cold methanol were immediately added. Samples were frozen at −20° C. over night, subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, specific liver weight and microsomal protein content the hepatic in vivo blood clearance (CL) and the maximal oral bioavailability ($F_{max}$) were calculated for the different species. The following parameter values were used: Liver blood flow—1.3 L/h/kg (human), 2.1 L/h/kg (dog), 4.2 L/h/kg (rat); specific liver weight—21 g/kg (human), 39 g/kg (dog), 32 g/kg (rat); microsomal protein content—40 mg/g.

With the described assay only phase-I metabolism of microsomes is reflected, e.g. typically oxidoreductive reactions by cytochrome P450 enzymes and flavin mono-oxygenases (FMO) and hydrolytic reactions by esterases (esters and amides).

The compounds A1, A2, A3 and A4 are characterized by the values of maximum oral bioavailability ($F_{max}$) in rat, dog and humans (determined by means of liver microsomes as described above) shown in the table below:

| Compound | Rat liver microsomes; Fmax [%] | Human liver microsomes; Fmax [%] | Dog liver microsomes; Fmax [%] |
|---|---|---|---|
| A1 | 92 | 92 | 64 |
| A2 | 93 | >95 | 55 |
| A3 | 83 | >95 | 86 |
| A4 | 74 | 62 | 75 |
| A5 | 89 | 69 | 57 |

Surprisingly it was found, that compounds A1, A2, A3, A4 and A5 show superior properties over compounds of the state of the art.

Compounds A1, A2, A3, A4 and A5 are characterized by the following attributes:

- The $IC_{50}$ determined in an Mps-1 kinase assay with a concentration of 10 μM ATP (as described above) is lower than or equal to 1 nM.
- The $IC_{50}$ determined in an Mps-1 kinase assay with a concentration of 2 mM ATP (as described above) is lower than 2 nM.
- The maximum oral bioavailability ($F_{max}$) in rat (determined by means of rat liver microsomes as described above) is higher than 70%.
- The maximum oral bioavailability ($F_{max}$) in dog (determined by means of dog liver microsomes as described above) is higher than 50%.
- The maximum oral bioavailability ($F_{max}$) in human (determined by means of human liver microsomes as described above) is higher than 60%.
- The $IC_{50}$ determined in a HeLa cell proliferation assay (as described above) is lower than 400 nM.

The following table demonstrates the superiority of compounds A1, A2, A3, A4 and A5 by way of comparison with compounds from prior art as well as with compounds which are structurally similar to said compounds.

| Formula | Specification of Example | Rat liver microsomes; Fmax [%] | Dog liver microsomes; Fmax [%] |
|---|---|---|---|
| | comparative example | | 15 |
| | comparative example disclosed in WO 2011/063908 | | 40 |
| | comparative example disclosed in WO2011/063908 | | 40 |
| | comparative example disclosed in WO2011/063908 | | 19 |

-continued

| Formula | Specification of Example | Rat liver microsomes; Fmax [%] | Dog liver microsomes; Fmax [%] |
| --- | --- | --- | --- |
| | comparative example | 27 | |
| | comparative example | 26 | |
| | comparative example disclosed in WO2011/157688 | 48 | |
| | comparative example | | 12 |

-continued

| Formula | Specification of Example | Rat liver microsomes; Fmax [%] | Dog liver microsomes; Fmax [%] |
|---|---|---|---|
| (structure) | comparative example | | 40 |
| (structure) | comparative example disclosed in WO2011/157688 | | 17 |
| (structure) | comparative example disclosed in WO2012/143329 | | 10 |
| (structure) | comparative example disclosed in WO2012/143329 | | 25 |

-continued

| Formula | Specification of Example | Rat liver microsomes; Fmax [%] | Dog liver microsomes; Fmax [%] |
|---|---|---|---|
| | Compound A1 | 92 | 64 |
| | Compound A2 | 93 | 55 |
| | Compound A3 | 83 | 86 |
| | Compound A4 | 74 | 75 |

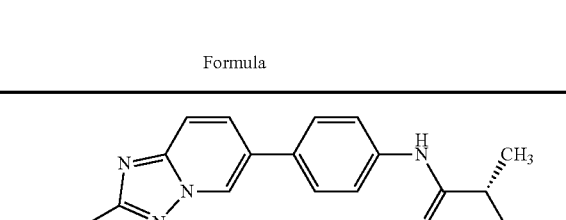

| Formula | Specification of Example | Rat liver microsomes; Fmax [%] | Dog liver microsomes; Fmax [%] |
|---|---|---|---|
| (structure above) | Compound A5 | 89 | 57 |

| Structure | Specification of Example | Mps-1 Inhibition, IC$_{50}$ (Assay with 10 μM ATP) | Inhibition of cell proliferation, cell line: HeLa; IC$_{50}$ |
|---|---|---|---|
| (structure) | comparative example | | 1500 nM |
| (structure) | comparative example | 11 nM | 1400 nM |
| (structure) | comparative example disclosed in WO2011/063908 | 13 nM | |

-continued

| Structure | Specification of Example | Mps-1 Inhibition, IC$_{50}$ (Assay with 10 μM ATP) | Inhibition of cell proli-feration, cell line: HeLa; IC$_{50}$ |
|---|---|---|---|
| 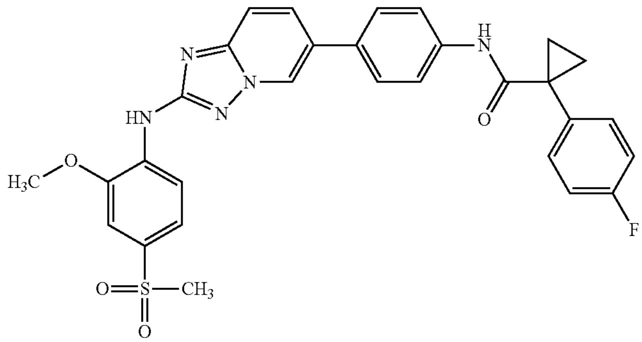 [SMILES: COc1cc(S(C)(=O)=O)ccc1Nc1nc2ccc(-c3ccc(NC(=O)C4(c5ccc(F)cc5)CC4)cc3)cn2n1] | comparative example | 15 nM | |
| 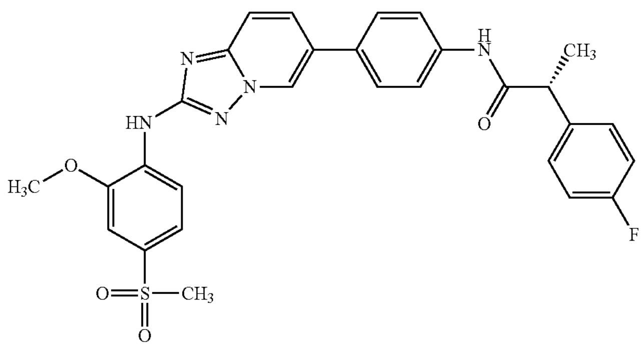 [SMILES: COc1cc(S(C)(=O)=O)ccc1Nc1nc2ccc(-c3ccc(NC(=O)[C@H](C)c4ccc(F)cc4)cc3)cn2n1] | Compound A1 | <1 nM | <400 nM |
| 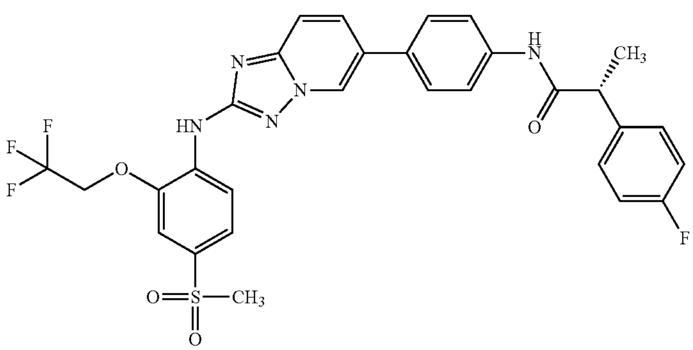 [SMILES: C[C@@H](C(=O)Nc1ccc(-c2ccc3nc(Nc4ccc(S(C)(=O)=O)cc4OCC(F)(F)F)nn3c2)cc1)c1ccc(F)cc1] | Compound A2 | <1 nM | <200 nM |
| 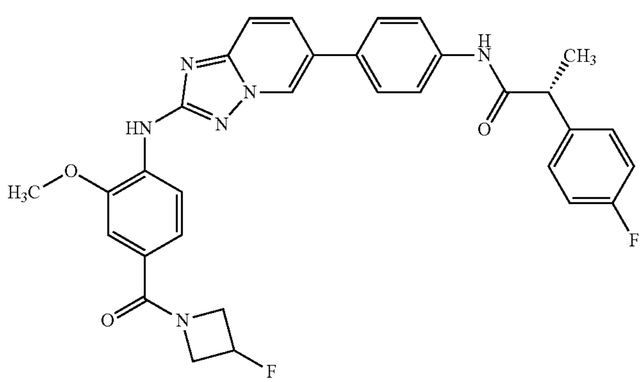 [SMILES: COc1cc(C(=O)N2CC(F)C2)ccc1Nc1nc2ccc(-c3ccc(NC(=O)[C@H](C)c4ccc(F)cc4)cc3)cn2n1] | Compound A3 | <1 nM | <100 nM |

| Structure | Specification of Example | Mps-1 Inhibition, IC$_{50}$ (Assay with 10 μM ATP) | Inhibition of cell proli-feration, cell line: HeLa; IC$_{50}$ |
|---|---|---|---|
| [structure of Compound A4: triazolopyridine core linked to phenyl-acetamide with 4-fluorophenyl and (S)-methyl group; NH-linked 2-methoxy-4-(azetidin-1-ylcarbonyl)phenyl substituent] | Compound A4 | <1 nM | <100 nM |
| [structure of Compound A5: triazolopyridine core linked to phenyl-acetamide with 4-fluorophenyl and (S)-methyl group; NH-linked 2-(2,2,2-trifluoroethoxy)-4-(3-fluoroazetidin-1-ylcarbonyl)phenyl substituent] | Compound A5 | <1 nM | <100 nM |

| Prior Art Document | Example No. | Mps-1 Inhibition, IC$_{50}$ (Assay with 10 μM ATP) | Inhibition of cell proliferation, cell Line: HeLa; IC$_{50}$ |
|---|---|---|---|
| WO 2011/064328 A1 | 11.001 | 20 nM | |
| WO 2011/064328 A1 | 11.002 | 21 nM | |
| WO 2011/064328 A1 | 11.005 | 27 nM | |
| WO 2011/064328 A1 | 11.006 | 28 nM | |
| WO 2011/064328 A1 | 11.007 | 66 nM | |
| WO 2011/064328 A1 | 11.018 | 58 nM | |
| WO 2011/064328 A1 | 11.028 | | 1100 nM |
| WO 2011/064328 A1 | 11.029 | | 630 nM |
| WO 2011/064328 A1 | 11.030 | 16 nM | |
| WO 2011/064328 A1 | 11.031 | 18 nM | |
| WO 2011/064328 A1 | 11.032 | 20 nM | |
| WO 2011/064328 A1 | 11.033 | 23 nM | |
| WO 2011/064328 A1 | 11.037 | | 1100 nM |
| WO 2011/064328 A1 | 11.042 | 53 nM | |
| WO 2011/064328 A1 | 11.043 | 60 nM | |
| WO 2011/064328 A1 | 11.076 | | 730 nM |
| WO 2011/064328 A1 | 11.077 | 16 nM | |
| WO 2011/064328 A1 | 11.078 | 23 nM | |
| WO 2011/064328 A1 | 11.079 | 24 nM | |
| WO 2011/064328 A1 | 11.080 | 25 nM | |
| WO 2011/064328 A1 | 11.081 | 28 nM | |
| WO 2011/064328 A1 | 11.083 | 32 nM | |
| WO 2011/064328 A1 | 11.084 | 40 nM | |
| WO 2011/064328 A1 | 11.085 | | 1800 nM |
| WO 2011/064328 A1 | 11.086 | | 2200 nM |
| WO 2011/064328 A1 | 11.087 | | 870 nM |
| WO 2011/064328 A1 | 11.088 | 15 nM | |
| WO 2011/064328 A1 | 11.089 | 25 nM | |
| WO 2011/064328 A1 | 11.091 | | 1300 nM |
| WO 2011/064328 A1 | 11.092 | | 820 nM |
| WO 2011/064328 A1 | 11.093 | | 2400 nM |
| WO 2011/064328 A1 | 11.094 | | 1400 nM |
| WO 2011/064328 A1 | 11.095 | | 2000 nM |
| WO 2011/064328 A1 | 11.096 | | 1900 nM |

| Prior Art Document | Example No. | Inhibition of cell proliferation, cell Line: HeLa; IC$_{50}$ | Rat liver microsomes; Fmax [%] |
|---|---|---|---|
| WO 2011/063908 A1 | 3.3 | 1500 nM | |
| WO 2011/063908 A1 | 3.4 | 1300 nM | |
| WO 2011/063908 A1 | 3.5 | | 27 |
| WO 2011/063908 A1 | 3.6 | | 40 |
| WO 2011/063908 A1 | 3.9 | | 21 |
| WO 2011/063908 A1 | 3.10 | 930 nM | |
| WO 2011/063908 A1 | 3.11 | | 25 |
| WO 2011/063908 A1 | 4.1 | | 40 |
| WO 2011/063908 A1 | 7.1 | | 29 |

The invention claimed is:

1. A compound of formula (I):

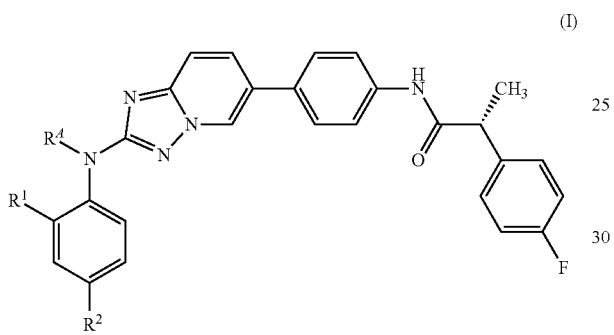

in which:
$R^4$ represents a group selected from:
—C(=O)—(CH$_2$)$_3$—N(H)R$^3$,
—C(=O)—(CR$^4$R$^5$)—N(R$^6$)R$^7$,
—C(=O)—O—(CH$_2$)$_2$—N(H)R$^3$,
—C(=O)—O—(CR$^4$R$^5$)—O—P(=O)(OH)$_2$,
—C(=O)—O—(CR$^4$R$^5$)—O—C(=O)—R$^8$, and
—C(=O)—O—(CR$^4$R$^5$)—O—C(=O)—CH(R$^6$)—NH—C(=O)—R$^9$;

$R^1$ represents a group selected from methoxy- and 2,2,2-trifluoroethoxy-;

$R^2$ represents a group selected from:

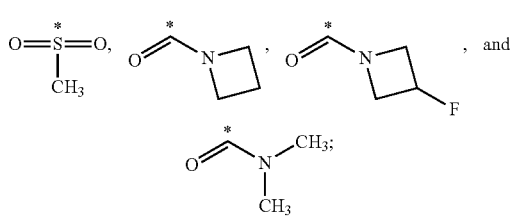

wherein "*" indicates the point of attachment to the phenyl ring $R^2$ is attached to;

$R^3$ represents a group selected from:
C$_1$-C$_6$-alkyl, C$_3$-C$_6$-cycloalkyl-, and
4- to 7-membered heterocycloalkyl-;
said group being optionally substituted, one or more times, identically or differently, with a group selected from:
—OH, —NH$_2$, —N(H)R$^{10}$, —N(R$^{10}$)R$^{11}$, and —O—P(=O)(OH)$_2$;

$R^4$ and $R^5$, independently from each other, represent a group selected from a hydrogen atom and a C$_1$-C$_3$-alkyl- group, or $R^4$ and $R^5$, together with the carbon atom to which they are attached, form a C$_3$-C$_6$-cycloalkyl ring;

$R^6$ represents a hydrogen atom or a C$_1$-C$_3$-alkyl- group;

$R^7$ represents a hydrogen atom or a group —C(=O)R$^9$;

$R^8$ represents a group selected from:
C$_1$-C$_6$-alkyl, C$_3$-C$_6$-cycloalkyl-, and
4- to 7-membered heterocycloalkyl-;
said group being optionally substituted, one or more times, identically or differently, with a group selected from:
—OH, —NH$_2$, —N(H)R$^{10}$, —N(R$^{10}$)R$^{11}$, and —O—P(=O)(OH)$_2$;

$R^9$ represents a group

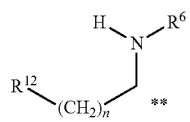

or $R^9$ represents a group selected from:

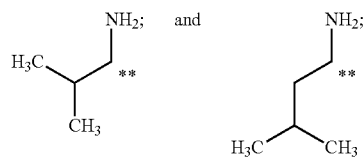

wherein "**" indicates the point of attachment to the carbonyl group R$^9$ is attached to;

$R^{10}$ and $R^{11}$, independently from each other, represent a group selected from a hydrogen atom and a C$_1$-C$_3$-alkyl- group, or $R^{10}$ and $R^{11}$, together with the nitrogen atom to which they are attached form a 4- to 7-membered heterocycloalkyl ring;

$R^{12}$ represents a group selected from a hydrogen atom, —OH, —NR$^{10}$R$^{11}$, and —NH—C(=NH)—NH$_2$;

n is an integer of 0, 1, 2, 3 or 4;

or a tautomer or a salt thereof, or a mixture of same.

2. A compound according to claim 1, wherein:
$R^4$ represents a group selected from:
—C(=O)—(CH$_2$)$_3$—N(H)R$^3$,
—C(=O)—O—(CR$^4$R$^5$)—O—C(=O)—R$^8$, and
—C(=O)—O—(CR$^4$R$^5$)—O—C(=O)—CH(R$^6$)—NH—C(=O)—R$^9$,
or a tautomer or a salt thereof, or a mixture of same.
3. A compound according to claim 1, wherein:
$R^4$ represents a group:
—C(=O)—O—(CR$^4$R$^5$)—O—C(=O)—R$^8$,
or a tautomer or a salt thereof, or a mixture of same.
4. A compound according to claim 1, wherein:
$R^1$ represents a methoxy- group,
or a tautomer or a salt thereof, or a mixture of same.
5. A compound according to claim 1, wherein:
$R^2$ represents a —S(=O)$_2$CH$_3$ group,
or a tautomer or a salt thereof, or a mixture of same.
6. A compound according to claim 1, wherein:
$R^3$ represents a C$_1$-C$_3$-alkyl- group,
or a tautomer or a salt thereof, or a mixture of same.
7. A compound according to claim 1, wherein:
$R^4$ represents a hydrogen atom or a C$_1$-C$_3$-alkyl- group, and
$R^5$ represents a hydrogen atom,
or a tautomer or a salt thereof, or a mixture of same.
8. A compound according to claim 1, wherein:
$R^6$ represents a hydrogen atom or a methyl- group,
or a tautomer or a salt thereof, or a mixture of same.
9. A compound according to claim 1, wherein:
$R^8$ represents a group selected from:
C$_1$-C$_6$-alkyl, substituted one or more times, identically or differently, with a group selected from: —NH$_2$, —N(H)R$^{10}$, and —N(R$^{10}$)R$^{11}$, and
4- to 7-membered heterocycloalkyl-, optionally substituted, one or more times, identically or differently, with a group selected from: —NH$_2$, —N(H)R$^{10}$, and —N(R$^{10}$)R$^{11}$,
or a tautomer or a salt thereof, or a mixture of same.
10. A compound according to claim 1, wherein:
$R^9$ represents a group selected from:

[structures shown]

wherein "**" indicates the point of attachment to the carbonyl group $R^9$ is attached to,
or a tautomer or a salt thereof, or a mixture of same.
11. A compound according to claim 1, wherein:
$R^{10}$ and $R^{11}$, independently from each other, represent a group selected from a hydrogen atom and a C$_1$-C$_3$-alkyl-group,
or a tautomer or a salt thereof, or a mixture of same.
12. A compound according to claim 1, wherein:
$R^{12}$ represents a group —NR$^{10}$R$^{11}$,
or a tautomer or a salt thereof, or a mixture of same.
13. A compound according to claim 1, which is selected from the group consisting of:
({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy) methyl piperidine-4-carboxylate trifluoroacetate,
({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy) methyl L-valinate hydrochloride,
({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy) methyl L-leucinate hydrochloride,
({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy) methyl N-methyl-L-valinate hydrochloride,
({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy) methyl 3-methyl-L-valinate hydrochloride,
(phosphonooxy)methyl [6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamate,
({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy) methyl 3-methyl-L-isovalinate hydrochloride,
({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy) methyl 3-amino-2,2-dimethylpropanoate trifluoroacetate,
({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy) methyl L-lysyl-L-valinate dihydrochloride,
(1RS)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy) ethyl L-lysyl-L-valinate dihydrochloride (mixture of 2 epimers),
({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy) methyl L-valyl-L-valinate hydrochloride,
(1RS)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy) ethyl L-valyl-L-valinate hydrochloride (mixture of 2 epimers),
(1RS)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy) ethyl L-valinate hydrochloride (mixture of 2 epimers),
(1RS)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy) ethyl 3-methyl-L-valinate hydrochloride (mixture of 2 epimers), (1R or 1S)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)ethyl-3-methyl-L-valinate hydrochloride (single stereoisomer A), (1S or 1R)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)ethyl-3-methyl-L-valinate hydrochloride (single stereoisomer B), (1RS)-1-({[6-(4-{[(2R)-2-(4-fluorophenyl)propanoyl]amino}phenyl)[1,2,4]triazolo[1,5-α]pyridin -2-yl][2-methoxy-4-(methylsulfonyl)phenyl]carbamoyl}oxy)ethyl-L-isoleucinate hydrochloride (mixture of 2 epimers), (1S or 1R)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)ethyl-L-isoleucinate hydrochloride (single stereoisomer B), (1R or 1S)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)ethyl-L-isoleucinate hydrochloride (single stereoisomer A), N-[6-(4-{[(2R)-2-(4-fluorophenyl)propanoyl]amino}phenyl)[1,2,4]triazolo[1,5-α]pyridin -2-yl]-N-[2-methoxy-4-(methylsulfonyl)phenyl]-4-(methylamino)butanamide trifluoroacetate, N-[6-(4-{[(2R)-2-(4-fluorophenyl)propanoyl]amino}phenyl)[1,2,4]triazolo[1,5-α]pyridin -2-yl]-N-[2-methoxy-4-(methylsulfonyl)phenyl]-4-(methylamino)butanamide hydrochloride, (1RS)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)-2-methylpropyl 3-methyl-L-valinate hydrochloride (mixture of 2 epimers), (1R or S)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)-2-methylpropyl-L-valinate hydrochloride (single stereoisomer A), (1S or R)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)-2-methylpropyl-L-valinate hydrochloride (single stereoisomer B), (1RS)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)-2-methylpropyl-L-valinate hydrochloride (mixture of 2 epimers), (1RS)-1-({[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamoyl}oxy)-2-methylpropyl-2-methylalaninate hydrochloride (mixture of 2 epimers), ({[6-(4-{[(2R)-2-(4-fluorophenyl)propanoyl]amino}phenyl)[1,2,4]triazolo[1,5-α]pyridin-2-yl][4-(methylsulfonyl)-2-(2,2,2-trifluoroethoxy)phenyl]carbamoyl}oxy)methyl 3-methyl-L-valinate hydrochloride, ({[6-(4-{[(2R)-2-(4-fluorophenyl)propanoyl]amino}phenyl)[1,2,4]triazolo[1,5-α]pyridin-2-yl][4-(methylsulfonyl)-2-(2,2,2-trifluoroethoxy)phenyl]carbamoyl}oxy)methyl L-valinate hydrochloride,

[({4-[(3-fluoroazetidin-1-yl)carbonyl]-2-(2,2,2-trifluoroethoxy)phenyl}[6-(4-{[(2R)-2-(4-fluorophenyl)propanoyl]amino}phenyl)[1,2,4]triazolo[1,5-α]pyridin-2-yl]carbamoyl)oxy]methyl 3-methyl-L-valinate hydrochloride, 2-(methylamino)ethyl[6-(4-{[(2R)-2-(4-fluorophenyl)propanoyl]amino}phenyl)[1,2,4]triazolo[1,5-α]pyridin-2-yl][2-methoxy-4-(methylsulfonyl)phenyl]carbamate hydrochloride, and (2R)-2-(4-fluorophenyl)-N-[4-(2-{[2-methoxy-4-(methylsulfonyl)phenyl](N-methylglycyl)amino}[1,2,4]triazolo[1,5-α]pyridin-6-yl)phenyl]propanamide trifluoroacetate;

or a tautomer or a salt thereof, or a mixture of same.

14. A pharmaceutical composition comprising a compound according to claim 1, or a tautomer or a pharmaceutically acceptable salt thereof, or a mixture of same, and a pharmaceutically acceptable diluent or carrier.

\* \* \* \* \*

SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: biotinylated peptide of the amino-acid sequence
      PWDPDDADITEILG

<400> SEQUENCE: 1

Pro Trp Asp Pro Asp Asp Ala Asp Ile Thr Glu Ile Leu Gly
1               5                   10